US008119768B2

(12) United States Patent
Liu

(10) Patent No.: US 8,119,768 B2
(45) Date of Patent: Feb. 21, 2012

(54) COMPOSITIONS AND METHODS FOR MODULATING AMPA RECEPTOR-MEDIATED EXCITOTOXICITY

(75) Inventor: Fang Liu, Toronto (CA)

(73) Assignee: Centre for Addiction and Mental Health, Toronto (CA)

( * ) Notice: Subject to any disclaimer, the term of this patent is extended or adjusted under 35 U.S.C. 154(b) by 0 days.

(21) Appl. No.: 12/310,558

(22) PCT Filed: Aug. 31, 2007

(86) PCT No.: PCT/CA2007/001539

§ 371 (c)(1),
(2), (4) Date: May 10, 2010

(87) PCT Pub. No.: WO2008/025163

PCT Pub. Date: Mar. 6, 2008

(65) Prior Publication Data

US 2010/0210521 A1 Aug. 19, 2010

Related U.S. Application Data

(60) Provisional application No. 60/841,195, filed on Aug. 31, 2006.

(51) Int. Cl.
*A61K 38/00* (2006.01)
*C07K 14/00* (2006.01)

(52) U.S. Cl. ........................................ 530/350; 514/1.1

(58) Field of Classification Search ........................ None
See application file for complete search history.

(56) References Cited

U.S. PATENT DOCUMENTS

| | | | | |
|---|---|---|---|---|
| 5,925,549 | A * | 7/1999 | Hsueh et al. | 435/69.7 |
| 6,040,175 | A * | 3/2000 | Kamboj et al. | 435/325 |
| 2003/0203372 | A1 | 10/2003 | Ward et al. | |
| 2004/0086891 | A1 | 5/2004 | Tatton et al. | |

FOREIGN PATENT DOCUMENTS

WO 2005/033311 4/2005

OTHER PUBLICATIONS

Passafaro et al. Induction of dendritic spines by an extracellular domain of AMPA receptor subunit GluR2, (Aug. 7, 2003), Nature 424:677-681.*

Chuang, D-M et al., "Gyceraldehyde-3-phosphate dehydrogenase, apoptosis and neurodegenerative diseases", Ann. Rev. Pharm. and Tox., Feb. 7, 2005, vol. 45, pp. 269-290, ISSN: 0362-1642.

Choi, et al., "Isolation of the heterogeneous nuclear RNA-ribonucleoprotein complex (hnRNP): A unique supramolecular assembly", Proc. Natl. Acad. Sci., Dec. 1, 1984, vol. 81, No. 23, pp. 7471-7475.

Dong, et al., "Characterization of the Glutamate Receptor-Interacting Proteins GRIP1 and GRIP2", J. Neurosci., Aug. 15, 1999, vol. 19(16), pp. 6930-6941.

Doucet, et al., "Identification of Low Molecular Weight GTP-binding Proteins and Their Sites of Interaction in Subcellular Fractions from Skeletal Muscle", The Journal of Biological Chemistry, Sep. 15, 1991, vol. 266, No. 26, pp. 17613-17620.

Fuchtbauer, et al., "Actin-severing activity copurifies with phosphofructokinase", Proc. Natl. Acad. Sci., Dec. 15, 1986, vol. 83, No. 24, pp. 9502-9506.

Geiger, et al., Relative Abundance of Subinit mRNAs Determines Gating and Ca2+ Permeability of AMPA Receptors in Principal Neurons and Interneurons in Rat CNS, Neuron, Jul. 1995, vol. 15, pp. 193-204.

Glaser, et al., "Rapid Plasmenylethanolamine-Selective Fusion of Membrane Bilayers Catalyzed by an Isoform of glyceraldehyde-3-Phosphate Dehydrogenase: Discrimination between Glycolytic and Fusogenic Roles of Individual Isoforms", Biochemistry, 1995, vol. 34, No. 38, pp. 12193-12203.

Hara, et al., "Neuroprotection by pharmacologic blockage of GAPDH death cascade", Proc. Natl. Acad. Sci., Mar. 7, 2006, vol. 103, No. 10, pp. 3887-3889.

Huitorel, et al., "Bundling of microtubules by glyceraldehyde-3-phosphate dehydrogenase and its modulation by ATP", Eur. J. Biochem., 1985, vol. 150, pp. 265-269.

Humbert, et al., "Inositol 1, 4, 5-Trisphosphate Receptor Is Located to the Inner Nuclear Membrane Vindicating Regulation of Nuclear Calcium Signaling by Inositol 1, 4, 5-Trisphosphate", The Journal of Biological Chemistry, Jan. 5, 1996, vol. 271, No. 1, pp. 478-485.

Iihara, et al., The Influence of Glutamate Receptor 2 Expression on Excitotoxicity in GluR2 Null Mutant Mice, J. Neurosci., Apr. 1, 2001, vol. 21(7), pp. 2224-2239.

Ikemoto, et al., "Glycolysis and Glutamate Accumulation into Synaptic Vesicles", The Journal of Biological Chemistry, Feb. 21, 2003, vol. 278, No. 8, pp. 5929-5940.

Jonas, et al., "Differences in Ca2+ Permeability of AMPA-type Glutamate Receptor Channels in Neocortical Neurons Caused by Differential GluR-B Subunit Expression", Neuron, Jun. 1994, vol. 12, pp. 1281-1289.

Jong, et al., "Functional Metabotropic Glutamate Receptors on Nuclei from Brain and Primary Cultured Striatal Neurons", The Journal of Biological Chemistry, Aug. 26, 2005, vol. 280, No. 34, pp. 30469-30480.

Jong, et al., "Nuclear localization of functional metabotropic glutamate receptor mGlu1 in HEK293 cells and cortical neurons: role in nuclear calcium mobilization and development", J. Neurochem., 2007, vol. 101, pp. 458-469. Lakkaraju, et al., "Neurons Are Protected from Excitotoxic Death by p53 Antisense Oligonucleotides Delivered in Anionic Liposomes", The Journal of Biological Chemistry, Aug. 24, 2001, vol. 276, No. 34, pp. 32000-32007.

Lee, et al., "Dual Regulation of NMDA Receptor Functions by Direct Protein-Protein Interactions with the Dopamine D1 Receptor", Cell, Oct. 18, 2002, vol. 111, pp. 219-230.

Lee, et al., "Clathrin Adaptor AP2 and NSF Interact with Overlapping Sites of GluR2 and Play Distinct Roles in AMPA Receptor Trafficking and Hippocampal LTD", Neuron, Nov. 14, 2002, vol. 36, pp. 661-674.

(Continued)

*Primary Examiner* — John Ulm

(57) ABSTRACT

The present invention provides AMPAR excitotoxicity mediating polypeptides comprising the GluR2 NT1-3-2 (Y142-K172) amino acid sequence (SEQ ID NO:1) or the GAPDH (2-2-1-1) (I221-E250) amino acid sequence (SEQ ID NO:2). Also disclosed are nucleotide sequences encoding the polypeptides, methods of inhibiting GAPDH association with the GluR2 subunit or p53. Methods of inhibiting AMPA receptor mediated excitotoxicity using the polypeptides and nucleic acids are also disclosed.

12 Claims, 30 Drawing Sheets

OTHER PUBLICATIONS

Li, et al, "Down-regulation of GluR2 is associated with Ca2+-dependent protease activities in kainate-induced apoptotic cell death in cultured [correction of culturd] rat hippocampal neruons", Neuroscience Letters, 2003, vol, 352, pp. 105-108.
Lin, et al, "Distinct molecular mechanisms and divergent endocytotic pathways of AMPA receptor internalization", Nature Neuroscience, Dec. 2000, vol. 3, No. 12, pp. 1282-1290.
Lin, et al., "Nuclear localization of EGF receptor and its potential new role as a transcription factor", Nature Cell Biology, Sep. 2001, vol. 3, pp. 802-808.
Liu, et al., "Ischemic Insults Direct Glutamate Receptor Subunit 2-Lacking AMPA Receptors to Synaptic Sites", J. Neurosci., May 17, 2006, vol. 26(20), pp. 5309-5319.
Liu, et al., "Direct protein-protein coupling enables cross-talk between dopamine D5 and gamma-aminobutyric acid A receptors", Nature, Jan. 20, 2000, vol. 403, pp. 274-280.
Liu et al., "Expression of Ca2+-Permeable AMPA Receptor Channels Primes Cell Death in Transient Forebrain Ischemia", Neuron, Jul. 8, 2004, vol. 43, pp. 43-55.
Lu, et al., "Angiotensin II-Induced Nuclear Targeting of the Angiotensin Type 1 (AT1) Receptor in Brain Neurons", Endocrinology, 1998, vol. 139, No. 1, pp. 365-375.
Man, et al., "Regulation of AMPA Receptor-Mediated Synaptic Transmission by Clathrin-Dependent Receptor Internalization", Neuron., Mar. 2000, vol. 25, pp. 649-662.
Melikian, et al, "Membrane Trafficking Regulates the Activity of the Human Dopamine Transporter", J. Neurosci., Sep. 15, 1999, vol. 19(18), pp. 7699-7710.
Miller, et al., "Neuronal life and death: an essential role for the p53 family", Cell Death and Differentiation, 2000, vol. 7, pp. 880-888.
Nelson, et al., "pH-regulated Secretion of a Glyceraldehyde-3-Phosphate Dehydrogenase from Streptococcus gordonii FSS2: Purification, Characterization and Cloning of the Gene Encoding this Enzyme", Journal of Dental Research, Jan. 2001, vol. 80(1), pp. 371-377.
Nishimune, et al, "NSF Binding to GluR2 Regulates Synaptic Transmission", Neuron., Jul. 1998, vol. 21, pp. 87-97.
Robbins, et al., "A Mutation in Glyceraldehyde 3-Phosphate Dehydrogenase Alters Endocytosis in CHO Cells", The Journal of Cell Biology, Sep. 1, 1995, vol. 130, pp. 1093-1104.
Saglietti, et al, Extracellular Interactions between GluR2 and N-Cadherin in Spine Regulation, Neuron, May 3, 2007, vol. 54, pp. 461-477.
Sakhi, et al., "p53 induction is associated with neuronal damage in the central nervous system", Proc. Natl. Acad. Sci., Aug. 2, 1994, vol. 91, No. 16, pp. 7525-7529.
Seifert, et al., "Characterization of group B streptococcal glyceraldehyde-3-phosphate dehydrogenase: surface localization, enzymatic activity, and protein-protein interactions", Can. J. Microbiol., 2003, vol. 49, pp. 350-356.
Srivastava, et al., "Novel Anchorage of GluR2/3 to the Postsynaptic Density by the AMPA Receptor-Binding Protein ABP", Neuron, Sep. 1998, vol. 21, pp. 581-591.
Uberti, et al., "Induction of tumour-suppressor phosphoprotein p53 in the apoptosis of cultured rat cerebellar neurones triggered by excitatory amino acids", European Journal of Neuroscience, 1998, vol. 10, pp. 246-254.
Valtschanoff, et al., "SAP97 concentrates at the postsynaptic density in cerebral cortex", European Journal of Neuroscience, 2000, vol. 12, pp. 3605-3614.
Ventura, et al., "Nuclear Opioid Receptors Activate Opioid Peptide Gene Transcription in Isolated Myocardial Nuclei", The Journal of Biological Chemistry, May 29, 1998, vol. 273, No. 22, pp. 13383-13386.
Wyszynski, et al., "Associate of AMPA Receptors with a Subset of Glutamate Receptor-Interacting Protein In Vivo", J. Neurosci., Aug. 1, 1999, vol. 19(15), pp. 6528-6537.
Xia, et al, "Clustering of AMPA Receptors by the Synaptic PDZ Domain-Containing Protein PICK1", Neuron. Jan. 1999, vol. 22, pp. 179-187.
Yamaji, et al., "Glyceraldehyde-3-phosphate dehydrogenase in the extracellular space inhibits cell spreading", Biochimica et Biophysica Acta, 2005, vol. 1726, pp. 261-271.
Zeevalk, et al., "Excitotoxicity at Both NMDA and Non-NMDA Glutamate Receptors Is Antagonized by Aurintricarboxylic Acid: Evidence for Differing Mechanisms of Action", J. Neurochem., 1995, vol. 64, No. 4, pp. 1749-1758.
Beretta, et al., "NSF interaction is important for direct insertion of GluR2 at synaptic sites", Mol. Cell. Neurosci., 2005, vol. 28, pp. 650-660.
Hollmann, et al., "Cloned Glutamate Receptors", Annu. Rev. Neurosci., 1994, vol. 17, pp. 31-108.
Bliss, et al., "A synaptic model of memory: long-term potentiation in the hippocampus", Nature, Jan. 7, 1993, vol. 361, pp. 31-39.
Simon, et al., "Blockade of N-Methyl-D-Aspartate Receptors May Protect Against Ischemic Damage in the Brain", Science, Nov. 16, 1984, vol. 226, pp. 850-852.
Choi, "Calcium: still center-stage in hypoxic-ischemic neuronal death", Trends Neurosci., 1995, vol. 18, No. 2, pp. 58-60.
Lee, et al., "The changing landscape of ischaemic brain injury mechanisms", Nature, Jun. 24, 1999, vol. 399/Supp, pp. A7-A14.
Pulsinelli, et al., "Regional Cerebral Blood Flow and Glucose Metabolism Following Transient Forebrain Ischemia", Annals of Neurology, May 1982, vol. 11, No. 5, pp. 499-509.
Schmidt-Kastner, et al., "Selective Vulnerability of the Hippocampus in Brain Ischemia", Neuroscience, 1991, vol. 40, No. 3, pp. 599-636.
Pellegrini-Giampietro, et al., "Switch in glutamate receptor subunit gene expression in CA1 subfield of hippocampus following global ischemia in rats", Proc. Natl. Acad. Sci., Nov. 1992, vol. 89, pp. 10499-10503.
Gill, et al., "Pharmacology of AMPA Antagonists and Their Role in Neuroprotection", Int. Rev. Neurobiol., 1997, vol. 40, pp. 197-232.
Oguro, et al., "Knockdown of AMPA Receptor GluR2 Expression Causes Delayed Neurodegeneration and Increases Damage by Sublethal Ischemia in Hippocampal CA1 and CA3 Neurons", J. Neurosci., Nov. 1, 1999, vol. 19(21), pp. 9218-9227.
Weiss, et al., "Ca2+-Zn2+ permeable AMPA or kinate receptors: possible key factors in selective neurodegeneration", Trends Neurosci., 2000, vol. 23, No. 8, pp. 365-371.
Yin, et al., "Blockage of Ca2+-Permeable AMPA/Kainate Channels Decreases Oxygen-Glucose Deprivation-Induced Zn2+ Accumulation and Neuronal Loss in Hippocampal Pyramidal Neurons", J. Neurosci., Feb. 15, 2002, vol. 22 (4), pp. 1273-1279.
Wang, et al., "Cdk5 activation induces hippocampal CA1 cell death by directly phosphorylating NMDA receptors", Nature Neuroscience, Oct. 2003, vol. 6, No. 10, pp. 1039-1047.
Greengard, et al., "Enhancement of the Glultamate Response by cAMP-Dependent Protein Kinase in Hippocampal Neurons", Science, Sep. 6, 1991, vol. 253, No. 5024, pp. 1135-1138.
Wang, et al., "Modulation of AMPA/kainate receptors in cultured murine hippocampal neurones by protein kinase C", J. Physiol., 1994, vol. 475.3, pp. 431-437.
Yakel, et al., "Identification of Ca2+/calmodulin-dependent protein kinase II regulatory phosphorylation site in non-N-methyl-D-aspartate glutamate receptors", Proc. Nat. Acad. Sci., Feb. 1995, vol. 92, pp. 1376-1380.
Soderling, et al., "Structure and regulation of calcium/calmodulin-dependent protein kinases II and IV", Biochimica et Biophysica Acta, 1996, vol. 1297, pp. 131-138.
Barria, et al., "Identification of the Ca2+/Calmodulin-dependent Protein Kinase II Regulatory Phosphorylation Site in the alpha-Amino-3-hydroxyl-5-methyl-4-isoxazole-propionate-type Glutamate Receptor", J. Biol. Chem. Dec. 26, 1997, vol. 272, No. 52, pp. 32727-32730.
Xia, et al., "Clustering of AMPA Receptors by the Synaptic PDZ Domain-Containing Protein PICK1", Neuron, Jan. 1999, vol. 22, pp. 179-187.
Dong, et al., "GRIP: a synaptic PDZ domain-containing protein that interacts with AMPA receptors", Nature, Mar. 20, 1997, vol. 386, pp. 279-284.
Osten, et al., "The AMPA Receptor GluR2 C Terminus Can Mediate a Reversible, ATP-Dependent Interaction with NSF and alpha- and beta-SNAPs", Neuron, Jul. 1998, vol. 21, pp. 99-110.

Daw, et al., "PDZ Proteins Interacting with C-Terminal GluR2/3 Are Involved in a PKC-Dependent Regulation of AMPA Receptors at Hippocampal Synapses", Neuron, Dec. 2000, vol. 28, pp. 873-886.
Allison, et al., "Role of Actin in Anchoring Postsynaptic Receptors in Cultured Hippocampal Neurons: Differential Attachment of NMDA versus AMPA Receptors", J. Neurosci., Apr. 1, 1998, vol. 18(7), pp. 2423-2436.
O'Brien, et al., "Synaptic Clustering of AMPA Receptors by the Extracellular Immediate-Early Gene Product Narp", Neuron, Jun. 1999, vol. 23, pp. 309-323.
Chuang, et al., "Glyceraldehyde-3-Phosphate Dehydrogenase, Apoptosis, and Neurodegenerative Diseases", Annu. Rev. Pharmacol. Toxicol., 2005, vol. 45, pp. 269-290.
Sirover , "New Nuclear Functions of the Glycolytic Protein, Glyceraldehyde-3-Phosphate Dehydrogenase, in Mammalian Cells", Journal of Cellular Biochemistry, 2005, vol. 95, pp. 45-52.
Sawa, et al., "Glyceraldehyde-3-Phosphate dehydrogenase: Nuclear translocation participates in neuronal and nonneuronal cell death", Proc. Natl. Acad. Sci., Oct. 14, 1997, vol. 94, No. 21, pp. 11669-11674.
Ishitani, et al., "Nuclear Localization of Overexpressed Glyceraldehyde-3-Phosphate Dehydrogenase in Cultured Cerebellar Neurons Undergoing Apoptosis", Mol. Pharmacol., 1998, vol. 53, pp. 701-707.
Ishitani, et al., "Glyceraldehyde-3-phosphate dehydrogenase antisense oligodeoxynucleotides protect against cytosine arabinonucleoside-induced apoptosis in cultured cerebellar neurons", Proc. Natl. Acad. Sci., Sep. 3, 1996, vol. 93, No. 18, pp. 9937-9941.
Hara, et al., "S-nitrosylated GAPDH initiates apoptotic cell death by nuclear translocation following Siah1 binding", Nature Cell Biology, Jul. 2005, vol. 7, No. 7, pp. 665-674.
Tsai, et al., "Studies on a Mammalian Cell Protein (P8) with Affinity for DNA in vitro", J. Mol. Biol., 1973, vol. 73, pp. 307-316.
Singh, et al., "Sequence-Specific Binding of Transfer RNA by Glyceraldehyde-3-Phosphate Dehydrogenase", Science, Jan. 15, 1993, vol. 259, No. 5093, pp. 365-368.
Baxi, et al., "Uracil DNA-Glycosylase/Glyceraldehyde-3-Phosphate Dehydrogenase is an Ap4A Binding Protein", Biochemistry,1995, vol. 34, No. 30, pp. 9700-9707.
Nagy, et al., Glyceraldehyde-3-phospate Dehydrogenase Selectively Binds AU-rich RNA in the NAD+-binding Region (Rossmann Fold), J. Biol. Chem., Feb. 10, 1995, vol. 270, No. 6, pp. 2755-2763.
Schultz, et al., "Specific Interaction of Glyceraldehyde 3-Phosphate Dehydrogenase with the 5'-Nontranslated RNA of Hepatitis A Virus", J. Biol. Chem., Jun. 14, 1996, vol. 271, No. 24, pp. 14134-14142.
Tisdale, "Glyceraldehyde-3-phosphate Dehydrogenase Is Required for Vesicular Transport in the Early Secretory Pathway", J. Biol. Chem., Jan. 26, 2001, vol. 276, No. 4, pp. 2480-2486.
Tisdale, "Glyceraldehyde-3-phosphate Dehydrogenase is Phosphorylated by Protein Kinase Ciota/lamda and Plays a Role in Microtubule Dynamics in the Early Secretory Pathway", J. Biol. Chem., Feb. 1, 2002, vol. 277, No. 5, pp. 3334-3341.
Tisdale, "Glyceraldehyde-3-phosphate Dehydrogenase Interacts with Rab2 and Plays an Essential Role in Endoplasmic Reticulum to Golgi Transport Exclusive of Its Glycolytic Activity", J. Biol. Chem., Dec. 24, 2004, vol. 279, No. 52, pp. 54046-54052.
Kumagi, et al., "A Porcine Brain Protein (35 K Protein) which bundles Microtubules and Its Identification as Glyceraldehyde 3-Phosphate Dehydrogenase", J. Biochem., 1983, vol. 93, No. 5, pp. 1259-1269.
Glaser, et al., "Tubulin is the endogenous inhibitor of the glyceraldehyde 3-phosphate dehydrogenase isoform that catalyzes membrane fusion: Implications for the coordinated regulation of glycolysis and membrane fusion", Oct. 29, 2002, vol. 99, No. 22, pp. 14104-14109.
Chen, et al., "Involvement of Glyceraldehyde-3-Phosphate Dehydrogenase (GAPDH) and p53 in Neuronal Apoptosis: Evidence that GAPDH is Upregulated by p53", J. Neurosci., Nov. 1, 1999, vol. 19(21), pp. 9654-9662.
Dastoor, et al, "Potential role of nuclear translocation of glyderaldehyde-3-phosphate dehydrogenase in apoptosis and oxidative stress", Journal of Cell Science, 2001, vol. 114 (9), pp. 1643-1653.
Barbosa, et al., Glyceraldehyde-3-Phosphate Dehydrogenase of Paracoccidioides brasiliensis Is a Cell Surface Protein Involved in Fungal Adhesion to Extracellular Matrix Proteins and Interaction with Cells, Infection and Immunity, Jan. 2006, vol. 74, No. 1, pp. 382-389.
Bhattacharya, et al, "Localization of Functional Prostaglandin E2 Receptors EP3 and EP4 in the Nuclear Envelope", The Journal of Biological Chemistry, May 28, 1999, vol. 274, No. 22, pp. 15719-15724.
Bkaily, et al., "Presence of Functional Endothelin-1 Receptors in Nuclear Membranes of Human Aortic Vascular Smooth Muscle Cells", Journal of Cardiovascular Pharmacology, 2000, vol. 36 (Suppl. 1), pp. S414-S417.
Brooks, et al., "Ubiquitination, phosphorylation and acetylation: the molecular basis for p53 regulation", Current Opinion in Cell Biology, 2003, vol. 15, pp. 164-171.
Carriedo, et al., "Rapid Ca2+ Entry through Ca2+-Permeable AMPA/Kainate Channels Triggers Marked Intracellular Ca2+ Rises and Consequent Oxygen Radical Production", J. Neurosci., Oct. 1, 1998, vol. 18(19), pp. 7727-7738.
Carroll, et al, "Dynamin-dependent endocytosis of ionotropic glutamate receptors", Proc. Natl. Acad. Scie., Nov. 23, 1999, vol. 96, No. 24, pp. 14112-14117.
Chen, et al, "Stargazin regulates synaptic targeting of AMPA receptors by two distinct mechanisms", Nature, Dec. 2000, vol. 408, pp. 936-943.

* cited by examiner

FIGURE 1A: GluR2 NT1-3-2
YYQWDKFAYLYDSDRGLSTLQAVLDSAAEKK (SEQ ID NO:1)

FIGURE 1B: GAPDH(2-2-1-1)
IPELNGKLTGMAFRVPTANVSVVDLTCRLE (SEQ ID NO:2)

FIGURE 1C:DNA sequence of GluR2 amino terminus:

1 atgcaaaaga ttatgcatat ttctgtcctc ctttctcctg ttttatgggg actgattttt
61 ggtgtctctt ctaacagcat acagataggg gggctatttc caaggggcgc tgatcaagaa
121 tacagtgcat ttcgggtagg gatggttcag ttttccactt cggagttcag actgacaccc
181 catatcgaca atttggaggt agccaacagt ttcgcagtca ccaatgcttt ctgctcccag
241 ttttcaagag gagtctacgc aatttttgga ttttatgaca agaagtctgt aaataccatc
301 acatcattct gtgggacact ccatgtgtcc ttcatcacac ctagcttccc aacagatggc
361 acacatccat ttgtcatcca gatgcgacct gacctcaaag gagcactcct tagcttgatt
421 gagtactacc aatgggacaa gttcgcatac ctctatgaca gtgacagagg cttatcaaca
481 ctgcaagctg ttctggattc tgctgcagag aagaagtggc aggtgactgc tatcaatgtg
541 gggaacatca acaatgacaa gaaagatgag acctacagat cgctctttca agatctggag
601 ttaaaaaaag aacggcgtgt aatcctggac tgtgaaaggg ataaagtaaa tgacattgtg
661 gaccaggtta ttaccattgg aaaacatgtt aaagggtacc attatatcat tgcaaatctg
721 ggattcactg atggggacct gctgaaaatt cagtttggag gagcaaatgt ctctggattt
781 cagattgtag actacgatga ttccctggtg tctaaattta tagaaagatg gtcaacactg
841 gaagagaaag aataccctgg agcacacaca gcgacaatta agtatacttc ggccctgacg
901 tatgatgctg tccaagtgat gactgaagca ttccgtaacc ttcggaagca gaggattgaa
961 atatcccgga gaggaaatgc aggggattgt ttggccaacc cagctgtgcc ctggggacaa
1021 ggggtcgaaa tagaaagggc cctcaagcag gttcaagttg aaggcctctc tggaaatata
1081 aagtttgacc agaatggaaa acgaataaac tacacaatta acatcatgga gctcaaaaca
1141 aatggacccc ggaagattgg gtactggagt gaagtggata aaatggttgt caccctaact
1201 gagctcccat caggaaatga cacgtctggg cttgaaaaca agactgtggt ggtcaccaca
1261 atattggaat ctccatatgt tatgatgaag aaaaatcatg aaatgcttga agggaatgag
1321 cgttacgagg gctactgtgt tgacttagct gcagaaattg ccaaacactg tgggttcaag
1381 tacaagctga ctattgttgg ggatggcaag tatggggcca gggatgccga caccaaaatt
1441 tggaatggta tggttggaga gcttgtctac gggaaagctg acattgcaat tgctccatta
1501 actatcactc tcgtgagaga agaggtgatt gacttctcca agcccttcat gagtcttgga
1561 atctctatca tgatcaagaa gcctcagaag tccaaaccag gagtgttttc ctttcttgat
1621 cctttagcct atgag (SEQ ID NO:3)

The shaded and underlined region shows a representative sequence encoding GluR2 NT1-3-2 (Y142-K172).

FIGURE 1D: V22-E545 of GluR2 (GluR2 NT1-3-2 is underlined)

GluR$_2$NT V$_{22}$-E$_{545}$

22 31 41 51
VSSNSIQIG GLFPRGADQE YSAFRVGMVQ FSTSEFRLTP
61 71 81 91
HIDNLEVANS FAVTNAFCSQ FSRGVYAIFG FYDKKSVNTI
101 111 121 131
TSFCGTLHVS FITPSFPTDG THPFVIQMRP DLKGALLSLI
141 151 161 171
EYYQWDKFAY LYDSDRGLST LQAVLDSAAE KKWQVTAINV
181 191 201 211
GNINNDKKDE TYRSLFQDLE LKKERRVILD CERDKVNDIV
221 231 241 251
DQVITIGKHV KGYHYIIANL GFTDGDLLKI QFGGANVSGF
261 271 281 291
QIVDYDDSLV SKFIERWSTL EEKEYPGAHT ATIKYTSALT
301 311 321 331
YDAVQVMTEA FRNLRKQRIE ISRRGNAGDC LANPAVPWGQ
341 351 361 371
GVEIERALKQ VQVEGLSGNI KFDQNGKRIN YTINIMELKT
381 391 401 411
NGPRKIGYWS EVDKMVVTLT ELPSGNDTSG LENKTVVVTT
421 431 441 451
ILESPYVMMK KNHEMLEGNE RYEGYCVDLA AEIAKHCGFK
461 471 481 491
YKLTIVGDGK YGARDADTKI WNGMVGELVY GKADIAIAPL
501 511 521 531
TITLVREEVI DFSKPFMSLG ISIMIKKPQK SKPGVFSFLD
541
PLAYE (SEQ ID NO:4)

FIGURE 1E: Representative GAPDH sequence from *Homo Sapiens* (GAPDH (I221-E250) is underlined)

1 mgkvkvgvng fgrigrlvtr aafnsgkvdi vaindpfidl nymvymfqyd sthgkfhgtv 61 kaengklvin gnpitifqer dpskikwgda gaeyvvestg vfttmekaga hlqggakrvi 121 isapsadapm fvmgvnheky dnslkiisna scttnclapl akvihdnfgi veglmttvha 181 itatqktvdg psgklwrdgr galqniipas tgaakavgkv ipelngkltg mafrvptanv 241 svvdltcrle kpakyddikk vvkqasegpl kgilgytehq vvssdfnsdt hsstfdagag 301 ialndhfvkl iswydnefgy snrvvdlmah maske (SEQ ID NO:5)

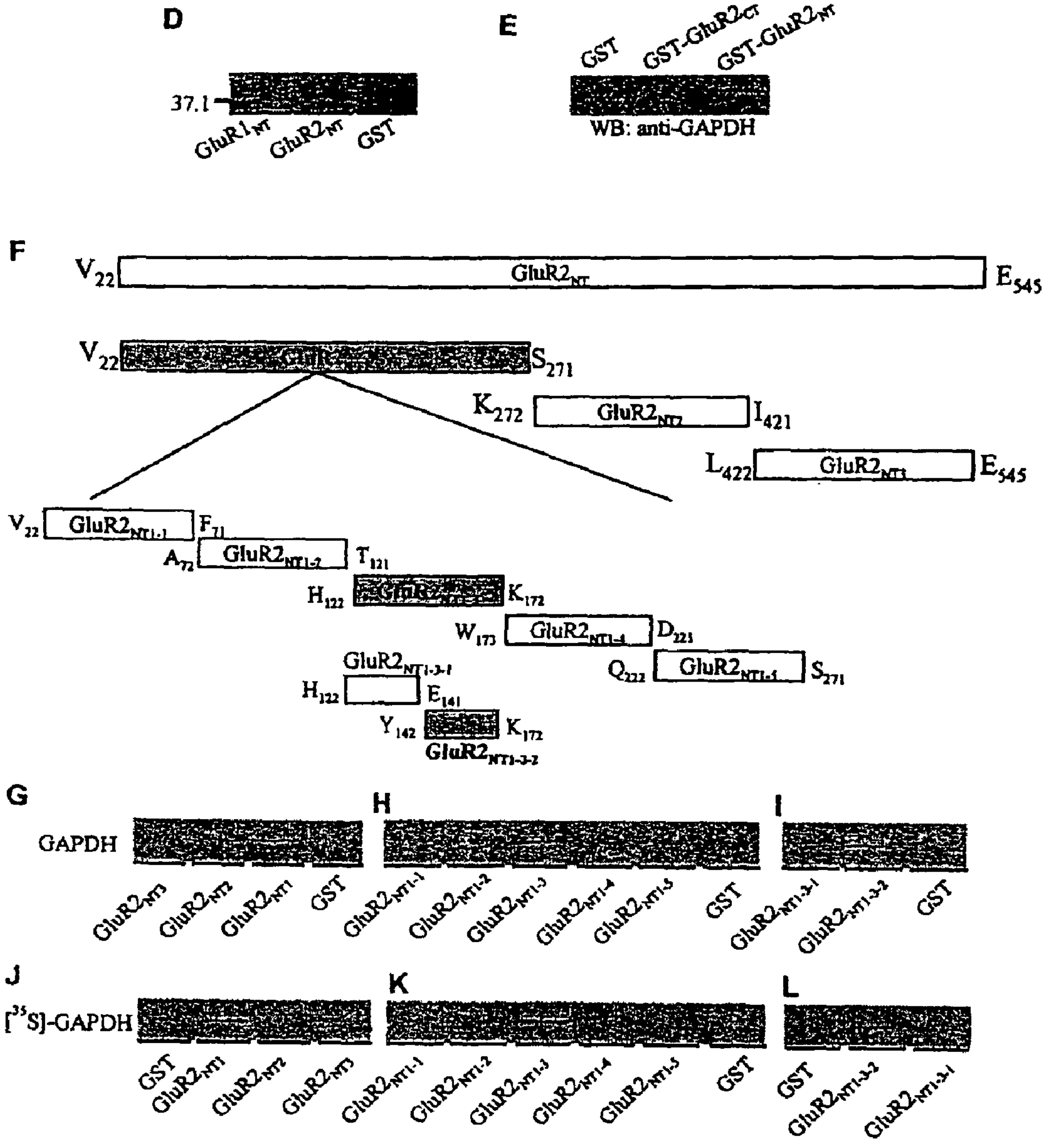
Figures 6D-L

<u>Neuronal Survival</u>
Sham: 100.0±4.4%
Ischemia: 12.7±2.4%
Peptide after ischemia: 25.9±7.8%
Peptide before ischemia : 30.9±11.9%

COMPOSITIONS AND METHODS FOR MODULATING AMPA RECEPTOR-MEDIATED EXCITOTOXICITY

FIELD OF INVENTION

The present invention relates to compositions and methods for modulating AMPA receptor-mediated excitotoxicity.

BACKGROUND OF THE INVENTION

Ischemic stroke is a worldwide public health problem and one of the leading causes of death in humans. A role for excitotoxicity-mediated by glutamate receptors has stimulated intensive research for decades. This has led to the hope that compounds antagonizing the glutamate receptor function may be of clinical benefit in treating stroke. However, the antagonist therapy failed in stroke trials, in most cases because of a limited therapeutic window and severe side effects, caused by the essential requirement of glutamate receptor-mediated excitatory neurotransmission in maintaining normal brain function.

Glutamate is the principal excitatory neurotransmitter in the brain and is involved in numerous physiological functions and processes including neuronal circuit development, learning and memory, as well as with many neuropathological disorders, such as the neurotoxicity associated with stroke. Glutamate activates two major subfamilies of ligand-gated postsynaptic receptors: AMPA (α-amino-3-hydroxyl-5-methyl-4-isoxazolepropionic acid) receptor and NMDA (N-methyl-D-aspartate) receptor (1). AMPA receptors mediate most of the excitatory postsynaptic current at resting membrane potentials while NMDA receptors are critically important in producing a number of different forms of synaptic plasticity in AMPA receptor-mediated synaptic transmission (2). Glutamate accumulation, in pathological condition such as immediately after ischemia, results in extensive stimulation of its receptors which can be highly neurotoxic (3,4). NMDA receptor-mediated neurotoxicity is dependent on extracellular Ca2+ and thus may reflect a large amount of Ca2+ influx directly through the receptor-gated ion channels (3,4). Most models of ischemic neurodegeneration have focused on the putative role of NMDA receptor activation. However, use of NMDA antagonists in animal models of ischemia as well as in human clinical trials has not generally shown the anticipated robust efficacy (5), suggesting NMDA receptor over activation may not be the sole player in the glutamate receptor-mediated neurotoxicity. AMPA receptors has been tightly associated with the selective pattern of neuronal loss in certain identifiable subsets of neurons observed in transient forebrain ischemic (6-13). However, as most AMPA receptor channels are much less Ca2+ permeable, the mechanism linking AMPA receptor activation to neuronal cell death remains largely unknown.

Functional changes in AMPA receptors are most often attributed to phosphorylation and de-phosphorylation by PKA (cyclic AMP-dependent protein kinase), protein kinase C (PKC) and CaM kinase II (calcium-calmodulin kinase II) (14-18). Recently, a variety of intracellular proteins have been reported to bind directly to AMPA receptors (19-23). These proteins play important roles not only in receptor targeting or clustering, but also in the modulation of receptor activity and activation of signaling pathways. One recent study reports that an extracellular secreted protein NARP binds to the extracellular N-terminus (NT) of AMPA receptors and plays a role in the induction of AMPA receptor clustering (24). This contrasts with all other identified AMPA interacting proteins that bind to the intracellular carboxyl tail (CT) of the AMPA receptor subunits.

Molecular Biology and Functions of GAPDH:

GAPDH is a tetrameric protein (144 kDa) composed of four identical subunits (37 kDa). The monomer is about 333-335 amino acids long, and each monomer has binding sites for the substrate (glyceraldehyde-3-phosphate, G-3-P) and co-factor nicotinamide adenine dinucleotide (NAD+) (25-26). Residues 0-149 from N-termini comprise the NAD+ binding domain; and, side chains involved in catalysis are contained in residues from 149-333 or 149-335. The co-factor binds reversibly to the enzyme prior to the substrate binding.

Traditionally, GAPDH has been considered the key enzyme in glycolysis, with a critical role in energy production. It is considered to be the product of a housekeeping gene whose transcript level remains constant under most of experimental conditions. However, recent evidence supports the notion that GAPDH plays a critical role in apoptosis during which its expression and subcellular localization is altered (27-30). The cellular localization of GAPDH is not only restricted to the cytosol but it is also found in the nucleus and plasma membrane.

In the nucleus, GAPDH has been shown to act as a DNA binding protein and t-RNA transport protein which plays a specific role in the transportation and maintenance of nucleic acid. GAPDH binds to and transports t-RNA from the nucleus to the cytosol, and the interaction of GAPDH with t-RNA is displaced by the co-factor, NAD+ (31-32). In addition, the uracil DNA glycosylase activity of GAPDH, together with its binding to diadenosine tetraphosphate (Ap4A), imply that nuclear GAPDH is involved in DNA replication and repair (33).

In the cytosol, RNA/GAPDH interactions enable GAPDH to play an important role in translational regulation of gene expression by controlling rate of protein synthesis and/or by altering the stability of mRNA (34-35). Furthermore, GAPDH is essential for ER to Golgi transport through its interaction with Rab2 GTPase and atypical protein kinase C/(aPKC/), two important proteins involved in the early secretory pathway and vesicle formation (36-38).

The function of membrane-associated GAPDH is to bind to tubulin thereby regulating polymerization and bundling of microtubules near the cell membrane, suggesting that GAPDH is involved in the re-organization of sub-cellular organelles (39). Furthermore, release of tubulin from membrane-associated GAPDH facilitates the fusion of vesicles to the plasma membrane (40). Thus, GAPDH is involved in both maintenance of membrane trafficking and the promotion of vesicle fusion through modulation of cytoskeleton functions.

GAPDH and Apoptosis:

GAPDH is overexpressed and accumulated in the nucleus during apoptosis induced by a variety of insults. Evidence shows that the GAPDH nuclear translocation is essential for the apoptotic cascade (41-42). Western blot analysis and confocal immunocytochemistry results indicate a significant increase of GAPDH expression in the nuclear fraction subjected to various stresses. Antisense oligonucleotides that deplete GAPDH prevent this nuclear translocation and reduce apoptosis (41, 43-44). The mechanism underlying GAPDH nuclear translocation and subsequent cell death remains largely unknown, however, recent studies have suggested several potential factors/pathways that maybe involved in the process: the expression of GAPDH is regulated by p53, the tumor suppressor protein and by proapoptotic transcription factor. Thus, GAPDH could be one of the downstream apoptotic mediators (45); over expression of bcl-2 blocks the apoptotic insults triggered by GAPDH over expression, nuclear translocation and subsequent apoptosis, suggesting that Bcl-2 may participate in the regulation of GAPDH nuclear translocation. This effect may be part of the mechanism of Bcl-2-induced protection against apoptosis (46) and GAPDH binds to a nuclear localization signal containing protein, Siah which initiates its translocation to the nucleus. The association with GAPDH stabilizes Siah and thereby enhances Siah-mediated proteolytic cleavage of its nuclear substrates, such as N—CoR and triggers apoptosis (44, 47-49).

Molecular Biology of AMPA Receptors:

AMPA receptors are intrinsic ion channels comprised of different subunits, which are encoded by four gene products, termed GluR1, 2, 3 and 4 (50-54). AMPA receptors are believed to exist as heteromeric assemblies of these subunits. Each subunit posses an extracellular NT domain, four putative transmembrane (TM) domains of which the second is believed to be a reentrant loop, as well as an intracellular CT domain (55-56). It is thought that the M2 loop participates in the formation of the ion channel pore. Two 150 amino-acid sequences (termed as S1 and S2) which are separated by the M1-M3 membrane domains appear to represent the agonist recognition sites (57). The molecular determinant of the calcium permeability is localized to the single amino acid in TM 2 region. A positively charged arginine (R) residue is found in position 586 for GluR2 whereas a neutral glutamine (Q) is found in the same position of GluR1, GluR3 and GluR4 subunits. Recombinant AMPA receptors lacking GluR2 show high calcium permeability and current-voltage relationships that doubly rectify (58). All four AMPA receptor subunits occur in two alternatively spliced versions, flip and flop. Flip differs flop version in the profile of desensitization and these variants show differing regional distributions which vary during development (59-60). The exact subunit composition of native AMPA receptors is not clear, but immunoprecipitation strategies have shown two major complexes composed of GluR2 together with either GluR1 or GluR3 in rat hippocampus (61). The presence of GluR2 subunit greatly reduces Ca++ and Zn++ permeability (58, 62-65) as well as the single channel conductance (66) of these receptors. Hence, most of AMPA receptors at the hippocampal synapses are Ca++ and Zn++-impermeable (62, 67-68).

AMPA receptor interacting proteins and their function: Using yeast a two-hybrid system with the CT domain of GluR2 subunit as bait, GRIP (Glutamate Receptor Interacting Protein, also known as AMPA receptor-binding protein, ABP) was the first protein identified as an AMPA receptor interacting protein (20). This finding was followed by extensive efforts to identify other AMPA receptor interacting proteins. Ban 4.1 and PKCγ interact with both GluR1 and GluR4 subunits (69-70); SAP97 (synapse-associated protein-97) couples only with GluR171; GRIP1, 2 and PICK1 (protein interacting with C kinase) bind to GluR3 and GluR4c (19,77). Also, three additional proteins, Stargazin, NARP (neuronal activity-regulated pentraxin), and AP2 (adaptor protein-2) bind to all of the AMPA receptor subunits (24, 72-73).

Interactions with the GluR2 subunit of AMPA receptors are of considerable interest due to the key biophysical properties conferred by the presence of this subunit. GRIP1, 2, PICK1, and NSF (N-ethylmaleimide-sensitive factor) are identified as GluR2 interacting proteins (20-21, 74-77). Two distinct interaction domains have been identified for the GluR2 C-terminus. NSF protein binds to a more proximal site (74,76), while the proteins GRIP1, ABP, and PICK1 associate with the PDZ-binding motif at the very distal end of the C-terminus (19-20, 76).

AMPA receptor interacting proteins may regulate these receptors in a variety of ways, such as altering AMPA receptor localization, clustering and/or trafficking. The binding of GluR2/3/4 to PICK1 is involved in the clustering of AMPA receptors (19,77), while the binding of GluR2/4 with NSF likely regulates rapid turnover of synaptic receptors (21, 74-75). Disruption of GluR2/3-GRIP interactions causes an increase in synaptic currents and prevents the generation of LTD22 and interaction with F— actin also plays a role in location of AMPA receptor clusters (78).

GluR2 subunit trafficking: Understanding the mechanism controlling surface expression of AMPA receptors in insult-vulnerable neurons is important because 98% of these receptors are localized at the synapse (hippocampus) (79-80) and the modulation of membrane receptor expression is an efficient mechanism for regulating the efficacy of synaptic transmission (80-98). AMPA receptors are trafficked between the plasma membrane and the intracellular compartments via delivery (insertion) and internalization (endocytosis) pathways. Native AMPA receptors undergo clathrin-dependent constitutive and regulated internalization involving adaptor protein-2 (AP2) and dynamin (99-100). Constitutive internalization counteracts constitutive receptor insertion, ensuring a constant number of cell surface AMPA receptors. Both receptor phosphorylation and GluR2 interacting proteins play an important role in trafficking of these receptors. Furthermore, NMDA receptor activity can regulated both AMPA receptor membrane insertion and internalization and this is important in certain forms of synaptic plasticity (100) as well as in NMDA-mediated neuronal apoptosis (101).

Glutamate mediated neurotoxicity is thought to contribute to neurodegeneration following a wide range of neurological insults including ischemia, trauma, hypoglycemia and epileptic seizure (3,4). It is believed that elevation of the extracellular glutamate after cerebral ischemia plays a critical role in the patho-physiological processes leading to death of ischemic brain tissue (102-103). Excessive glutamate, through an action on mainly on NMDA and AMPA glutamate receptors, facilitates Ca2+ influx, which under pathological conditions can result in excitotoxicity. The “calcium overload” hypothesis is the prominent theory explaining excitotoxicity (4). The molecular mechanisms underlying NMDA-mediated excitotoxicity involve many Ca2+-regulated processes in the cell including activation of proteases (104), endonucleases (105), nitric oxide synthase (106), the production of free radicals (107) and mitochondrial membrane permeability (108). The “calcium theory” can also apply to the Ca2+ permeable AMPA receptor-induced toxicity, however, there must be another explanation for the Ca2+-impermeable AMPA receptor induced toxicity. One possibility for Ca2+-impermeable AMPA receptor induced toxicity is to induce membrane depolarization via Na+ influx. The AMPA-mediated depolarization, in turn, opened both VSCCs and removed the Mg2+ block from NMDA receptors, thus allowing Ca2+ influx through these pathways (109-110). Another possibility is that AMPA receptor-mediated ion fluxes could be coupled to downstream neurotoxic second messengers via interactions with submembrane proteins. For example, the interaction of GRIP1 with GRASP-1 may couple AMPA receptors to Ras signaling (111) and GRASP-1 has been shown to be a neuronal substrate for caspase-3 (111) which is cleaved in apoptotic neurons in a time-dependent manner during development and ischemia (112). Furthermore, the potential role of GluR2-interacting proteins in excitotoxicity may be that the presence of GluR2 is required to maintain synaptic structure and organization. Accordingly, the toxicity observed in GluR2-deficient neurons may result from the effects on synaptic organization and function rather than due to AMPA receptor Ca2+ permeability. An interesting candidate protein is the NSF, as it has been shown both to interact with GluR2 and to mediate membrane-fusion events (113-115). Interestingly, NSF expression increases following an ischemic insult (116). It is not yet clear whether an increase in NSF leads to an increase of surface expression of existing GluR2-containing AMPA receptors following ischemia. If so, one may speculate that increased GluR2 surface expression may decrease Ca2+ permeability through AMPA receptors, and restore synaptic organization. Taken together, these activities indicate AMPA receptor interacting protein may play an important role in AMPA receptor-medited neurotoxicity.

The "GluR2 hypothesis" in AMPA receptor-mediated neurotoxicity (117-121) predicts that a relative reduction in the expression of GluR2 results in enhanced Ca2+-influx through newly synthesized AMPA receptors, thereby increasing neurotoxicity; and enhancing GluR2 membrane expression may provide protective effect based on the evidence showing that: (1) in ischemic CA1 neurons AMPA receptor-mediated EPSCs show an increased sensitivity to N-(4-hydroxyphenylpropanoyl)-spermine (NHPP-spermine) (122-123), a selective blocker for GluR2-lacking AMPA receptors (124-125). Indicative of a reduction in the number of GluR2 containing receptors; ischemic insults promote internalization of GluR2-containing AMPA receptors from synaptic sites and facilitate delivery of GluR2-lacking AMPA receptor (126); GluR2 expression is down regulated in vulnerable neurons in animal models of transient forebrain ischemia and epilepsy (127) and vulnerable CA1 pyramidal neurons can be rescued from forebrain ischemic injury by enhancing the expression of GluR2 containing receptors (127-128).

This evidence indicates the role of GluR2 membrane expression in the AMPA receptor-mediated neurotoxicity, which raise the possibility for proteins that regulate GluR2 subunit trafficking through protein-protein interaction with GluR2 to be involved in the AMPA receptor mediated apoptosis.

There is a need in the art for compositions and methods for modulating AMPA receptor-mediated excitotoxicity. There is also a need in the art for compositions and methods for modulating GAPDH association with GluR2 subunit or p53.

SUMMARY OF THE INVENTION

The present invention relates to compositions and methods for modulating AMPA receptor-mediated excitotoxicity.

According to the present invention there is provided an excitotoxicity-inhibiting polypeptide comprising an amino acid sequence that modulates Glu-R2-containing AMPA receptor signal transduction, wherein said polypeptide does not encompass a naturally occurring GluR2 subunit or GAPDH polypeptide.

Also provided by the present invention is an excitoxicity-inhibiting polypeptide as defined above, comprising an amino acid sequence selected from the group consisting of:

a) GluR2 NT1-3-2 (Y142-K172) amino acid sequence (SEQ ID NO:1), or a sequence which is at least 80% identical to SEQ ID NO:1 that binds to GAPDH and wherein said polypeptide does not encompass a naturally occurring full length GluR2 subunit polypeptide, and;

b) GAPDH(2-2-1-1) (I221-E250) amino acid sequence (SEQ ID NO:2), or a sequence which is at least 80% identical to SEQ ID NO:2 that binds to p53 and wherein said polypeptide does not encompass a naturally occurring full length GAPDH polypeptide.

Also provided by the present invention is an excitoxicity-inhibiting polypeptide as defined above, comprising the GluR2 NT1-3-2 (Y142-K172) amino acid sequence (SEQ ID NO:1).

Also provided by the present invention is an excitoxicity-inhibiting polypeptide as defined above, comprising the GAPDH(2-2-1-1) (I221-E250) amino acid sequence (SEQ ID NO:2).

Also provided by the present invention is an excitoxicity-inhibiting polypeptide as defined above, wherein the polypeptide is a fusion protein.

Also provided by the present invention is an excitoxicity-inhibiting polypeptide as defined above, wherein the fusion protein comprises a protein transduction domain.

Also provided by the present invention is an excitoxicity-inhibiting polypeptide as defined above, the polypeptide attached covalently or non-covalently to a non-protein substrate, non-protein molecule, non-protein macromolecule, a support, or any combination thereof. Further, the polypeptide, non-protein substrate, non-protein molecule, non-protein macromolecule, support or any combination thereof may be labeled.

The present invention also provides a nucleic acid encoding the excitotoxicity-inhibiting polypeptide as defined above.

The present invention also provides a method of inhibiting AMPA receptor-mediated excitotoxicity comprising, administering, a polypeptide comprising the GluR2 NT1-3-2 (Y142-K172) amino acid sequence (SEQ ID NO:1) or GAPDH (2-2-1-1) (I221-E250) amino acid sequence (SEQ ID NO:2)

or a nucleic acid capable of expressing a polypeptide comprising the GluR2 NT1-3-2 (Y142-K172) amino acid sequence (SEQ ID NO:1) or GAPDH(2-2-1-1) (I221-E250) amino acid sequence (SEQ ID NO:2), to a cell, tissue or subject in need thereof.

Also according to the present invention is a method as defined above wherein the wherein the method is practiced in a subject in vivo.

Also according to the present invention is a method as defined above, wherein the subject is a human subject. Further, the human subject may have or be at risk of stroke, epilepsy, traumatic brain injury, brain damage resulting from cardiac bypass surgery or a combination thereof.

Also provided by the present invention is a method of inhibiting GAPDH association with either the GluR2 subunit or p53 comprising administering a polypeptide comprising the GluR2 NT1-3-2 (Y142-K172) amino acid sequence (SEQ ID NO:1) or GAPDH(2-2-1-1) (I221-E250) amino acid sequence (SEQ ID NO:2), to a solution, cell, cell culture, tissue or subject comprising GAPDH and either GluR2 subunit or p53.

Also provided by the present invention is a method of treating or preventing brain injury associated with stroke, epilepsy, trauma, cardiac bypass surgery or a combination thereof comprising, administering, GluR2 NT1-3-2 (Y142-K172) amino acid sequence (SEQ ID NO:1) or GAPDH(2-2-1-1) (I221-E250) amino acid sequence (SEQ ID NO:2)

or a nucleic acid capable of expressing a polypeptide comprising the GluR2 NT1-3-2 (Y142-K172) amino acid sequence (SEQ ID NO:1) or GAPDH(2-2-1-1) (I221-E250) amino acid sequence (SEQ ID NO:2), to a subject in need thereof.

Also provided by the present invention is a kit comprising, a) a polypeptide comprising the GluR2 NT1-3-2 (Y142-K172) amino acid sequence (SEQ ID NO:1), b) a nucleic acid capable of expressing a polypeptide comprising the GluR2 NT1-3-2 (Y142-K172) amino acid sequence (SEQ ID NO:1), c) a polypeptide that comprises GAPDH (2-2-1-1) amino acid sequence (SEQ ID NO:2), d) a nucleic acid capable of expressing a polypeptide comprising the GAPDH (2-2-1-1) amino acid sequence (SEQ ID NO:2), e) one or more diluents, delivery vehicles, pharmaceutically acceptable excipients, or a combination thereof, f) one or more devices for delivering polypeptides or nucleic acids to a solution, cell, cell culture, tissue, organ or subject, g) instructions for using any component in the kit or practicing any method as described herein, or any combination or sub-combination thereof.

The present invention also provides a composition comprising the excitotoxicity-inhibiting polypeptide as defined above and one or more diluents, delivery vehicles, pharmaceutically acceptable excipients, or a combination thereof. Further, the composition may comprise polypeptides independently comprising SEQ ID NO:1 and SEQ ID NO:2. Also contemplated are compositions comprising one or more diluents, delivery vehicles, pharmaceutically acceptable excipients, or a combination thereof.

This summary of the invention does not necessarily describe all features of the invention.

BRIEF DESCRIPTION OF THE DRAWINGS

These and other features of the invention will become more apparent from the following description in which reference is made to the appended drawings wherein:

FIG. 1 shows nucleotide and amino acid sequences of polypeptides and nucleic as described herein. (A) shows the GluR2 NT1-3-2 (Y142-K172) amino acid sequence (SEQ ID NO:1). (B) shows the GAPDH(2-2-1-1) (I221-E250) amino acid sequence (SEQ ID NO:2). (C) shows a representative nucleotide sequence encoding a polypeptide that comprises the GluR2 NT1-3-2 (Y142-K172) amino acid sequence (SEQ ID NO:3). The shaded and underlined regions show a nucleotide sequence encoding residues Y142 to K172. (D) shows a polypeptide sequence of GluR2 comprising V22 to E545 (SEQ ID NO:4). The GluR2 NT1-3-2 (Y142-K172) amino acid sequence is underlined. (E) shows the amino acid sequence of GAPDH (SEQ ID NO:5) from *Homo sapiens*. The GAPDH(2-2-1-1) (I221-E250) sequence is underlined.

FIGS. 6(D-L) show identification and validation of the GluR2 region involved in the GAPDH-GluR2 interaction. (D), Coomassie blue stained SDS-PAGE gel of the protein selectively pulled down by GST-GluR$2_{NT}$, but not GluR$1_{NT}$ or GST alone from solubilized rat hippocampal lysate (20 μg GST peptide, 100 μg of hippocampal tissue). Positions of molecular size are shown. Protein of interest: ~37 kDa. (E) GAPDH was specifically pulled down by GST-GluR$2_{NT}$ (20 μg) in detergent extracts of rat hippocampus (100 μg), but not GST-GluR$2_{CT}$ or GST alone. (F) Schematic representation of GST-fusion proteins encoding GluR$2_{NT1}$ to GluR$2_{NT3}$, GluR$2_{NT1-1}$ to GluR$2_{NT1-5}$, GluR$2_{NT1-3-1}$ and GluR2 NT1-3-2. (G-I) Affinity purification of GAPDH from solubilized rat hippocampal tissue (100 μg amount) using 20 μg GST fusion peptides encoding truncated versions of GluR2. GAPDH was specifically pulled down by GST-GluR$2_{NT1}$ (G) GST-GluR$2_{NT1-3}$ (H) and GST-GluR2 NT1-3-2 (I) but not by the other GST fusion proteins or by GST alone. (J-L) Using an in vitro binding assay, [$^{35}$S]-GAPDH probe bound with specific GST-GluR$2_{NT1}$ (J), GST-GluR$2_{NT1-3}$ (K) and GST-GluR2 NT1-3-2 (L) fragments, but not with other GST fusion proteins or GST alone.

The intensity of protein bands were measured by Image J software and normalized to the corresponding control samples. (B) Schematic representation of $GluR2_{NT}$ mutants. GluR2-M1 94-95 KK->AA; GluR2-M2 171-172 KK->AA; GluR2-M3 187-188 KK->AA. (C) Both GAPDH and GluR2 nuclear expression was significantly decreased in GluR2-M2 transfected HEK293T cells upon glutamate treatment (100 μM, 30 min). (D) GluR2-M2 inhibited glutamate-induced cell death in AMPAR transfected HEK293T cells. **Significantly different from GluR2-WT group (n=9, P<0.01), ANOVA, followed by post-hoc Student-Newman-Keuls test. (E) GAPDH was immunoprecipitated by $GluR2_{NT}$ wild type and $GluR2_{NT}$ mutants. (F) GluR2 translocated mainly on nuclear envelope, while GAPDH translocated mainly into nucleoplasm after AMPA receptor activation. (G-H), CO—IP of GAPDH by GluR2 subunit (upper panel) and p53 (lower panel) in nuclear envelope and nucleoplasm of rat hippocampal neurons.

Figure 27:
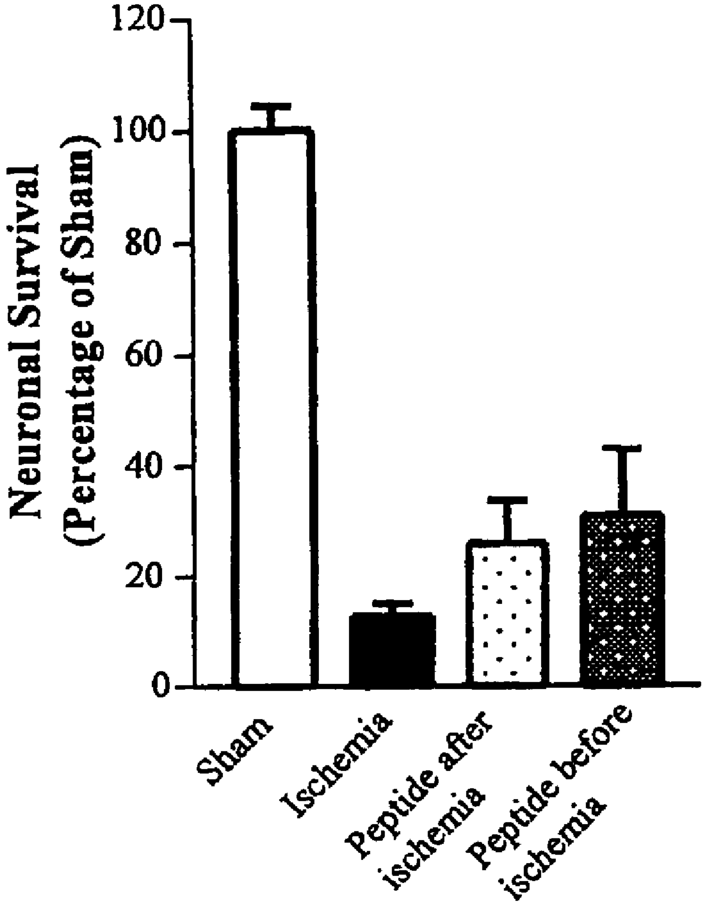

FIG. 27 shows results confirming neuroprotective activity of peptide GluR2 NT1-3-2 in ischemia model. Cresyl violet was used to stain alive neurons in hippocampus region of each animal. Total number of cresyl violet-stained nuclei in CA1 regions were summarized. Peptide treatment after ischemia rescued 13.2% neurons from cell death; while peptide treatment before ischemia rescued 18.2% neurons from cell death.

DETAILED DESCRIPTION

The present invention relates to compositions and methods for modulating AMPA receptor-mediated excitotoxicity.

The following description is of a preferred embodiment.

Overactivation of the α-amino-3-hydroxy-5-methylisoxazole-4-propionic acid subtype of glutamate receptors (AMPAR) leads to excitotoxic neuronal injuries seen in both acute brain insults including stroke and prolonged seizure activity, yet the underlying mechanisms remain poorly understood. Here we report that the GluR2-containing AMPAR form a complex with extracellular glyceraldehyde-3-phosphate dehydrogenase (GAPDH) through a direct protein-protein interaction between GAPDH and the amino-terminus of the GluR2 subunit. AMPAR activation facilitates the complex formation and results in rapid endocytosis-dependent translocation of the complex to the nucleus, whereby GAPDH dissociates from the AMPAR and binds to nuclear p53 and activates the p53-dependent cell death pathway. Disrupting either GAPDH-GluR2 or GAPDH-p53 interaction protects against AMPAR-induced cell death. Thus, our results reveal a previously unappreciated cellular signaling pathway underlying GluR2-containing AMPAR-dependent cell death and provide novel targets against which new therapeutics may be developed to combat diseases involving for example, but not limited to GluR2/AMPAR neurotoxicity.

According to the present invention, there is provided an excitotoxicity-inhibiting polypeptide comprising an amino acid sequence selected from the group consisting of:

a) GluR2 NT1-3-2 (Y142-K172) amino acid sequence (SEQ ID NO:1), or a sequence which is at least 80% identical to SEQ ID NO:1 that binds to GAPDH and wherein said polypeptide does not encompass a naturally occurring full length GluR2 subunit polypeptide, and;

b) GAPDH(2-2-1-1) (I221-E250) amino acid sequence (SEQ ID NO:2), or a sequence which is at least 80% identical to SEQ ID NO:2 that binds to p53 and wherein said polypeptide does not encompass a naturally occurring full length GAPDH polypeptide.

Without wishing to be bound by theory or limiting in any manner, the excitotoxicity-inhibiting polypeptides of the present invention interfere with normal GluR2 subunit AMPA receptor signal transduction activity, for example, but not limited to, by interacting with normal physiological protein binding partners required for normal signal transduction.

The present invention also contemplates excitotoxicity-inhibiting polypeptides consisting of:

a) GluR2 NT1-3-2 (Y142-K172) amino acid sequence (SEQ ID NO:1), or a sequence which is at least 80% identical to SEQ ID NO:1 that binds to GAPDH and wherein said polypeptide does not encompass a naturally occurring full length GluR2 subunit polypeptide, and;

b) GAPDH(2-2-1-1) (I221-E250) amino acid sequence (SEQ ID NO:2), or a sequence which is at least 80% identical to SEQ ID NO:2 that binds to p53 and wherein said polypeptide does not encompass a naturally occurring full length GAPDH polypeptide.

As provided above, variations of the polypeptide sequences of SEQ ID NO:1 and SEQ ID NO:2 are contemplated herein. For example, with respect to SEQ ID NO:1 (GluR2 NT1-3-2), but not to be considered limiting in any manner, one or more residues at positions 3, 5, 18, 21, 22, 23, 26 or 30 of SEQ ID NO:1 may be replaced by an alternate amino acid residue. For instance, but without wishing to be limiting, glutamine at position 3 may be replaced by another amino acid, for example, but not limited to lysine. Aspartic acid at position 5 may be replaced by another amino acid, for example, but not limited to threonine or glutamic acid. Serine at position 18 may be replaced by another amino acid, for example, but not limited to threonine. Glutamine at position 21 may be replaced by another amino acid, for example, but not limited to arginine. Alanine at position 22 may be replaced by another amino acid, for example, but not limited to valine or isoleucine. Valine at position 23 may be replaced by another amino acid, for example, but not limited to isoleucine. Serine at position 26 may be replaced by another amino acid, for example, but not limited to threonine. Lysine at position 30 may be replaced by another amino acid, for example, but not limited to arginine. Other modifications are also possible and are contemplated herein. Further, the present invention contemplates variations wherein one or more of the replacements noted above are present in the polypeptide.

Without wishing to be considered limiting in any manner, and in respect to SEQ ID NO:2 (GAPDH 2-2-1-1) the alanine residue at position 18 of SEQ ID NO:2 may be replaced by another amino acid, for example, but not limited to, proline or serine. The asparagine residue at position 5 may be replaced with another amino acid, for example, but not limited to aspartic acid. Other modifications are also possible and are contemplated herein. Further, the present invention contemplates polypeptides wherein one or more of the amino acid replacements noted above are present in the polypeptide.

Naturally occurring full length GluR2 and GAPDH polypeptides and the sequences thereof are known in the art. For example, a search of the National Center for Biotechnology Information using sequence information provided herein can be used to identify naturally occurring full length GluR2 and GAPDH protein sequences.

The present invention also provides a polypeptide comprising the GluR2 NT1-3-2 (Y142-K172) amino acid sequence (SEQ ID NO:1), that does not encompass a naturally occurring full length GluR2 subunit, but rather is between about 31 and 200 amino acids in length, for example, but not limited to 31, 32, 33, 34, 35, 40, 45, 50, 55, 60, 65, 70, 75, 80, 85, 90, 95, 100, 110, 120, 130, 140, 150, 160, 170, 180, 190, 200 or any number of amino acids therein between. The present invention also encompasses polypeptides comprising the GluR2 NT1-3-2 (Y142-K172) amino acid sequence (SEQ ID NO:1) that may be defined by a range of lengths of any two of the values provided above, or any values therein between. For example, but not to be limiting in any manner, the present invention provides a polypeptide comprising the GluR2 NT1-3-2 (Y142-K172) amino acid sequence (SEQ ID NO:1) that is between 31 and 100 amino acids in length.

The present invention also provides a polypeptide comprising the GAPDH(2-2-1-1) amino acid sequence (SEQ ID NO:2) that does not encompass a naturally occurring full length GAPDH protein, but rather is between about 30 and 334 amino acids in length, for example, but not limited to 31, 32, 33, 34, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 310, 220, 330, 331, 332, 333, 334, or any number of amino acids therein between. The present invention also encompasses polypeptides comprising the GAPDH(2-2-1-1) amino acid sequence (SEQ ID NO:2) that may be defined by a range of lengths of any two of the values provided above, or any values therein between. For example, but not to be limiting in any manner, the present invention provides a polypeptide comprising the GAPDH(2-2-1-1) amino acid sequence (SEQ ID NO:2) that is between 31 and 334 amino acids in length.

The present invention also contemplates polypeptides having an amino acid sequence that comprises between about 80% to 100% sequence identity, for example, but not limited to 80%, 81%, 82%, 83%, 84%, 85%, 86%, 87%, 88%, 89%, 90%, 91%, 92%, 93%, 94%, 95%, 96%, 97%, 98%, 99% or 100% identity to the amino acid sequences described above. Further, the polypeptides may be defined as comprising a range of sequence identities defined by any two of the values listed above.

The present invention also contemplates polypeptides that comprise fragments of GluR2 NT1-3-2 (Y142-K172) amino acid sequence (SEQ ID NO:1), for example 30, 29, 28, 27, 26, 25, 24, 23, 22, 21, 20, 19, 18, 17, 16, 15, 14, 13, 12, 11, 10, 9, 8, and 7 amino acids. Further, the present invention also contemplates fragments that exhibit at least about 80% identity, preferably 85%, 90%, 95%, 96%, 97%, 98%, 99% or 100% identity to the polypeptides described above. The present invention also contemplates polypeptides that comprise fragments of GAPDH(2-2-1-1), for example 29, 28, 27, 26, 25, 24, 23, 22, 21, 20, 19, 18, 17, 16, 15, 14, 13, 12, 11, 10, 9, 8, and 7 amino acids. The fragments may comprise N-terminal deletions, C-terminal deletions, internal deletions or any combination thereof.

It is also contemplated that the GluR2 NT1-3-2 (Y142-K172) amino acid sequence (SEQ ID NO:1) or the GAPDH (2-2-1-1) (I221-E250) amino acid sequence (SEQ ID NO:2) may comprise part of a fusion protein, for example, but not limited to a polypeptide that further comprises a heterologous polypeptide or protein, for example, a carrier protein, a protein transduction domain or the like. For example, but not wishing to be limiting in any manner, the polypeptide of the present invention may be fused to a protein transduction domain to facilitate transit across lipid bilayers or membranes, for example, but not limited to as described in U.S. Publication 2002/0142299, U.S. Pat. No. 5,804,604, U.S. Pat. No. 5,747,641, U.S. Pat. No. 5,674,980, U.S. Pat. No. 5,670,617, and U.S. Pat. No. 5,652,122; PCT publication WO01/15511, US Publication 2004/0209797, PCT Publication WO99/07728, US Publication 2003/0186890, all of which are herein incorporated by reference.

It is also contemplated that the polypeptide of the present invention may be attached either covalently or non-covalently to a non-protein substrate or molecule, for example, but not limited to polyethylene glycol (PEG), dextran or polydextran bead or the like, a support such as, but not limited to a multi-well plate, coverslip, array, micro-chip or the like. It is also contemplated that the polypeptide, non-protein substrate, molecule or any combination thereof may be labeled, for example with a purification tag, a radioactive or fluorescent group, enzyme or the like.

The present invention also provides nucleic acids encoding the polypeptides as described above. In an embodiment of the present invention which is not meant to be limiting, there is provided a nucleic acid encoding a polypeptide comprising the GluR2 NT1-3-2 (Y142-K172) amino acid sequence (SEQ ID NO:1) or GAPDH (2-2-2-1) amino acid sequence (SEQ ID NO:2) that does not encode a naturally occurring full length GluR2 subunit or GAPDH protein, respectively. More preferably, but not wishing to be limiting in any manner, the present invention provides a nucleic acid encoding a polypeptide of between 31 and 200 amino acids and comprises the GluR2 NT1-3-2 (Y142-K172) amino acid sequence (SEQ ID NO:1) or a polypeptide of between 30 and 334 amino acids comprising the GAPDH (2-2-1-1) amino acid sequence (SEQ ID NO:2).

The present invention also contemplates compositions comprising one or more of the polypeptides and/or nucleic acids of the present invention. The compositions may comprise one or more diluents, delivery vehicles, excipients, for example, but not limited to pharmaceutically acceptable excipients as would be known in the art, buffers, media, solvents, solutions, carriers or the like. Such components alone or in any combination may provide a dosage form for using or administering the polypeptides or nucleic acids of the present invention to a solution, cell, cell culture, tissue, organ or subject, for example, but not limited to a human subject.

To determine whether a nucleic acid exhibits identity with the sequences presented herein, oligonucleotide alignment algorithms may be used, for example, but not limited to a BLAST (GenBank URL: wwvv.ncbi.nlm.nih.gov/cgi-bin/BLAST/, using default parameters: Program: blastn; Database: nr; Expect 10; filter: default; Alignment: pairwise; Query genetic Codes: Standard (1)), BLAST2 (EMBL URL: http://www.embl-heidelberg.de/Services/index.html using default parameters: Matrix BLOSUM62; Filter: default, echofilter: on, Expect:10, cutoff: default; Strand: both; Descriptions: 50, Alignments: 50), or FASTA, search, using default parameters. Polypeptide alignment algorithms are also available, for example, without limitation, BLAST 2 Sequences (www.ncbi.nlm.nih.gov/blast/b12 seq/b12.html, using default parameters Program: blastp; Matrix: BLOSUM62; Open gap (11) and extension gap (1) penalties; gap x_dropoff: 50; Expect 10; Word size: 3; filter: default).

An alternative indication that two nucleic acid sequences are substantially identical is that the two sequences hybridize to each other under moderately stringent, or preferably stringent, conditions. Hybridization to filter-bound sequences under moderately stringent conditions may, for example, be performed in 0.5 M $NaHPO_4$, 7% sodium dodecyl sulfate (SDS), 1 mM EDTA at 65° C., and washing in 0.2×SSC/0.1% SDS at 42° C. for at least 1 hour (see Ausubel, et al. (eds), 1989, Current Protocols in Molecular Biology, Vol. 1, Green Publishing Associates, Inc., and John Wiley & Sons, Inc., New York, at p. 2.10.3). Alternatively, hybridization to filter-bound sequences under stringent conditions may, for example, be performed in 0.5 M $NaHPO_4$, 7% SDS, 1 mM EDTA at 65° C., and washing in 0.1×SSC/0.1% SDS at 68° C. for at least 1 hour (see Ausubel, et al. (eds), 1989, supra). Hybridization conditions may be modified in accordance with known methods depending on the sequence of interest (see Tijssen, 1993, Laboratory Techniques in Biochemistry and Molecular Biology—Hybridization with Nucleic Acid Probes, Part I, Chapter 2 "Overview of principles of hybridization and the strategy of nucleic acid probe assays", Elsevier, N.Y.). Generally, but not wishing to be limiting, stringent conditions are selected to be about 5° C. lower than the thermal melting point for the specific sequence at a defined ionic strength and pH.

A polypeptide of the invention can be synthesized in vitro or delivered to a cell in vivo by any conventional method. As a representative example of an in vitro method, the polypeptide may be chemically synthesized in vitro, or may be enzymatically synthesized in vitro in a suitable biological expression system. As a representative example of an in vivo method, a DNA, RNA, or DNA/RNA hybrid molecule comprising a nucleotide sequence encoding a polypeptide of the invention is introduced into an animal, and the nucleotide sequence is expressed within a cell of an animal.

The nucleotide sequence may be operably linked to regulatory elements in order to achieve preferential expression at desired times or in desired cell or tissue types. Furthermore, as will be known to one of skill in the art, other nucleotide sequences including, without limitation, 5' untranslated region, 3' untranslated regions, cap structure, poly A tail, translational initiators, sequences encoding signalling or targeting peptides, translational enhancers, transcriptional enhancers, translational terminators, transcriptional terminators, transcriptional promoters, may be operably linked with the nucleotide sequence encoding a polypeptide (see as a representative example "Genes VII", Lewin, B. Oxford University Press (2000) or "Molecular Cloning: A Laboratory Manual", Sambrook et al., Cold Spring Harbor Laboratory, 3rd edition (2001)). A nucleotide sequence encoding a polypeptide or a fusion polypeptide comprising the polypeptide may be incorporated into a suitable vector. Vectors may be commercially obtained from companies such as Stratagene or InVitrogen. Vectors can also be individually constructed or modified using standard molecular biology techniques, as outlined, for example, in Sambrook et al. (Cold Spring Harbor Laboratory, 3rd edition (2001)). A vector may contain any number of nucleotide sequences encoding desired elements that may be operably linked to a nucleotide sequence encoding a polypeptide or fusion polypeptide comprising a protein transduction domain. Such nucleotide sequences encoding desired elements, include, but are not limited to, transcriptional promoters, transcriptional enhancers, transcriptional terminators, translational initiators, translational terminators, ribosome binding sites, 5' untranslated region, 3' untranslated regions, cap structure, poly A tail, origin of replication, detectable markers, afffinity tags, signal or target peptide, Persons skilled in the art will recognize that the selection and/or construction of a suitable vector may depend upon several factors, including, without limitation, the size of the nucleic acid to be incorporated into the vector, the type of transcriptional and translational control elements desired, the level of expression desired, copy number desired, whether chromosomal integration is desired, the type of selection process that is desired, or the host cell or the host range that is intended to be transformed.

As described herein, and unless clearly indicated otherwise, the term "mini-gene" means the expression product of a nucleic acid or nucleotide sequence encoding and capable of expressing a polypeptide in a cell. For example, but not wishing to be considered limiting in any manner, a mini-gene includes a nucleic acid or nucleotide sequence encoding and capable of expressing the polypeptide comprising the GluR2 NT1-3-2 (Y142-K172) amino acid sequence (SEQ ID NO:1) in a cell. In an alternate embodiment, the mini-gene comprises a nucleic acid or nucleotide sequence encoding and capable of expressing the polypeptide comprising the GAPDH(2-2-1-1) (I221-E250) amino acid sequence (SEQ ID NO:2) in a cell.

The DNA, RNA, or DNA/RNA hybrid molecule may be introduced intracellularly, extracellularly into a cavity, interstitial space, into the circulation of an organism, orally, or by any other standard route of introduction for therapeutic molecules and/or pharmaceutical compositions. Standard physical methods of introducing nucleic acids include, but are not limited to, injection of a solution comprising RNA, DNA, or RNA/DNA hybrids, bombardment by particles covered by the nucleic acid, bathing a cell or organism in a solution of the nucleic acid, or electroporation of cell membranes in the presence of the nucleic acid.

A nucleic acid may be introduced into suitable eukaryotic cells ex vivo and the cells harbouring the nucleic acid can then be inserted into a desired location in an animal. A nucleic acid can also be used to transform prokaryotic cells, and the transformed prokaryotic cells can be introduced into an animal, for example, through an oral route. Those skilled in the art will recognize that a nucleic acid may be constructed in such a fashion that the transformed prokaryotic cells can express and secrete a polypeptide of the invention. Further, a nucleic acid may also be inserted into a viral vector and packaged into viral particles for efficient delivery and expression.

Dosage Forms

The polypeptides of the present invention or the nucleic acids encoding the polypeptides of the present invention may be formulated into any convenient dosage form as would be known in the art. The dosage form may comprise, but is not limited to an oral dosage form wherein the agent is dissolved, suspended or the like in a suitable excipient such as but not limited to water or saline. In addition, the agent may be formulated into a dosage form that could be applied topically or could be administered by inhaler, or by injection either subcutaneously, into organs, or into circulation. An injectable dosage form may include other carriers that may function to enhance the activity of the agent. Any suitable carrier known in the art may be used. Also, the agent may be formulated for use in the production of a medicament. Many methods for the productions of dosage forms, medicaments, or pharmaceutical compositions are well known in the art and can be readily applied to the present invention by persons skilled in the art.

According to the present invention there is also provided a method of inhibiting GluR2 subunit association with GAPDH comprising: administering a polypeptide comprising the GluR2 NT1-3-2 (Y142-K172) amino acid sequence (SEQ ID NO:1) to a solution, cell, cell culture, tissue or subject comprising GluR2 subunit and GAPDH. The method may be practiced in vitro or in vivo. In an embodiment wherein the method is practiced in vivo, the method may be practiced in a human subject. The human subject may have or be susceptible to stroke, epilepsy or other forms of brain injury.

The invention also provides a method of inhibiting GluR2 subunit association with GAPDH comprising: administering a nucleic acid capable of expressing a polypeptide comprising the GluR2 NT1-3-2 (Y142-K172) amino acid sequence (SEQ ID NO:1) to a cell, cell culture, tissue or subject comprising GluR2 subunit and GAPDH. In an embodiment wherein the method is practiced in vivo, the method may be practiced in a human subject. The human subject may have or be susceptible to stroke, epilepsy or other forms of brain injury, for example, but not limited to traumatic brain injury or injury from cardiac bypass surgery.

According to the present invention there is also provided a method of inhibiting GAPDH association with p53 comprising: administering a polypeptide comprising the GAPDH (2-2-1-1) amino acid sequence (SEQ ID NO:2) to a solution, cell, cell culture, tissue or subject comprising GAPDH and p53. The method may be practiced in vitro or in vivo. In an embodiment wherein the method is practiced in vivo, the method may be practiced in a human subject. The human subject may have or be susceptible to stroke, epilepsy or other forms of brain injury.

The invention also provides a method of inhibiting GAPDH association with p53 comprising: administering a nucleic acid capable of expressing a polypeptide comprising the GAPDH (2-2-1-1) amino acid sequence (SEQ ID NO:2) to a cell, cell culture, tissue or subject comprising GAPDH and p53. In an embodiment wherein the method is practiced in vivo, the method may be practiced in a human subject. The human subject may have or be susceptible to stroke, epilepsy or other forms of brain injury.

Also provided by the present invention is a method of inhibiting AMPA receptor mediated excitotoxicity comprising, Administering, a polypeptide comprising the GluR2 NT1-3-2 (Y142-K172) amino acid sequence (SEQ ID NO:1) or a polypeptide comprising the GAPDH (2-2-1-1) amino acid sequence (SEQ ID NO:2);

or a nucleic acid capable of expressing a polypeptide comprising the GluR2 NT1-3-2 (Y142-K172) amino acid sequence (SEQ ID NO:1), or a nucleic acid capable of expressing a polypeptide comprising the GAPDH (2-2-1-1) amino acid sequence (SEQ ID NO:2)

to a cell, tissue or subject in need thereof. Accordingly, the method may be practiced in vitro or in vivo. In respect of a method that is practiced in vivo, but without wishing to be limiting in any manner, the subject may have or be at risk of stroke, epilepsy, or other forms of brain injury.

In still a further embodiment of the present invention, which is not meant to be limiting in any manner, there is provided a method of treating or preventing brain injury comprising, administering a polypeptide comprising the GluR2 NT1-3-2 (Y142-K172) amino acid sequence (SEQ ID NO:1) or a polypeptide comprising the GAPDH (2-2-1-1) amino acid sequence (SEQ ID NO:2);

or a nucleic acid capable of expressing a polypeptide comprising the GluR2 NT1-3-2 (Y142-K172) amino acid sequence (SEQ ID NO:1), or a nucleic acid capable of expressing a polypeptide comprising the GAPDH (2-2-1-1) amino acid sequence (SEQ ID NO:2), to a subject in need thereof. As will be evident to a person of skill in the art, an embodiment that comprises administering a nucleic acid as described above, further comprises the step of expressing nucleic acid in the subject.

The present invention also contemplates a method as defined above wherein the polypeptide is administered prior to, during, after or both prior to and after an event that causes or may cause brain injury, for example, but not limited to stroke, epileptic seizure, brain damage resulting from cardiac bypass surgery or a combination thereof. For example, but not to be considered limiting in any manner, subjects diagnosed with epilepsy may be administered the polypeptide of the present invention at one or more intervals after being diagnosed with the condition, preferably prior to, during or after prolonged episodes of seizure.

In a preferred embodiment, the polypeptide or polypeptides of the present invention are administered immediately after, for example, but not limited to, about concurrently with an event that causes, or is capable of causing brain injury and about 24 hours thereafter, more preferably about 12 hours, still more preferably about 6 hours, still more preferably about 2 hours, more preferably 1 hour or less.

Also provided by the present invention is a kit that comprises: a) a polypeptide comprising the GluR2 NT1-3-2 (Y142-K172) amino acid sequence (SEQ ID NO:1), b) a nucleic acid capable of expressing a polypeptide comprising the GluR2 NT1-3-2 (Y142-K172) amino acid sequence (SEQ ID NO:1), c) a polypeptide that comprises GAPDH (2-2-1-1) amino acid sequence (SEQ ID NO:2), d) a nucleic acid capable of expressing a polypeptide comprising the GAPDH (2-{2-1-1) amino acid sequence (SEQ ID NO:2) e) one or more diluents, delivery vehicles, pharmaceutically acceptable excipients or a combination thereof, f) one or more devices for delivering polypeptides or nucleic acids to a solution, cell, cell culture, tissue, organ or subject, g) instructions for using any component in the kit or practicing any method as described herein, or any combination thereof. Further, the kit may comprise other components as would be known to a person of skill in the art.

The present invention will be further illustrated in the following examples.

EXAMPLES

Experimental Procedures

Primary Hippocampal Neuron Culture

Primary cultures from hippocampus were prepared from fetal Wistar rats (embryonic day 17-19) on $Cell^+$ (Sarstedt) culture dishes as previously described (73). The cultures were used for experiments on 12-15 d after plating. Hippocampal cultures were pretreated with GluR2 NT1-3-2 peptides before kainic acid treatment.

GST Fusion Proteins and Mini-Genes

To construct GST-fusion proteins and mini-genes expressing truncated $GluR2_{NT}$ and GAPDH, cDNA fragments were amplified by using PCR method with specific primers. Except where specified, all 5' and 3' oligonucleotides incorporated BamH1 site (GGATCC) and Xho1 sites (CTCGAG), respectively, to facilitate subcloning into vector pcDNA3 (for mini-gene construction) or into vector pGEX-4T3 (for GST-fusion protein construction). GST-fusion proteins were prepared from bacterial lysates as described by the manufacturer (Amersham). To confirm appropriate splice fusion and the absence of spurious PCR generated nucleotide errors, all constructs were resequenced.

Protein Affinity Purification, In Vitro Binding, Co-Immunoprecipitation and Western Blot Protein affinity purification, in vitro binding, co-immunoprecipitation and Western blot analyses were performed as previously described (73, 79). Antibodies used for immunoprecipitation, Western blots and cell surface ELISA assays included GAPDH (polyclonal from Abcam, monoclonal from Chemicon), GluR2 (Western blots: Chemicon; immunoprecipitation: Upstate), HA (monoclonal, Covance), α-tubulin (monoclonal, Sigma-Aldrich), LaminB1 (Zymed Laboratories).

Cell-ELISA Assays

Cell-ELISA assays (colorimetric assays) were done essentially as previously described (82). In brief the same density of HEK-293T cells transfected with cDNAs encoding various receptor constructs were treated with 100 μM glutamate or extracellular solution (ECS) before fixing in 4% (W/V) paraformaldehyde for 10 minutes in the absence (non-permeabilized conditions) or presence (permeabilized conditions) of 1% (V/V) Triton X-100. Cells were incubated in 1% (W/V) glycine for 10 minutes at 4° C. to recover from the fixing. Cells were then incubated with a monoclonal antibody against specific antibodies for the purpose of labeling the receptors or proteins on the cell surface under non-permeabilized conditions or the entire receptor pool under permeabilized conditions. After incubation with corresponding HRP-conjugated secondary antibodies (Sigma-Aldrich), the HRP substrate o-phenylenediamine (Sigma-Aldrich Co) was added to produce a color reaction that was stopped with the equal volume of 3N HCl. Fluorescence intensity in each well was measured with a plate reader (Victor3; PerkinElmer). The cell surface expression of HA-GluR2 after pre-treatment with glutamate was presented as the ratio of colorimetric readings under non-permeabilized conditions to those under permeabilized conditions, and then normalized to their respective control groups (pretreated with ECS). Afterwards, cells were scrapped from the dishes, and the protein concentration of each dish was measured. The results of cell surface expression of receptors or proteins were calibrated by the protein concentration of each well. Analysis was done using at least 9 separate wells in each group. Cell ELISA using primary hippocampal neurons was performed identically with assays using HEK-293T cells, with the exception that the anti-GluR2 antibody (MAB397; Chemicon) was used as primary antibody instead of anti-HA.

Quantification of AMPA-Mediated Excitotoxicity

An equal density of HEK-293T cells transfected with AMPAR was exposed to 300 μM glutamate/25 μM cyclothiazide at 37° C. for 24 hour. Cells were allowed to recover for 24 hours at 37° C. To quantify AMPA-mediated cell death, culture medium was replaced by extracellular solution containing 50 μg/ml of propidium iodide (PI) (Invitrogen). After 30 minutes incubation at 37° C., fluorescence intensity in each well was measured with a plate reader (Victor3; PerkinElmer). The fraction of dead cells was normalized to the cell toxicity that occurred in either the glutamate treated cells or KA treated neurons. Primary hippocampal neurons were exposed to 100 μM KA/25 μM cyclothiazide in medium at 37° C. for 1 hour, at 37° C.

Cell Biotinylation

Cell biotinylation was essentially performed as described previously (76, 83). Briefly, for cell surface biotinylation, cells were rinsed four times with ice-cold PBS containing 0.1 mM $CaCl_2$ and 1.0 mM $MgCl_2$ ($PBS^{2+}$) after treatment, and incubated twice with 1.0 mg/ml sulfo-NHS-LC-biotin (Pierce, Rockford, Ill.) for 20 minutes at 4 degree. Non-reactive biotin was quenched with twice with 20 minute's incubation at 4 degree in ice-cold $PBS^{2+}$ and 0.1 M glycine. Cells were solubilized in RIPA buffer (10 mM Tris, Ph7.4, 150 mM NaCl, 1.0 mM EDTA, 0.1% (W/V) SDS, 1.0% (V/V) Trition X-100 and 1.0% (V/V) Sodium deoxycholate) containing protease inhibitors (1.0 mM PMSF and 1.0 μg/ml protease cocktail). Biotinylated and non-biotinylated proteins were separated from equal amounts of cellular protein by incubation with 50 μl of 50% slurry of immobilized streptavidin-conjugated beads (Pierce, Rockford, Ill.) for overnight with constant mixing at 4 degree. Unbound proteins (supernatant) were saved for later co-immunoprecipitation experiment. Proteins bound to streptavidin beads were eluted in biotin elution buffer. Biotinylated and non-biotinylated samples were applied to protein A/G PLUS-agarose (Santa Cruz) for co-immunoprecipitation. For nuclear biotinylated proteins, cells were firstly incubated with 1.0 mg/ml sulfo-NHS—SS-biotin (Pierce, Rockford, Ill.) before treatment. Afterwards cells were treated with 50 mM glutathione to cleave all cell surface biotin and nuclei were extracted from cell lysates. After incubation with immunopure immobilized streptavidin-conjugated beads (Pierce, Rockford, Ill.), beads were washed four times with RIPA buffer. The bead pellets were boiled in sample buffer and subjected to Western blot analysis.

Purification of Nuclei

Nuclei isolation was prepared as described previously (55, 66). Briefly, cells were gently rinsed twice with ice-cold PBS. And scraped in 1 ml of solution 1 (10 mM Tris-HCl, pH7.4, 100 mM NaCl2, 2.5 mM MgCl2, 0.5% NP-40, proteinase inhibitor and PMSF) per 10-cm plate. Then cells were homogenized by four passages through a 25-gauge needle and spin at 3000 g briefly. Pellets containing nuclei were subsequently utilized in biochemical assays.

Example 1

GAPDH Interacts with the Amino-Terminus of the GluR2 Subunit

To identify proteins that might possibly interact with N-terminus (NT) of AMPA receptor GluR1 and GluR2 subunits, we incubated rat hippocampal extracts with GST-fusion proteins: GST-GluR1NT (A19-E538), GST-GluR2NT (V22-E545), and GST alone, respectively. Then samples were subjected onto 10% SDS-PAGE and stained with Coomassie blue R250. A single immunoreactive band with an apparent molecular mass of ~37 kDa was enriched in GST-GluR2NT precipitated sample but not in that of GST-GluR1NT or GST alone. We excised the ~37 kDa band from the gel and used mass spectrometry to identify the protein. The most significant score for this band was obtained with GAPDH (Table 1).

TABLE 1

Protein Analysis Results
Database: NCBInr (2314886 sequences; 787107140 residues)
Taxonomy: Mammalia (mammals) (340771 sequences)

| Protein | AC | Mass | Score | Peptide Matched | Taxonomy |
|---|---|---|---|---|---|
| Glyceraldehyde 3-phosphate-dehydrogenase | gi\|56188 | 36103 | 128 | 3 | *Rattus norvegicus* |

Matched Peptides

| Mr(expt) | Mr(calc) | Score | peptide |
|---|---|---|---|
| 2245.13 | 2244.09 | 15 | VIISAPSADAPMFVMGVNHEK (SEQ ID NO: 6) |
| 2611.92 | 2610.35 | 63 | VIHDNFGIVEGLMTTVHAITATQK (SEQ ID NO: 7) |

-continued

| Mr(expt) | Mr(calc) | Score | peptide |
|---|---|---|---|
| 1557.75 | 1556.79 | 50 | VPTPNVSVVDLTCR (SEQ ID NO: 8) |

Sequence Coverage: 17%

(SEQ ID NO: 9)

```
1   MVKVGVNGFG RIGRLVTRAA FSCDKVDIVA INDPFIDLNY MVYMFQYDST
51  HGKFNGTVKA ENGKLVINGK PITIFQERDP VKIKWGDAGA EYVVESTGVF
101 TTMEKAGAHL KGGAKRVIIS APSADAPMFV MGVNHEKYDN SLKIVSNASC
151 TTNCLAPLAK VIHDNFGIVE GLMTTVHAIT ATQKTVDGPS GKLWRDGRGA
201 AQNIIPASTG AAKAVGKVIP ELNGKLTGMA FRVPTPNVSV VDLTCRLEKP
251 AKYDDIKKVV KQAAEGPLKG ILGYTEDQVV SCDFNSNSHS STFDAGAGIA
301 LNDNIVKLIS WYDNEYGYSN RVVDLMAYMA SKE
```

Example 2

Figure 4:
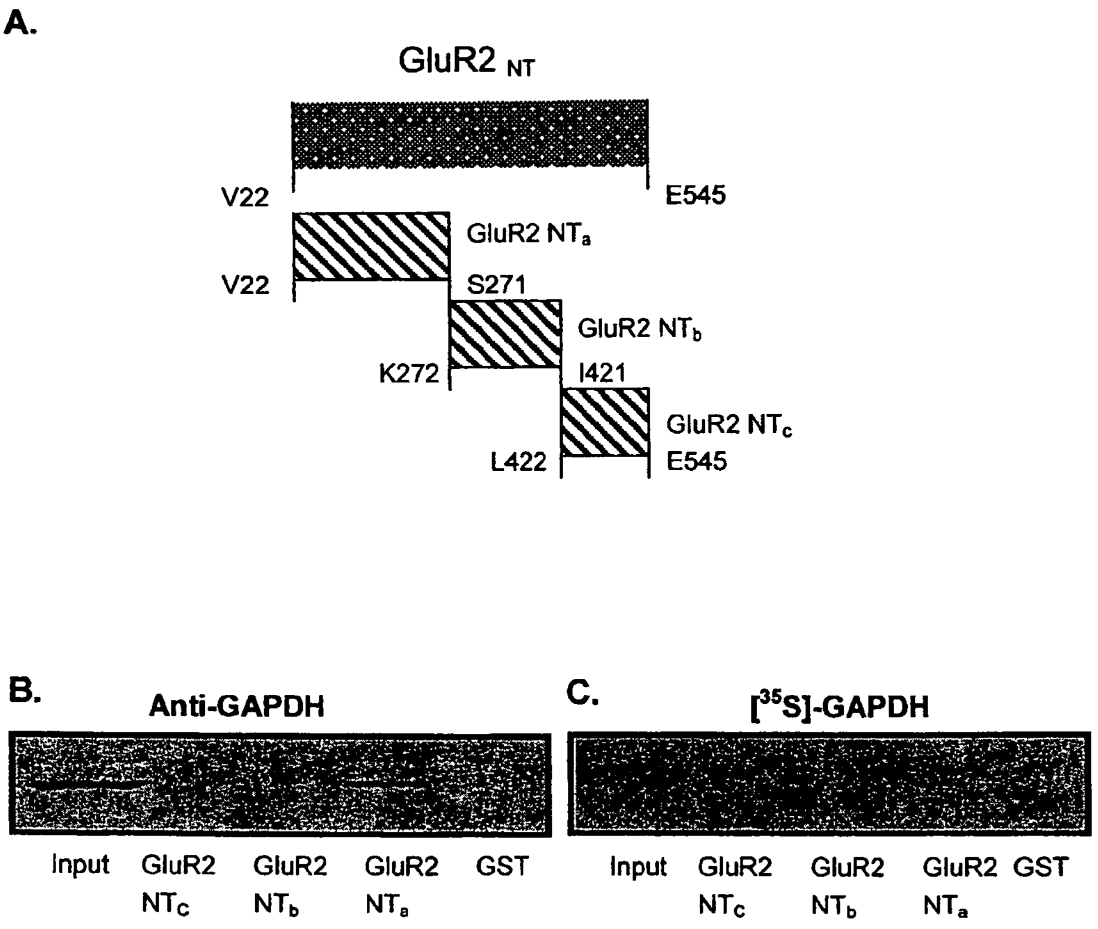
FIG. 4 shows identification of the GluR2 subunit region involved in the GAPDH and GluR2 NT interaction. (A) Schematic representation of the generated GluR2 NTa; GluR2 NTb; GluR2 NTc mini-genes. (B) Western blotting of GAPDH from solubilized rat hippocampal extracts showed the presence of GAPDH after affinity precipitation by GST-GluR2 NTa, but not by GST-GluR2 NTb, GST-GluR2 NTc or GST alone. (C) The [35S]-GAPDH probe bound with GST-GluR2 NTa, but not with GluR2 NTb, GluR2 NTc or GST alone in vitro binding assay.

Identification of Interaction Sites of the GAPDH and the GluR2 Subunit Complex In order to delineate the region of the GluR2NT involved in the interaction with the GAPDH, three GluR2NT GST-fusion proteins [GluR2 NTa V22-S271, (250 a.a), GluR2 NTb K272-421, (150 a.a), GluR2 NTc L422-E545, (124 a.a)] were constructed (FIG. 4A). In affinity purification assays, GluR2 NTa, but not GluR2 NTb, GluR2 NTc or GST alone precipitated GAPDH in rat hippocampal brain extract (FIG. 4B). Although these results demonstrated the presence of a GAPDH and GluR2 NT complex, it could not determine whether the complex was formed through a direct or indirect interaction. To clarify the nature of the interaction, blot overlay experiments were performed, which provided in vitro evidence for a direct interaction. GluR2 NTa, GluR2 NTb and GluR2 NTc were probed with in vitro translated [35S]-methionine labelled peptides encoding GAPDH ([35S]-GAPDH). The [35S]-GAPDH probe bound with GluR2 NTa, but not GluR2 NTb or GluR2 NTc. The binding of [35S]-GAPDH was specific, as it did not bind with GST (FIG. 4C).

Figure 5:
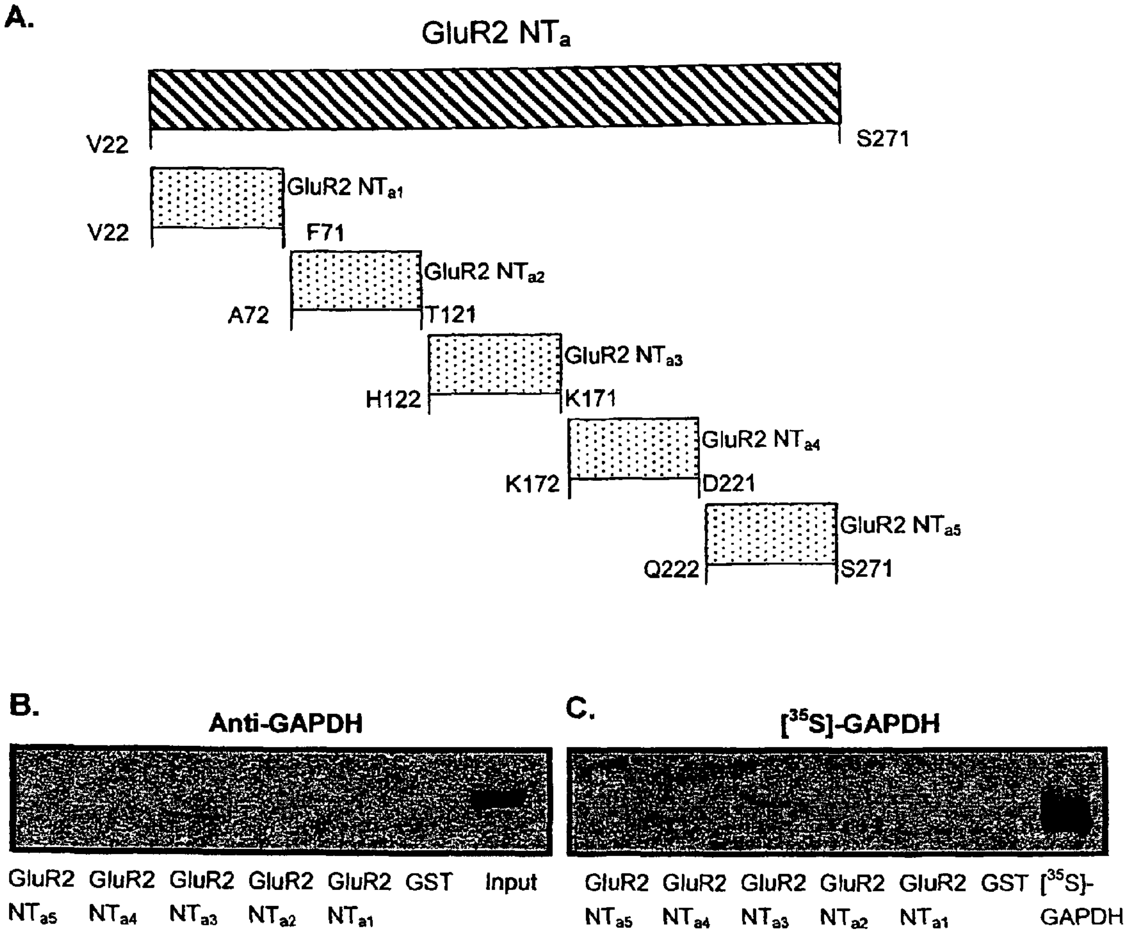
FIG. 5 shows identification of the GluR2 subunit region involved in the GAPDH and GluR2 NT interaction. (A) Schematic representation of the generated GluR2 NTa1; GluR2 NTa2; GluR2 NTa3; GluR2 NTa4 and GluR2 NTa5 mini-genes. (B) Western blotting of GAPDH from solubilized rat hippocampal extracts showed the presence of GAPDH after affinity precipitation by GST-GluR2 NTa3, but not by others or GST alone. (C) [35S]-GAPDH probe bound with GST-GluR2 NTa3, but not with others or GST alone In vitro binding assay.

In order to further delineate the region of GluR2 NTa involved in the interaction with GAPDH, the GluR2 NTa region was further divided into five GST-fusion proteins that were composed of 50 amino acids each (NTa1: V22-F71, GluR2 NTa2: A72-T121, GluR2 NTa3: H122-K171, GluR2 NTa4: K172-D221, GluR2 NTa5: Q222-S271) (FIG. 5A). In affinity purification assays, GluR2 NTa3, but not the other sub-regions or GST alone, precipitated GAPDH in rat hippocampal extracts (FIG. 5B). This was supported by a blot overlay experiment (FIG. 5C). Here the [35S]-GAPDH probe bound with GluR2 NTa3, but not to any of the other constructs.

We then further divided the GluR2 NTa3 region into 30 amino acids GST-fusion proteins and mini-genes (GluR2 NTa3-1: H122-E141, 20 a.a; GluR2 NT1-3-2 Y142-K172, 30 a.a) to delineate the region of GluR2 NTa3 involved in the interactions (FIG. 6A). GluR2 NT1-3-2, but not GluR2 NTa3-1 or GST alone, precipitated GAPDH in rat hippocampal extracts in affinity purification assays (FIG. 6B). This was also supported by a blot overlay experiment where [35S]-GAPDH probe bound with GluR2 NT1-3-2, but not GluR2 NTa3-1 or GST alone (FIG. 6C).

Figure 2:
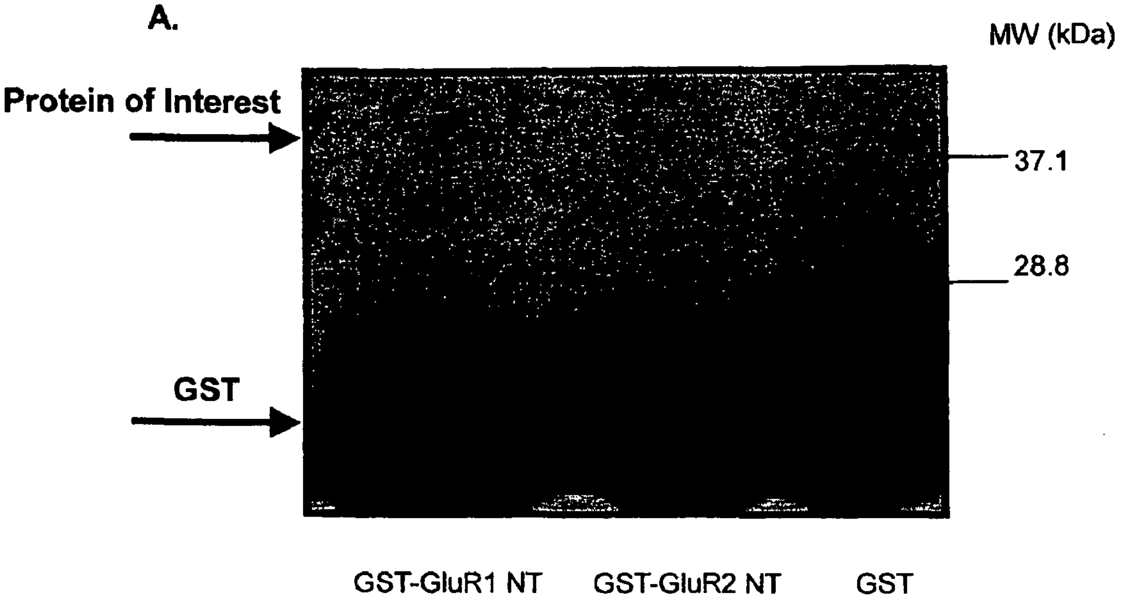
FIG. 2 shows Coomassie blue stained SDS-PAGE gel of the protein selectively pulled down by GST-GluR2NT. Positions of molecular size are shown. Protein of interest: ~37 kDa.
Figure 3:
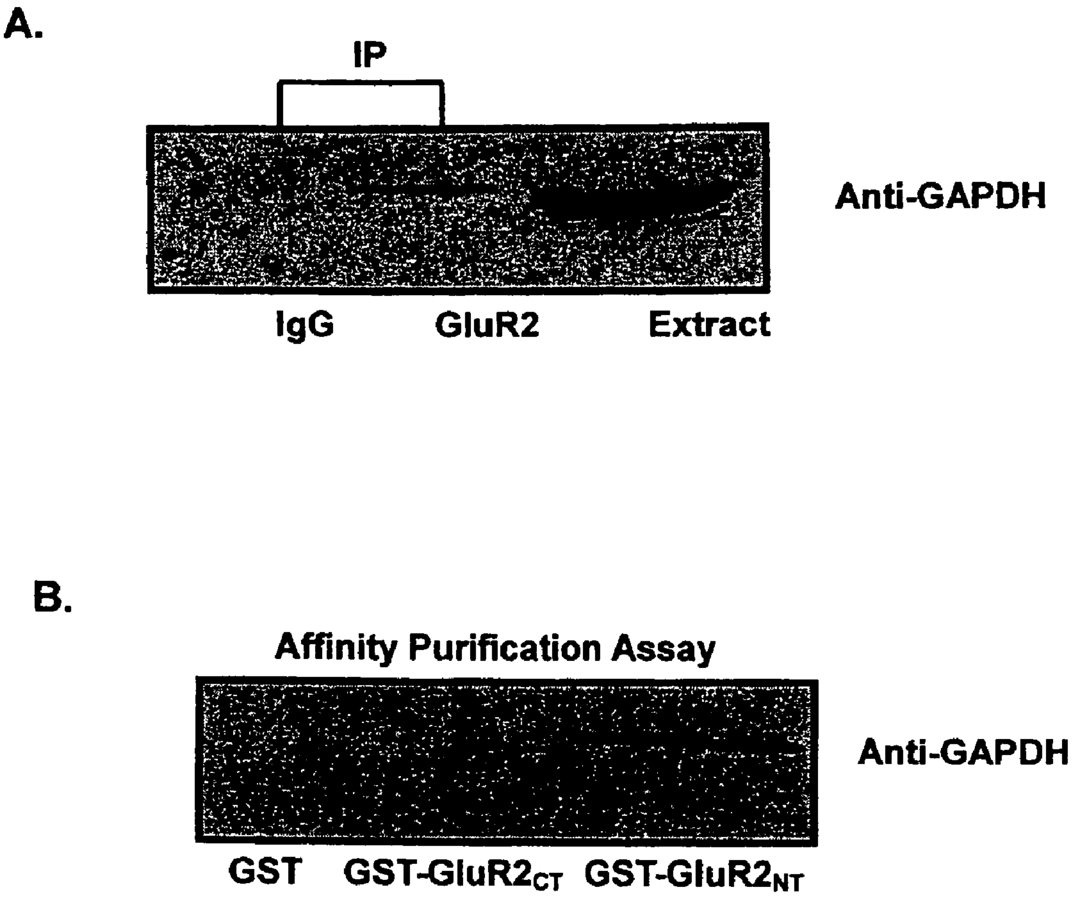
FIG. 3 shows biochemical association of the GluR2 subunit with GAPDH. (A) Coimmunoprecipitation of GAPDH from solubilized rat hippocampal lysates by GluR2 subunit (antibody). (B) Detergent extracts of rat hippocampus were incubated with GST-fusion proteins of GluR2CT or GluR2NT coupled to Glutathione-Sepharose beads for affinity purification. The eluted bound proteins were loaded on 10% SDS-PAGE gel and immunoblotted with primary antibody anti-GAPDH. IP, Immunoprecipitation.

In order to confirm the existence of GAPDH and GluR2NT complexes, we examined if GAPDH could CO—IP with GluR2 subunit in rat hippocampal extracts. The GAPDH antibody precipitated GluR2 subunit suggesting a physical interaction between GAPDH and GluR2 subunit (FIG. 3A).

Next we performed the protein affinity purification assays to further confirm whether the N-terminus or the C-terminus of GluR2 subunit was involved in the formation of complex. GST-GluR2NT, but not GST-GluR2CT or GST alone, precipitated GAPDH (FIG. 3B).

GAPDH and AMPAR Form a Direct Protein-Protein Through the GluR2 Amino-Terminus

In an attempt to validate potential protein regions that interact with the GluR2 subunit, we repeated experiments using GST-GluR2$_{NT}$ ($V_{22}$-$E_{545}$) to affinity "pull down" proteins from solubilized rat hippocampal tissues, using GST alone and GST-GluR1$_{NT}$ ($A_{19}$-$E_{538}$) as controls. The precipitated proteins were then identified by Coomassie brilliant blue staining after SDS-PAGE. A prominent protein band of ~40 kD was specifically precipitated by GST-GluR2$_{NT}$, but not by GST alone or GST-GluR1$_{NT}$ (FIG. 6D). These results suggested that the GluR2 subunit may form a protein complex with GAPDH through the GluR2$_{NT}$. We then confirmed this GluR2$_{NT}$-GAPDH putative interaction through pull-down/affinity purification experiments using GST-GluR2$_{NT}$, GST-GluR2$_{CT}$ ($I_{833}$-$I_{883}$) and GST alone. Subsequent Western blot analysis using a GAPDH antibody confirmed an association between GluR2$_{NT}$ and GAPDH (FIG. 6E).

Figure 6:
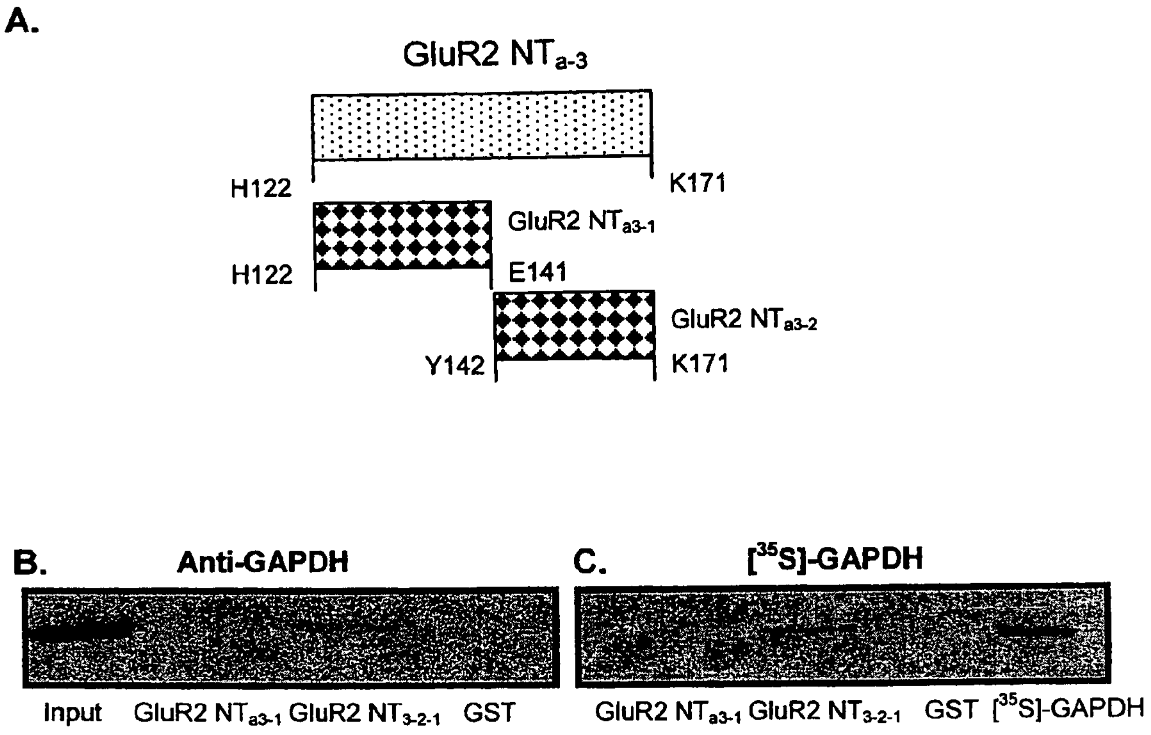
FIGS. 6 (A-C) show identification of the GluR2 subunit region involved in the GAPDH and GluR2NT interaction. (A) Schematic representation of the generated GluR2 NTa3-1 and GluR2 NT1-3-2 mini-genes. (B) Western blotting of GAPDH from solubilized rat hippocampal extracts showed the presence of GAPDH after affinity precipitation by GST-GluR2 NT1-3-2, but not by GST-GluR2 NTa3-1 or GST alone. (C) [35S]-GAPDH probe bound with GST-GluR2 NT1-3-2, but not with GST-GluR2 NTa3-1 or GST alone in vitro binding assay.

In order to confirm previous results and to delineate the region(s) of the GluR2$_{NT}$ involved in the interaction with GAPDH, three GluR2$_{NT}$ GST-fusion proteins (GluR2$_{NT1}$: $V_{22}$-$S_{271}$, GluR2$_{NT2}$: $K_{272}$-$I_{421}$, GluR2$_{NT3}$: $L_{422}$-$E_{545}$) were constructed (FIG. 6F) and utilized in affinity purification assays. As shown in FIG. 6J, only GST-GluR2$_{NT1}$ precipitated GAPDH indicating that the GluR2 subunit could interact with GAPDH through its NT region $V_{22}$-$S_{271}$. We then created a series of truncations of the GluR2$_{NT1}$ region to map the site that interacted with GAPDH. As shown in FIGS. 6K and 6L, only GST-GluR2$_{NT1-3}$ ($H_{122}$-$K_{172}$) and GST-GluR2 NT1-3-2 ($Y_{142}$-$K_{172}$) were able to precipitate GAPDH from rat hippocampal tissue. While these results demonstrated the presence of the GAPDH: AMPAR protein complex in rat hippocampal tissue, they did not clarify whether the GAPDH: AMPAR protein complex was formed through a direct interaction between GAPDH and AMPAR or was an indirect interaction facilitated by an accessory binding protein. In vitro binding assays provided evidence that GAPDH and the GluR2 subunit could directly interact with each other. As shown in FIG. 6, in vitro translated [$^{35}$S]-GAPDH probe hybridized with GST-GluR2$_{NT1}$ but not GST-GluR2$_{NT2}$, $GST\text{-}GluR2_{NT3}$ or GST alone, indicating the specificity of the direct protein-protein interaction between GAPDH and $GluR2_{NT1}$. Consistent with our affinity purification experiments, in vitro translated [$^{35}S$]-GAPDH probe only hybridized with $GST\text{-}GluR2_{NT1\text{-}3}$ and GST-GluR2 NT1-3-2, (FIG. 6K, L). These data suggested that GAPDH was involved in a direct protein-protein interaction with the GluR2 subunit through the Y142-K172 region of the $GluR2_{NT}$.

Example 3

Agonist Regulation of GluR2NT-GAPDH Protein-Protein Interactions

Before investigating whether the direct protein-protein interaction between GAPDH and GluR2 NT have functional implications, we tested if AMPA receptor activation affected the observed interactions. Based on previous reports, we focused on the GluR1/GluR2 AMPA receptor combination, one of the two most common AMPA receptor subunit combinations in the hippocampus, which have important defined roles in AMPA receptor trafficking and synaptic plasticity.

Figure 7:
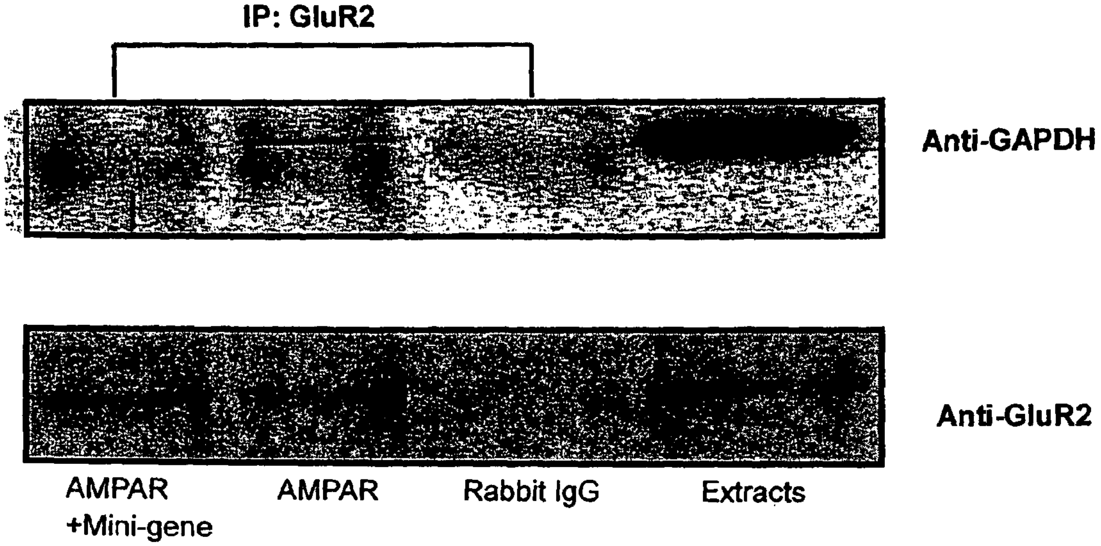
FIG. 7 shows association of the GluR2 subunit with GAPDH in transfected HEK 293T cells. GAPDH co-immunoprecipitated the GluR2 subunit revealing that these proteins associate without exogenous AMPA receptor agonist stimulation. The insertion of GluR2 NT1-3-2 mini-gene interrupted the protein-protein interaction. The directly immunoprecipitated GluR2 subunit was used as a loading control. Rabbit IgG and rat hippocampal extracts were used as negative control and positive control, respectively. IP, Immunoprecipitation.

We co-expressed both GluR1 and GluR2 along in the presence or absence of the GluR2 NT1-3-2 mini-gene in HEK293T cells. It should be noted that HEK293T cells expresses endogenous GAPDH. The GluR2 subunit and GAPDH could associate without exogenous AMPA receptor agonist stimulation (FIG. 7). The insertion of mini-gene greatly interrupted the protein-protein interaction.

Figure 8:
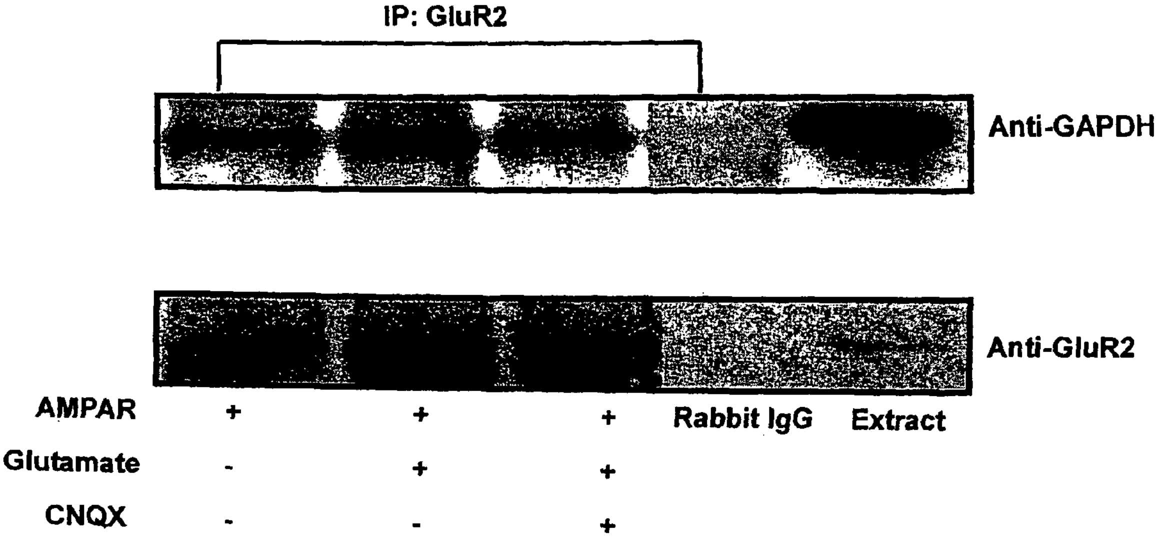
FIG. 8 shows activity-dependent association of the GluR2 subunit with GAPDH in transfected HEK 293T cells. Application of glutamate enhanced the protein-protein interaction, which was blocked by the competitive AMPA receptor antagonist CNQX. The directly immunoprecipitated GluR2 subunit was used as a loading control. Rabbit IgG and rat hippocampal extracts were used as negative control and positive control, respectively. IP, Immunoprecipitation.
Figure 9:
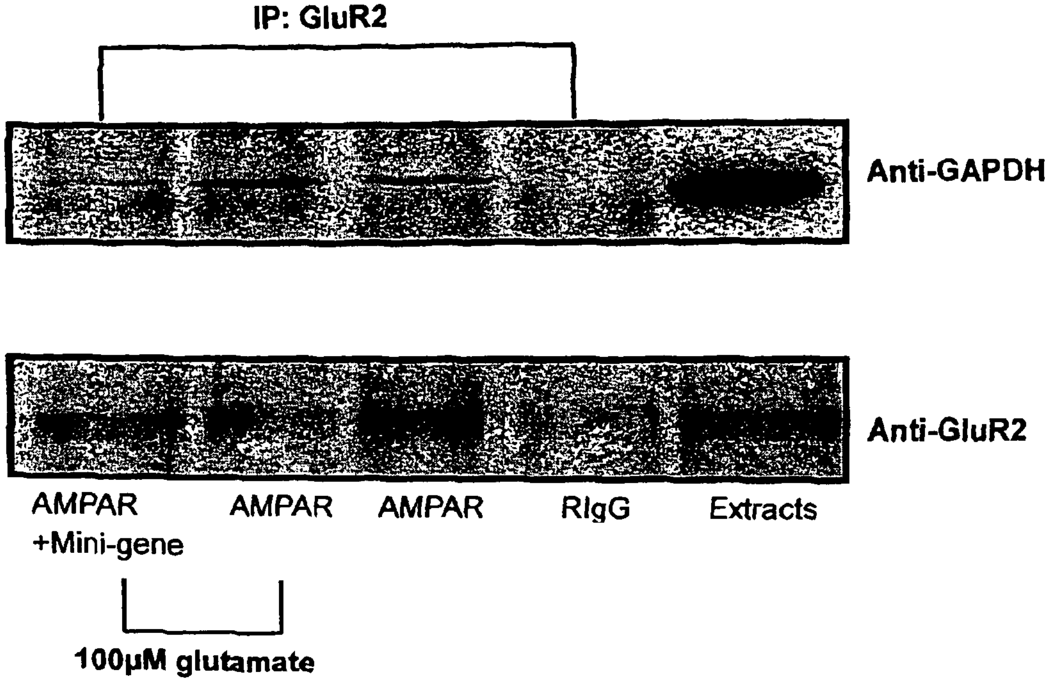
FIG. 9 shows association of the GluR2 subunit with GAPDH in transfected HEK 293T cells. GAPDH and GluR2 were co-immunoprecipitated from transfected HEK 293T cells lysates in the presence or absence of the GluR2 NT1-3-2 mini-gene, as well as with and without glutamate treatment. The directly immunoprecipitated GluR2 subunit was used as a loading control. Rabbit IgG and rat hippocampal extracts were used as negative control and positive control, respectively. RIgG, Rabbit IgG. IP, Immunoprecipitation.
Figure 10:
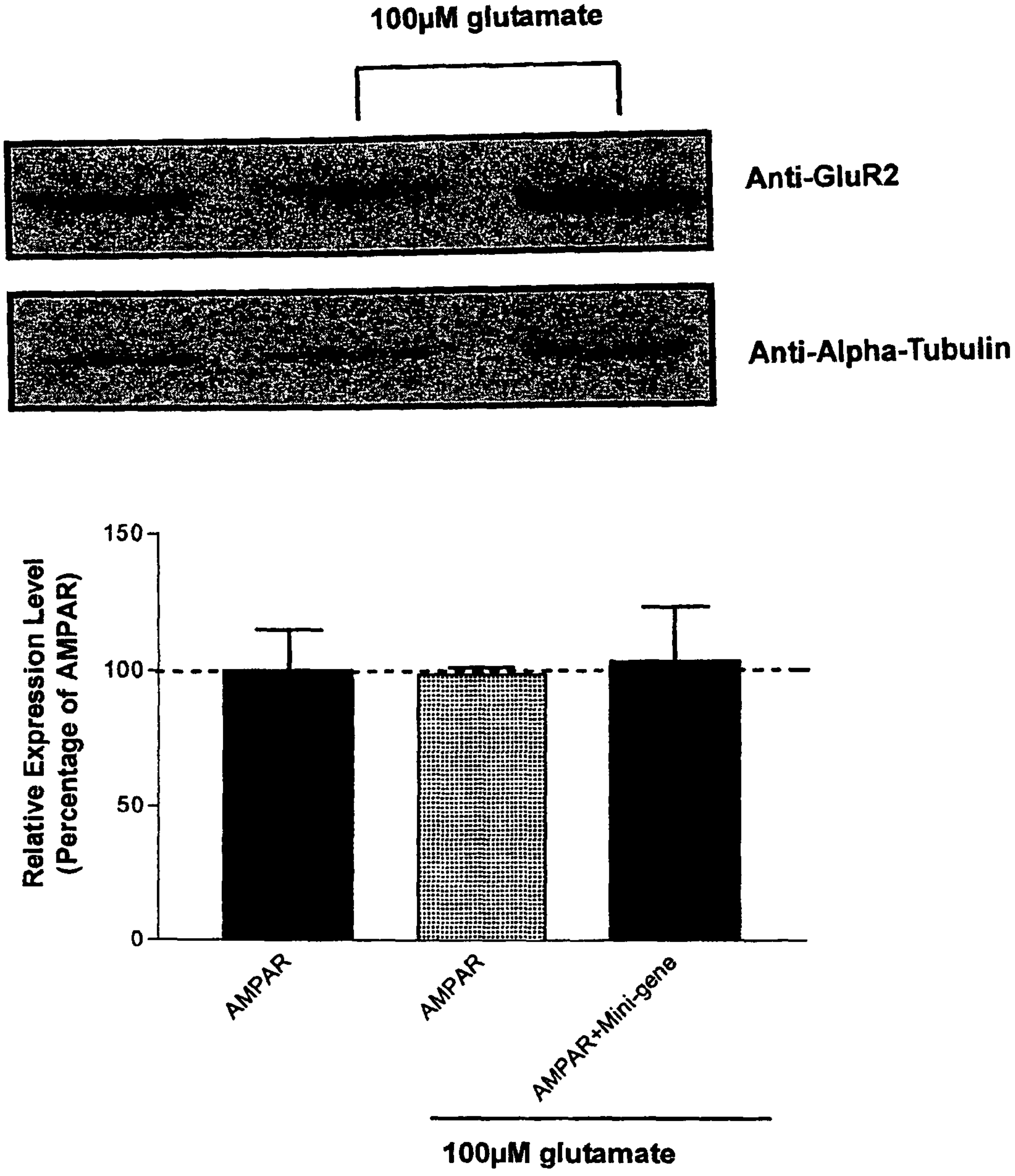
FIG. 10 shows Western blot analysis of the initial level of GluR2 subunit in transfected HEK293T cells, with and without 100 μM glutamate treatment. The total amount of proteins loaded was indicated by a cytoskeletal protein α-tubulin. The intensity of each protein band was quantified by densitometry (Software: Image J from research Services Branch). Data were representative of three independent experiments.
Figure 11:
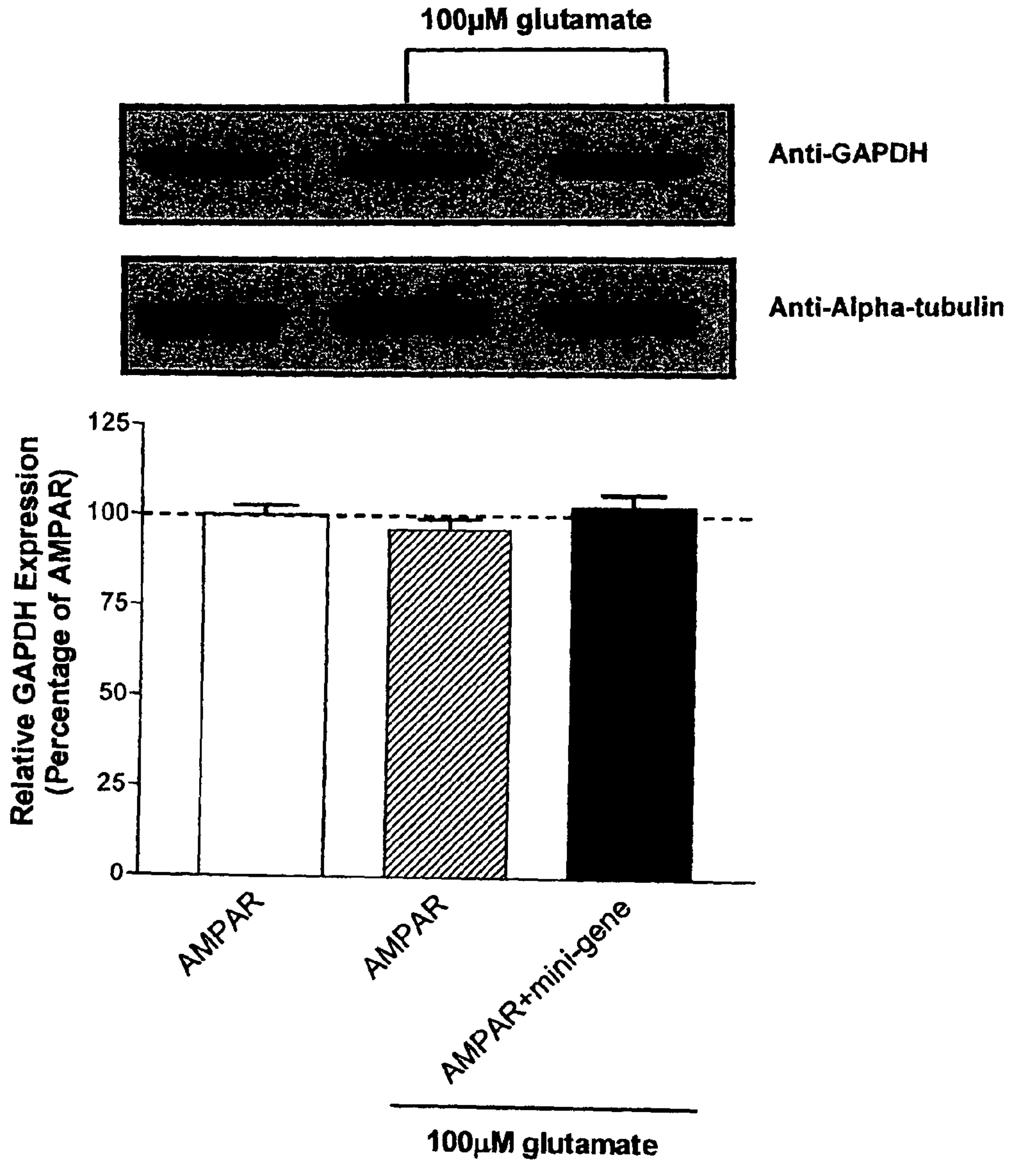
FIG. 11 shows the expression level of GAPDH in transfected HEK293T cells, with or without 100 μM glutamate treatment. The loading amount of proteins is indicated by cytoskeleton protein alpha-tubulin. The intensity of each protein band was quantified by densitometry (Software: ImageJ from research Services Branch). Data were representative of three independent experiments.

Activation of AMPA receptor with the agonist glutamate resulted in an increase in the CO—IP of GAPDH by the GluR2 subunit antibody (FIG. 8). The association between GAPDH and GluR2 was decreased by the application of 6-cyano-7-nitroquinoxaline-2,3-dione (CNQX), a competitive AMPA receptor antagonist used to block the AMPA receptor activation (FIG. 8). While the insertion of the GluR2 NT1-3-2 mini-gene was able to interrupt the protein-protein interaction either with or without glutamate treatment (FIG. 7, 9). In all immunoprecipitation experiments, the level of directly immunoprecipitated GluR2 subunit was used as a loading control (FIG. 7-9). Glutamate stimulation did not significantly alter the initial levels of solubilized protein GluR2 subunit (FIG. 10) or GAPDH (FIG. 11).

Example 4

Translocation of the GluR2 Subunit and GAPDH

The association of the GluR2 subunit with GAPDH increased after the glutamate treatment, and the expression level of GAPDH and GluR2 subunit changed little in the whole cell protein, accordingly, the expression level of these proteins in different cell compartments was tested.

Figure 12:
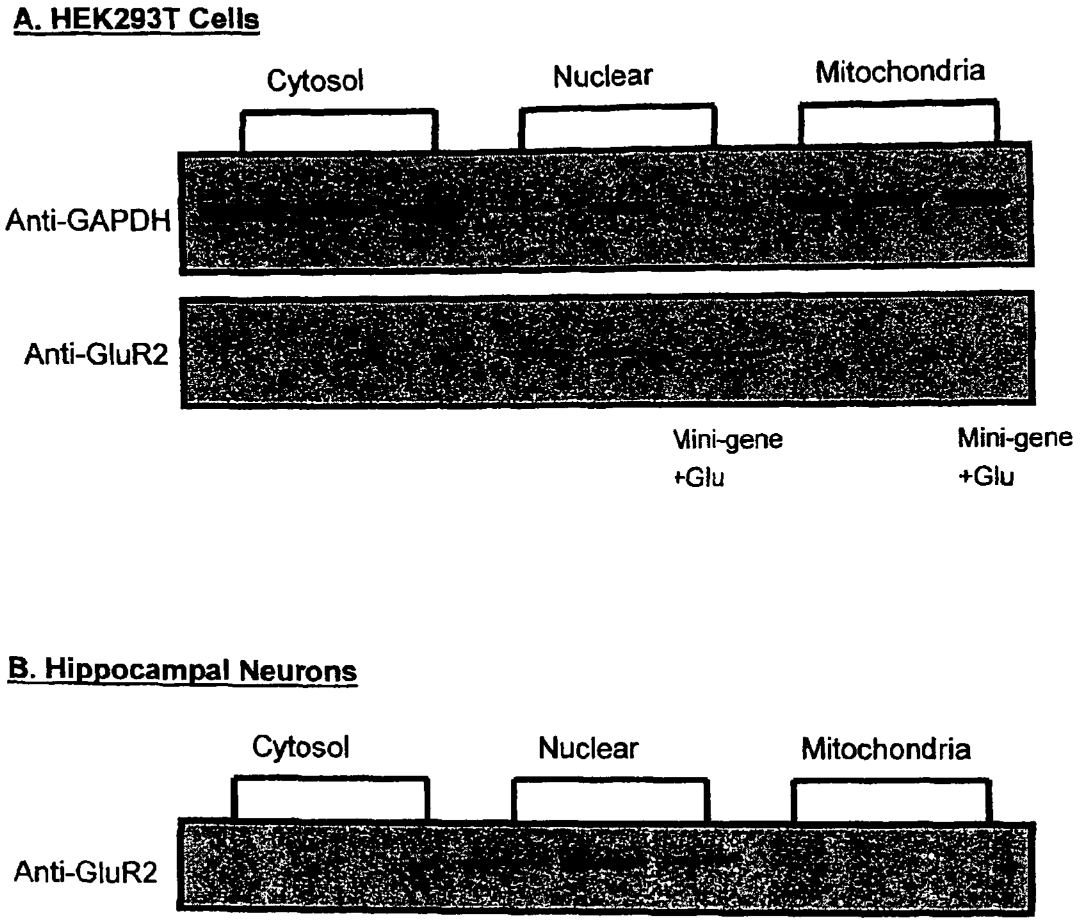
FIG. 12 shows the expression level of the GluR2 subunit and GAPDH in different cell compartments in the presence or absence of the GluR2 NT1-3-2 mini-gene. (A) 100 μM glutamate treatment facilitated the translocation of GAPDH, while the insertion of the GluR2 NT1-3-2 mini-gene reversed the increase. (B) 100 μM KA treatment increased the expression of the GluR2 subunit, while the insertion of the GluR2 NT1-3-2 mini-gene diminished this increase. Data were representative of three independent experiments.

We extracted different cell compartments of transfected HEK 293T cells, such as cytosol, nucleus and mitochondria. Glutamate treatment (100 μM) facilitated GAPDH translocation from the cytosol and mitochondria to the nucleus. The insertion of the GluR2 NT1-3-2 mini-gene was able to interrupt the GAPDH translocation triggered by glutamate treatment (FIG. 12). The expression level of the GluR2 subunit increased in the nucleus after the glutamate treatment, while the insertion of the GluR2 NT1-3-2 mini-gene also diminished this increase (FIG. 12).

We also examined the translocation of GAPDH and the GluR2 subunit in hippocampal neuron cultures. Because neurons have other glutamate receptors such as the NMDA receptor, we used the AMPA receptor-selective agonist KA (100 μM) other than glutamate. The TAT-GluR2 NT1-3-2 peptide (10 μM) was applied for 30 minutes before KA treatment. The expression level of the GluR2 subunit increased in the nucleus after KA treatment, while intracellular application of GluR2 NT1-3-2 peptide reversed this increase (FIG. 12).

Example 5

Functional Characterization of the GAPDH and GluR2 Interaction —Modulation of GluR2 Cell Surface Expression Through the GAPDH and GluR2 Interaction Modification of ligand-gated receptor function at the postsynaptic domain is one of the most important mechanisms by which the efficacy of synaptic transmission in the nervous system is regulated. Traditionally, these types of modifications have been achieved mainly by altering the channel-gating properties or conductance of the receptors. However, recent evidence suggests that AMPA receptors are continuously recycled between the plasma membrane and the intracellular compartments via vesicle-mediated plasma membrane insertion and clathrin-dependent endocytosis. Regulation of either receptor insertion or endocytosis results a rapid change in the population of these receptors expressed on the plasma membrane surface and in the receptor-mediated responses. Therefore, the regulation plays an important role in mediating certain forms of synaptic plasticity. In order to investigate whether the population of AMPA receptors on the plasma membrane can be regulated by the GAPDH and GluR2 NT complex, we scanned transiently transfected HEK293T cells and hippocampal neurons expressing AMPA receptors by cell ELISA. The oxygen-glucose deprivation (OGD) model was also applied.

Figure 13:
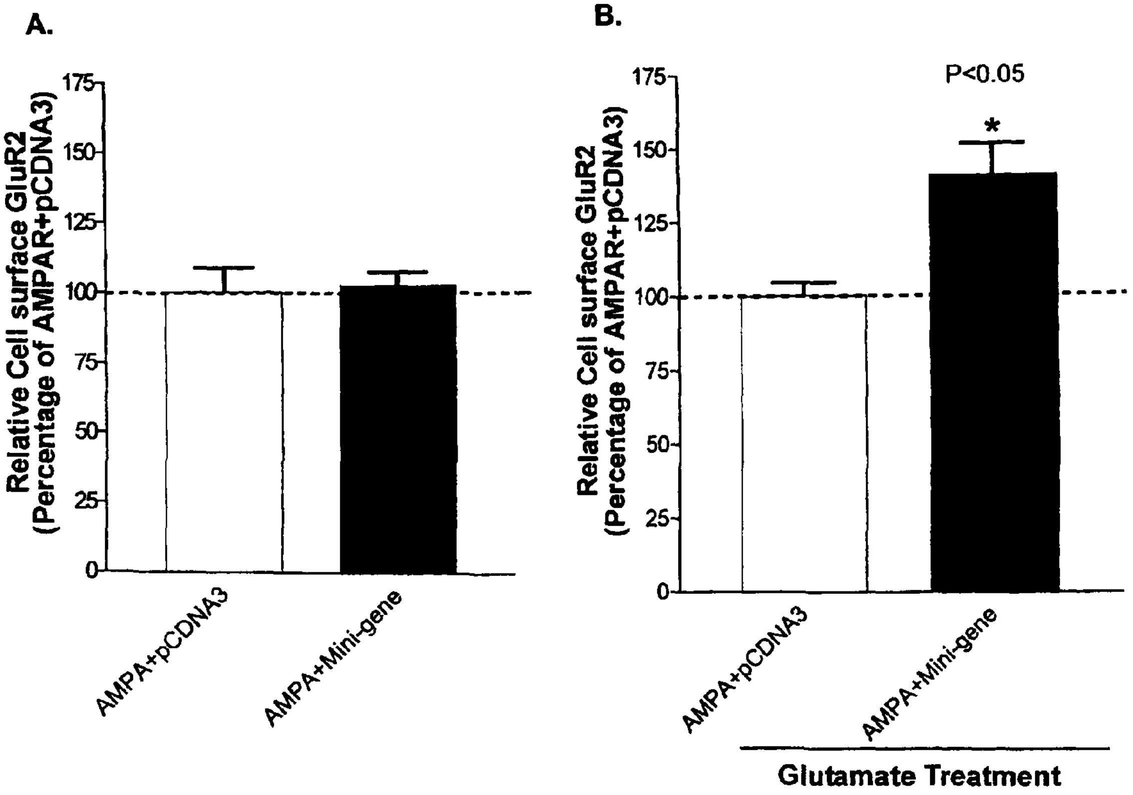
FIG. 13 shows interruption of the GAPDH and GluR2 interaction resulted in an increase in the GluR2 subunit cell surface expression following glutamate treatment in HEK-293T cells. (A) The interruption of GAPDH and GluR2 interaction using the GluR2 NT1-3-2 mini-gene had no significant effect on the GluR2 cell surface expression in the absence of glutamate. (B) Interruption OF the interaction with the GluR2 NT1-3-2 mini-gene showed a significant increase in cell surface GluR2 expression after 100 μM glutamate treatment for 30 minutes. The asterisk indicates a significant difference from the AMPA+pCDNA3 group ($p<0.05$; $n=9$).

In HEK293T cells coexpressing both GluR1 and GluR2 subunits of AMPA receptors, the insertion of GluR2 NT1-3-2 mini-gene did not change the number of GluR2 subunit on plasma membrane (FIG. 13). However, after treatment with glutamate (100 μM) for 30 minutes, the plasma membrane expression of GluR2 subunits significantly increased in GluR2 NT1-3-2 insertion group, compared to the mini-gene sham-transfected group (FIG. 13).

Figure 14:
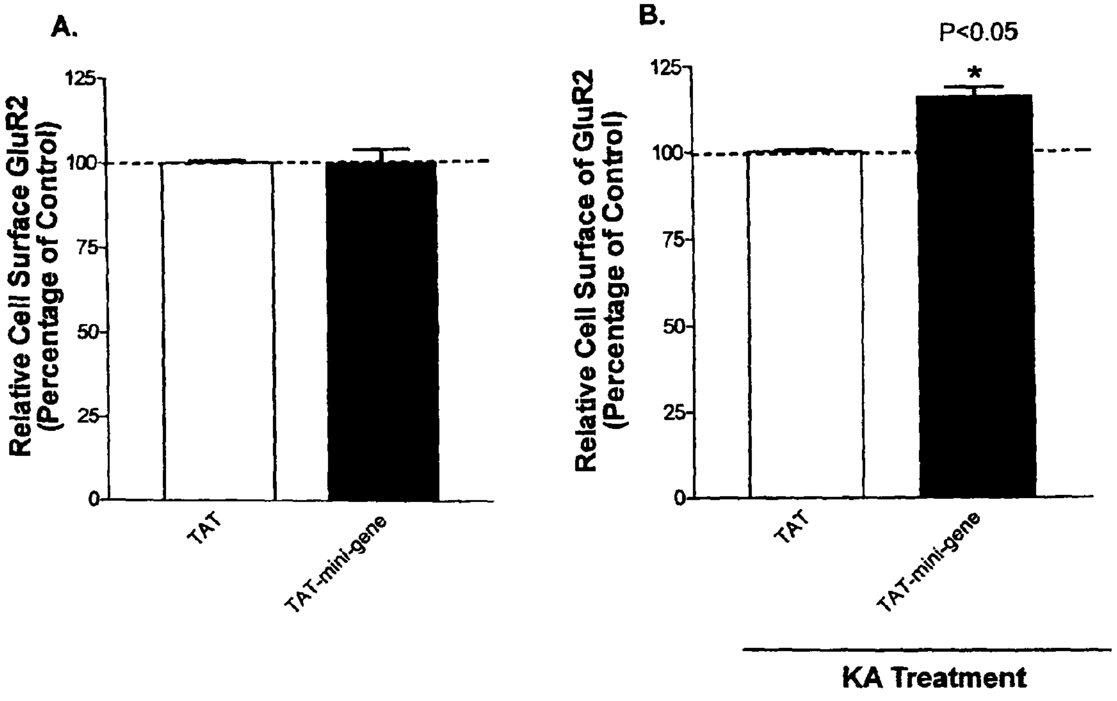
FIG. 14 shows results that suggest interruption of the GAPDH and GluR2 interaction results in an increase in GluR2 subunits localized at the cell surface after KA in hippocampal neurons. (A) Pretreatment with 10 μM TAT-GluR2 NT 1-3-2 peptide to interrupt the GAPDH and GluR2 interaction had no significant effect on the GluR2 expression at the cell surface compared to the group pretreated with 10 μM TAT-only peptide. (B) The interruption of the protein-protein interaction caused by pretreatment of 10 μM TAT-GluR2 NT1-3-2 peptide increased cell surface GluR2 expression after KA treatment, compared to the TAT-only group. Data are analyzed by Student's t test. The asterisk indicates a significant difference from the AMPA+pCDNA3 group ($p<0.05$; $n=9$).

We also examined GluR2 subunit expression at the plasma membrane in hippocampal neuron culture. The TAT-GluR2 NT1-3-2 peptide (10 μM) was applied for 30 minutes before KA treatment. Intracellular application of GluR2 NT1-3-2 peptide significantly increased the cell surface expression of GluR2 subunits after KA treatment (FIG. 14).

Figure 15:
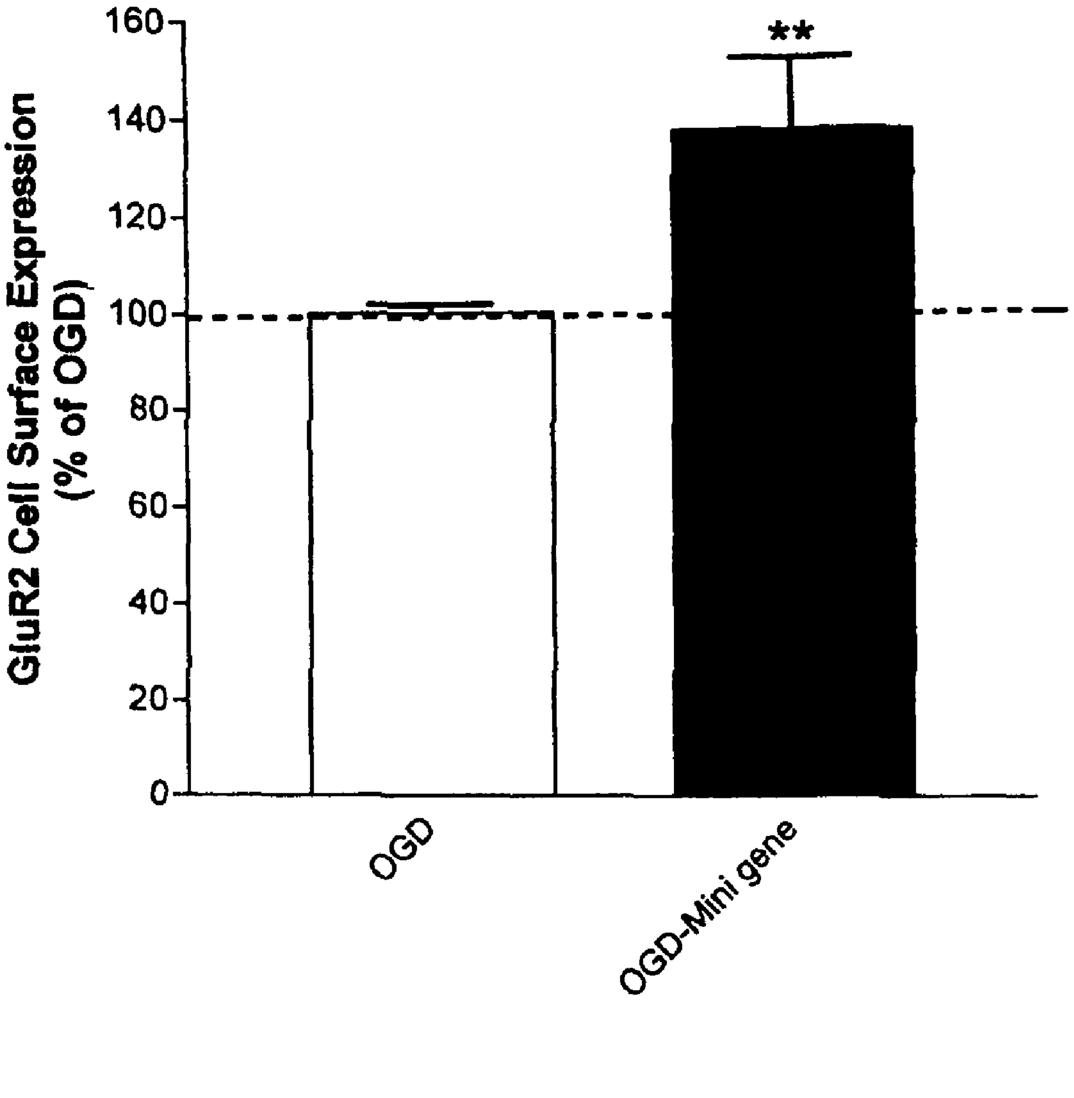
FIG. 15 shows results that suggest that interruption of the GAPDH and GluR2 interaction results in an increase in GluR2 subunits localized at the cell surface in OGD model. The interruption of the protein-protein interaction caused by pretreatment of 10 μM TAT-GluR2 NT1-3-2 peptide increased cell surface GluR2 expression after oxygen-glucose derivation for 2 hours when compared to the TAT-only group. Data are analyzed by Student's t test. The double asterisk indicates a significant difference from the OGD group ($p<0.01$; $n=9$).

We further tested GluR2 subunit expression at the plasma membrane in the OGD model. Hippocampal neurons were deprived of oxygen and glucose for 2 hours and allowed to recover for 24 hours. The TAT-GluR2 NT1-3-2 peptide (10 μM) was applied for 30 minutes OGD treatment. Intracellular application of GluR2 NT1-3-2 peptide also increased the cell surface expression of GluR2 subunits in the OGD model (FIG. 15).

Altogether, these data suggest that the GAPDH and GluR2 association plays an important role in the trafficking of AMPA receptors, which may in turn affect synaptic plasticity.

Example 6

Modulation of the AMPA Receptor-Mediated Excitotoxicity Through the GAPDH and GluR2 Interaction Although the protein-protein interaction between GAPDH and GluR2 NT might play an important role in the trafficking of AMPA receptors, it is still unclear whether the interaction is responsible for the observed AMPA-mediated cell death. To further investigate the functional implication of this biochemical interaction between GAPDH and GluR2 NT, we tested the effects of this interaction on AMPA receptor-mediated excitotoxicity in both transfected HEK293T cells and hippocampal culture neurons. The OGD model was also applied.

Figure 16:
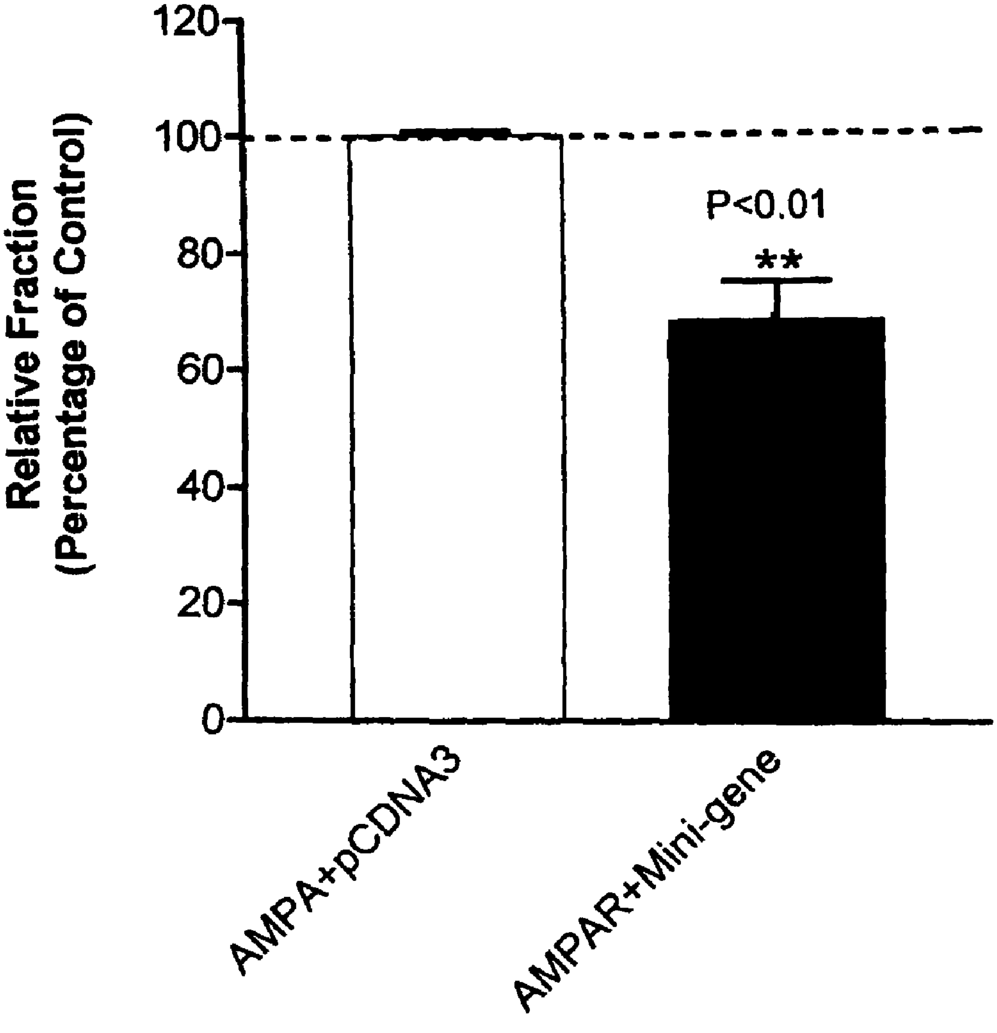
FIG. 16 shows results of regulation of the AMPA receptor-mediated excitotoxicity in HEK293T cells expressing GluR1 and GluR2 subunits by the insertion of GluR2 NT1-3-2 mini-gene. Quantification of AMPA receptor-mediated excitotoxicity through quantitative measurements of PI fluorescence after indicated treatment. After glutamate treatment, the insertion of GluR2 NT1-3-2 mini-gene diminished cell death when compared to the GluR2 NT1-3-2 mini-gene sham-transfected group. Data were analyzed by student's t test. The double asterisks indicate a significant difference from AMPAR+pCDNA group ($p<0.01$; $n=9$)

The AMPA receptor-mediated excitotoxicity was induced by the incubation with 100 mM glutamate. HEK293T cells were transfected with GluR1 and GluR2 subunits alone or in the presence or absence of the GluR2 NT1-3-2 mini-gene. We quantified the AMPA-mediated excitotoxicity by using a PI fluorescence assay. To define the effect of the observed interaction, we examined whether the blockade of the GAPDH and GluR2 NT interaction by using GluR2 NT1-3-2 mini-gene would affect the AMPA-mediated excitotoxicity. With the 100 mM glutamate treatment, the AMPA receptor-mediated cell death was greatly reduced by the overexpression of GluR2 NT1-3-2 mini-gene, compared to mini-gene sham-transfected group (FIG. 16).

Figure 17:
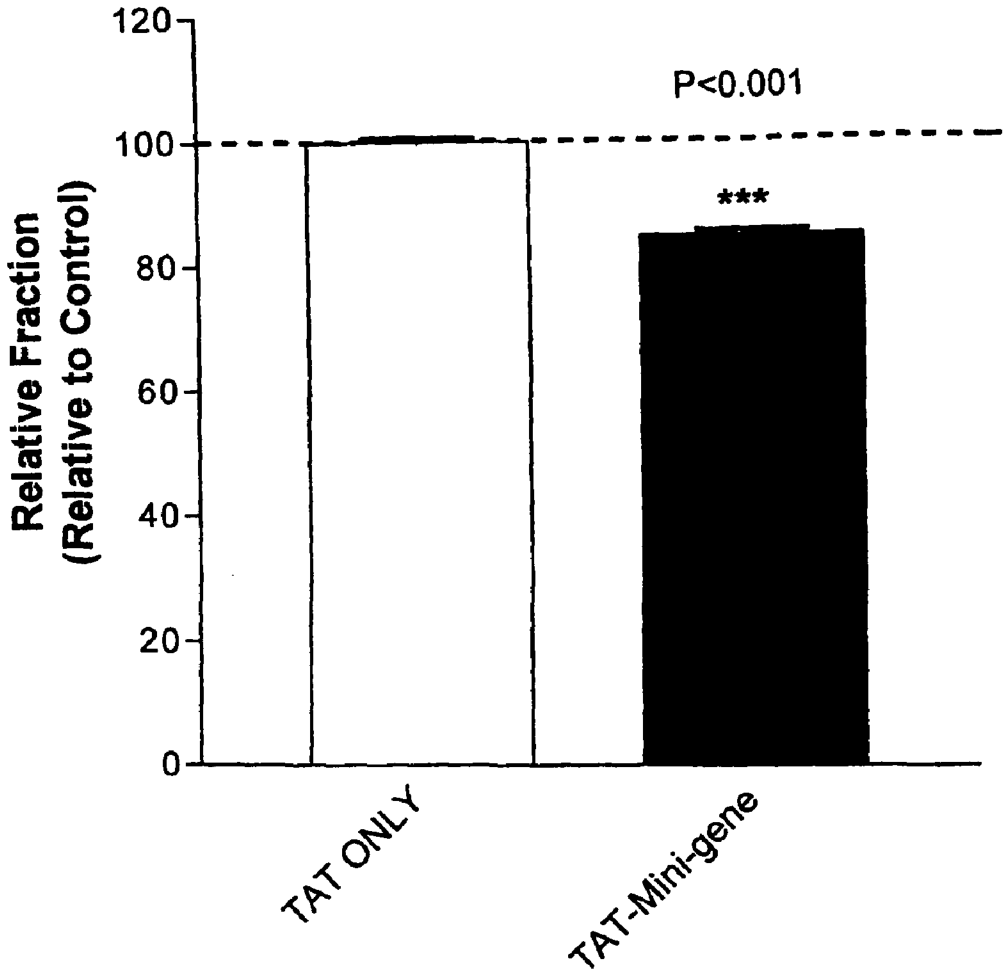
FIG. 17 shows results that regulation of the AMPA receptor-mediated excitotoxicity in rat hippocampal neuron culture. Quantification of the AMPA receptor-mediated excitotoxicity through quantitative measurements of PI fluorescence after indicated treatments is described in the Examples. Pretreatment with 10 μM TAT-GluR2 NT1-3-2 peptide reduced cell death, compared to the group pretreated with 10 μM TAT-only peptide. Data were analyzed by student's t test. The triple asterisks indicate a significant difference from AMPAR+pCDNA3 group ($p<0.001$; $n=9$).

We also examined the AMPA receptor-mediated excitotoxicity in hippocampal culture neurons. Hippocampal neurons were pretreated with either 10 μM TAT only or the TAT-GluR2 NT1-3-2 peptide for 30 minutes. The excitotoxicity was induced by incubation with 100 μM KA and 30 μM cyclothiazide (to prevent AMPA receptor desensitization). The neurons were allowed to recover for 24 hours. In the TAT-GluR2 NT1-3-2 group, AMPA receptor-mediated excitotoxicity was reduced when compared to the TAT only group (FIG. 17).

Figure 18:
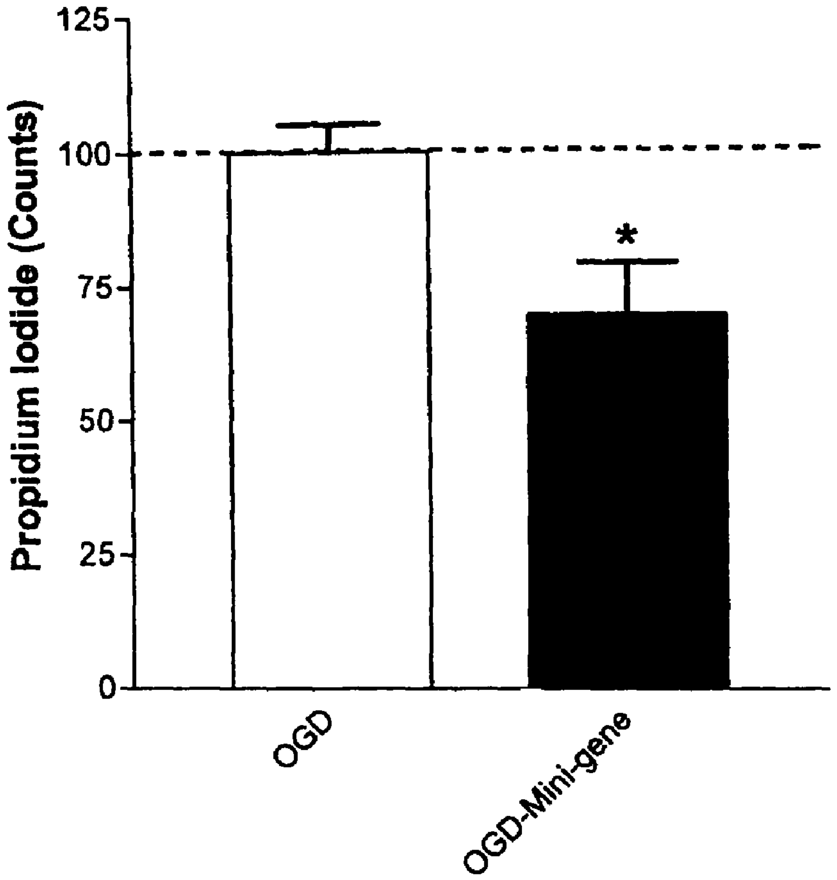
FIG. 18 shows results of regulation of the AMPA receptor-mediated excitotoxicity in the OGD model. The AMPA receptor-mediated excitotoxicity was measured through quantitative measurements of PI fluorescence after indicated treatments. Pretreatment with 10 μM TAT-GluR2 NT1-3-2 peptide reduced cell death when compared to the group pretreated with 10 μM TAT-only peptide. Data were analyzed by student's t test. The asterisk indicates a significant difference from AMPAR+pCDNA3 group ($p<0.001$; $n=9$).

We further tested the AMPA receptor-mediated excitotoxicity in the OGD model. Hippocampal neurons were pretreated with either 10 μM TAT only or the TAT-GluR2 NT1-3-2 peptide for 30 minutes. The excitotoxicity was induced by incubation with the OGD treatment. The neurons were allowed to recover for 24 hours. In the TAT-GluR2 NT1-3-2 group, AMPA receptor-mediated excitotoxicity was reduced when compared to the TAT only group in OGD treatment (FIG. 18). These data from the HEK 293T cells, hippocampal neurons and OGD models strongly suggest that the protein-protein interaction between the GAPDH and GluR2 NT is essential for the AMPA receptor-mediated excitotoxicity.

Example 7

Figure 19:
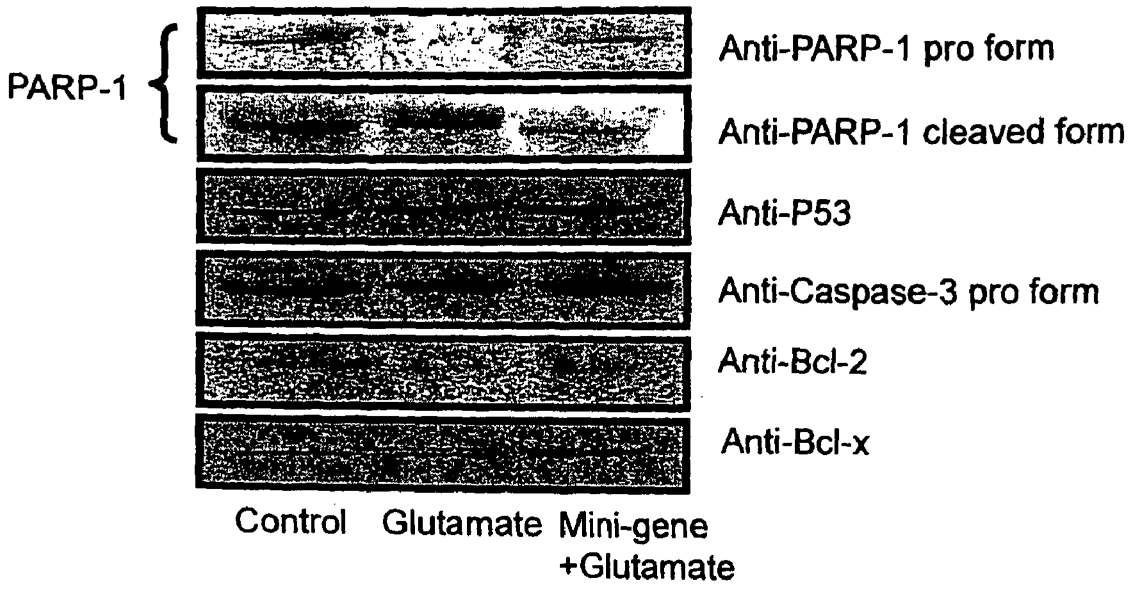
FIG. 19 shows results suggesting molecules involved in the regulation of AMPA-receptor mediated excitotoxicity. The expression levels of PARP, P53, caspase-3, Bcl-2 and Bcl-x were tested by immunoblotting. In transfected HEK 293T cells, glutamate treatment (100 μM) and the insertion of the GluR2 NT1-3-2 mini-gene affected the expression level of PARP, caspase-3, Bcl-2 and Bcl-x.
Figure 20:
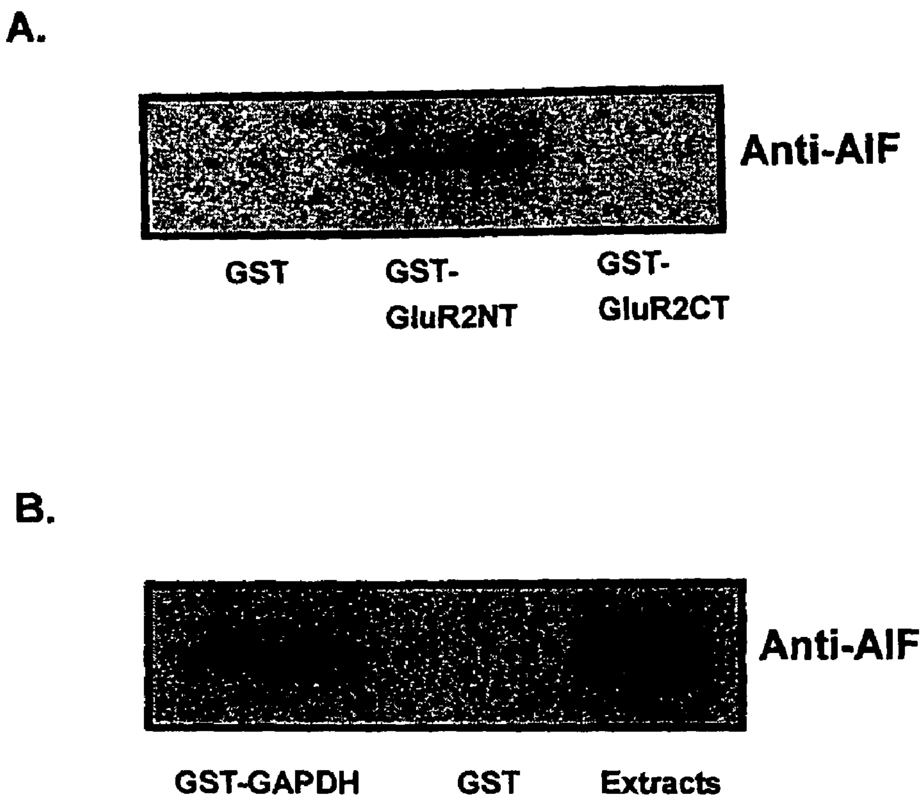
FIG. 20 shows results of biochemical association of AIF with the GluR2 subunit and APDH. Detergent extracts of rat hippocampus were incubated with GST-fusion proteins of GluR2CT or GluR2NT coupled to Glutathione-Sepharose beads for affinity purification. (A) AIF was precipitated by GST-GluR2NT, but not by GST-GluR2CT or GST alone. (B) Western blotting of AIF from solubilized rat hippocampal extracts showed the presence of AIF after affinity precipitation by GST-GAPDH, but not by GST alone.

Potential Molecules Involved in the Regulation of the Function of the GluR2 Subunit and GAPDH Complex and their Translocation In order to determine the potential molecules involved in the regulation of the AMPA receptor-mediated excitotoxicity, we focused on several molecules in the cell death pathway, such as poly ADP-ribose polymerase (PARP), P53, caspase-3, Bcl-2 and Bcl-x. In transfected HEK 293T cells, glutamate treatment (100 μM) and the insertion of the GluR2 NT1-3-2 mini-gene affected the expression level of PARP, caspase-3, Bcl-2 and Bcl-x (FIG. 19).

There is no nuclear localization signal on GAPDH, while there are some potential nuclear localization signals in the amino terminus of the GluR2 subunit. We also tested the potential protein which might lead GAPDH translocation from other cell compartments to the nucleus. Apoptosis inducing factor (AIF) possesses both mitochondria and nuclear localization signals. In the affinity purification assay, GST-fusion protein GST-GluR2NT and GST-GAPDH, but not GST-GluR2CT or GST alone, precipitated AIF in rat hippocampal extracts. Altogether, these data suggest that several molecules are involved in the regulation of the trafficking of AMPA receptors and GAPDH, as well as AMPA-receptor mediated excitotoxicity.

Example 8

Agonist Regulation of Extracellular GAPDH: AMPAR Complex Formation

Figure 21:
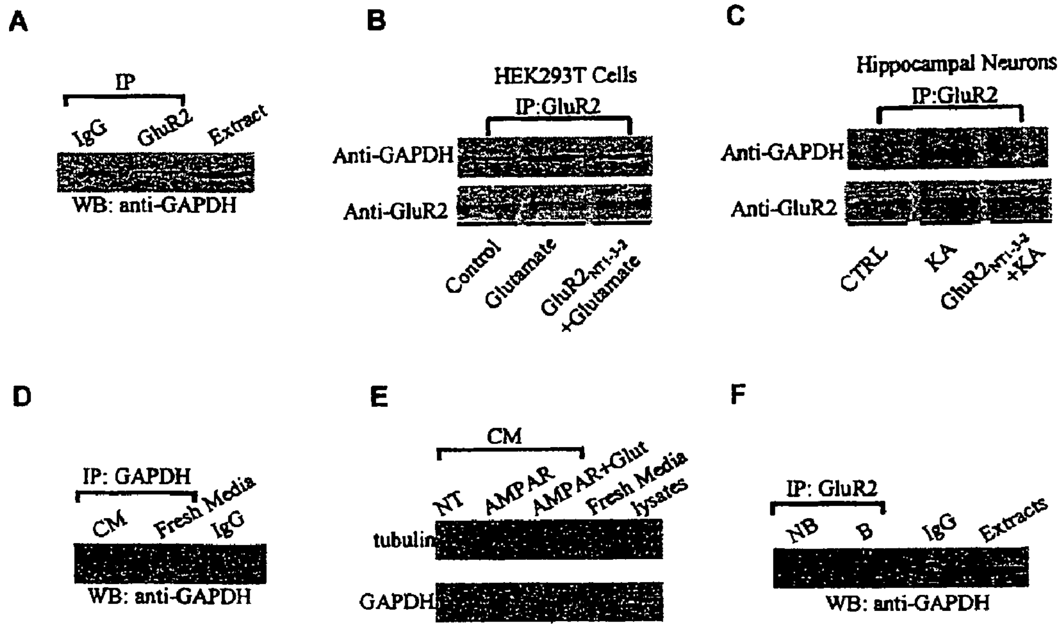
FIG. 21 shows results validating agonist regulation of the extracellular GAPDH: AMPAR complex formation. (A) Co-immunoprecipitation of GAPDH with the GluR2 subunit from solubilized rat hippocampus. (B-C) Activation of AMPAR (HEK-293T: 100 μM glutamate, 30 min; neurons: 100 μM kainic acid [KA], 30 min), enhanced the association of GAPDH and GluR2 subunit, which was blocked by preincubation with the GluR2 NT1-3-2 peptide in both HEK-293T cells expressing GluR1/2 subunits (B) and primary cultures of rat hippocampal neurons (C) but did not affect directly immunoprecipitated GluR2 levels (B, C, bottom panels). (D) Using a rabbit anti-GAPDH antibody, GAPDH immunoprecipitated from the conditioned medium (CM) of primary cultures of rat hippocampal neurons but not from fresh control medium. Rabbit IgG was used as negative control. (E) Conditioned media of nontransfected HEK-293T cells and HEK-293T cells transfected with GluR1/2 subunits, in the presence or absence of glutamate (Glut), was concentrated to examine the expression of GAPDH and α-tubulin. GAPDH was present in conditioned media and cell lysates, while α-tubulin was only present in cell lysates. (F) Rat hippocampal neurons were incubated with sulfo-NHS-LC biotin to label cell surface proteins. The amount of GAPDH that co-immunoprecipitated with GluR2 subunit was examined in both non-biotinylated (NB) and biotinylated (B) proteins.

To investigate whether GAPDH forms a complex with AMPAR in vivo, we performed co-immunoprecipitation experiments with proteins extracted from the rat hippocampus. As shown in FIG. 21A, immunoprecipitation of GluR2 was able to co-precipitate GAPDH from solubilized proteins extracted from rat hippocampus, indicating a physical interaction between GluR2 and GAPDH may occur in vivo. We then tested if AMPAR activation affected the observed GAPDH-GluR2 interaction. Although GAPDH and AMPAR could associate with each other without exogenous stimulation in HEK-293T cells expressing GluR1/GluR2 subunits (FIG. 21B, top panel) and in primary cultures of rat hippocampal neurons (FIG. 21C, top panel), activation of AMPAR resulted in a 75±18% (mean±SE, n=3) and 58±11% (mean±SE, n=3) increase in the co-immunoprecipitation of GAPDH with GluR2, respectively. Agonist stimulation did not significantly alter the levels of directly immunoprecipitated GluR2 subunit (FIG. 21B, C, bottom panels). Interestingly, preincubation of the GluR2 NT1-3-2 peptide (10 μM, 1 hour) significantly inhibited the agonist-induced increase in the GAPDH: AMPAR complex formation in HEK-293T cells expressing GluR1/GluR2 (FIG. 21B) and in hippocampal neurons (FIG. 21C). The disruption of the GAPDH-GluR2 interaction by the extracellular application of the interfering GluR2 NT1-3-2 peptide suggested that the GAPDH and GluR2 complex formation may occur extracellularly. Indeed, a recent study demonstrated that in several mammalian cell lines, including HEK-293 cells and neuro-2a cells, GAPDH was constitutively secreted into the extracellular space (101). Furthermore, the $GluR2_{NT}$ interacting proteins Narp and N-cadherins are also extracellular proteins (24, 90). Thus, without wishing to be bound by theory, it is possible that secreted GAPDH may form a protein complex with $GluR2_{NT}$. We first confirmed GAPDH secretion in our cell lines by immunoprecipiting GAPDH from the conditioned medium of hippocampal primary cultures with a primary antibody against GAPDH (rabbit polyclonal). As shown in FIG. 21D, GAPDH was immunoprecipitated from serum-free conditioned medium, but not from fresh serum-free medium. To further clarify that the GAPDH from conditioned medium was secreted from cells and not a result from cell lysis, serum-free conditioned medium of nontransfected HEK-293 cells and cells co-expressing GluR1/GluR2 was collected, concentrated and examined by Western blot analyses using anti-GAPDH and anti-α-tubulin antibodies. As shown in FIG. 21E, regardless of GluR1/GluR2 coexpression, GAPDH was detected from both conditioned media and cell lysates while α-tubulin (an intracellular protein marker) was only detected from the cell lysates, indicating that GAPDH observed in the conditioned medium was secreted from cells and not a contaminant from cell lysis. Furthermore, to test whether GAPDH and GluR2 interaction occurred extracellularly, we performed cell surface biotinylation experiments in hippocampal neurons. As shown in FIG. 21F, GluR2 antibody co-immunoprecipitated GAPDH from the biotinylated (cell surface) fraction, but failed to co-immunoprecipitate GAPDH from the non-biotinylated (intracellular) fraction. These data together strongly suggested that GAPDH is secreted to extracellular space where it is accessible for interaction with the N-terminus of the GluR2 subunit.

Example 9

Figure 22:
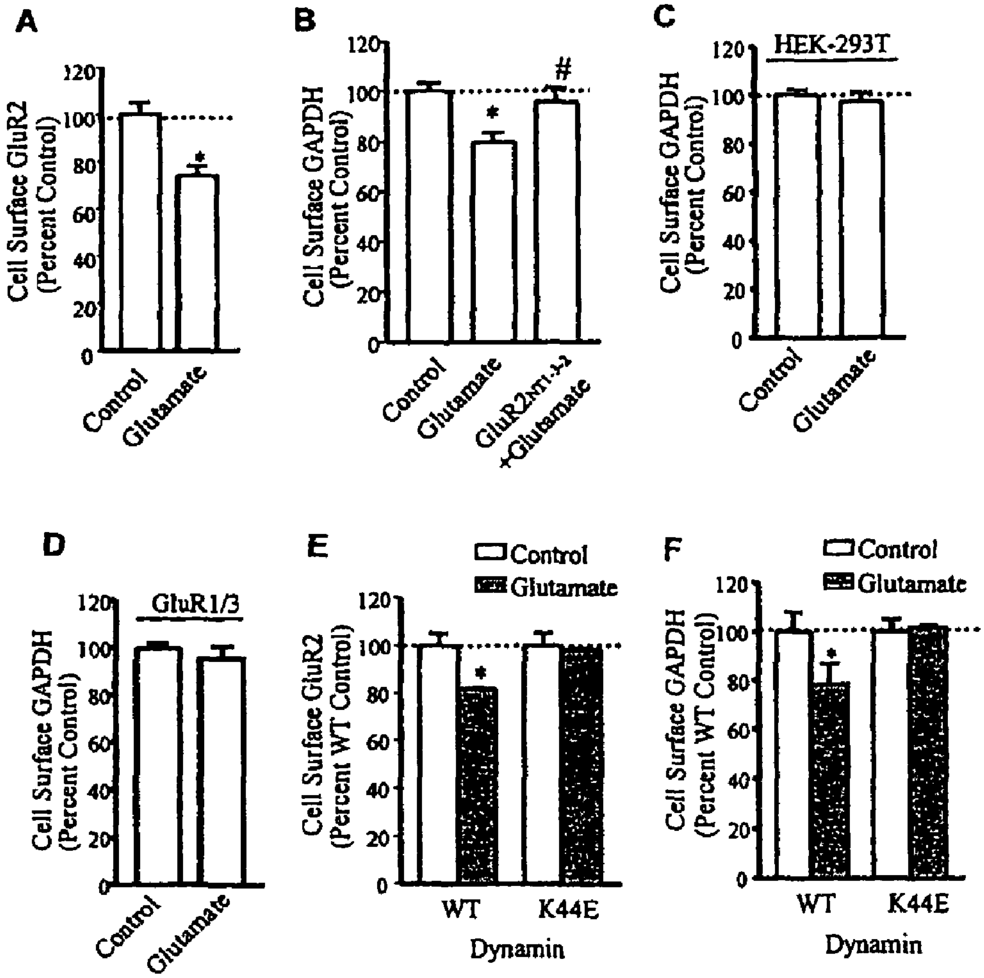
FIG. 22 shows results suggesting activation of AMPAR induces GAPDH internalization in HEK-293T cells co-expressing GluR1/GluR2 subunits. (A) Glutamate (100 μM, 30 min) induced cell surface GluR2 internalization by 26.3±4.1%. t-test * Significantly different from control group (n=9, P<0.05). (B) Agonist stimulation induced cell surface GAPDH internalization by 20.6±3.9%, while preincubation of the GluR2 NT1-3-2 peptide abolished the agonist-induced GAPDH internalization. ANOVA, followed by post-hoc Student-Newman-Keels test * Significantly different from control group; # significantly different from glutamate group (n=9, P<0.05). (C) Glutamate failed to internalize GAPDH in HEK-293T cells in the absence of GluR1/GluR2 subunits. (D) Glutamate failed to internalize GAPDH in HEK-293T cells transfected with GluR1/GluR3 subunits. (E) Glutamate induced GluR2 internalization by 18.1±0.6% in HEK-293T cells transfected with wild type dynamin, which was blocked by the co-expression of mutant K44E dynamin. ANOVA, followed by post-hoc Student-Newman-Keuls test * Significantly different from control group (n=9, P<0.05). (F) The glutamate induced GAPDH internalization by 21.4±8.3% in HEK-293T cells transfected with wild type dynamin, which was blocked by the co-expression of mutant K44E dynamin. ANOVA, followed by post-hoc Student-Newman-Keuls test *Significantly different from control group (n=9, P<0.05).

Activation of AMPAR Induces GAPDH Internalization Through GAPDH-GluR2 Interaction Previous studies have demonstrated agonist induced AMPAR endocytosis (53. Carroll et al., 1999; 76. Lin et al., 2000; 82. Man et al., 2000). Thus, we examined whether extracellular GAPDH would internalize along with AMPARs through the GAPDH-GluR2 interaction upon agonist stimulation of AMPAR. Consistent with our hypothesis, glutamate stimulation (100 μM, 30 min) induced a significant decrease in not only GluR2 plasma membrane localization (FIG. 22A) but also in cell surface-associated GAPDH (FIG. 22B) in cells co-expressing GluR1/GluR2 as indexed by cell based ELISA assay. The ability of the GluR2 NT1-3-2 peptide to abolish the glutamate induced decrease in GAPDH plasma membrane expression (FIG. 3B), together with the inability of glutamate stimulation to internalize GAPDH in the absence of GluR1/GluR2 subunits in HEK-293T cells (FIG. 22C), suggested that the observed GAPDH internalization maybe a passive process enabled by the GAPDH-GluR2 interaction and dependent on GluR2 internalization. The essential role of GluR2 subunit in the GAPDH internalization was also confirmed in GluR1/GluR3 co-expressing cells, in which glutamate stimulation failed to induce GAPDH internalization (FIG. 22D). Previous studies showed that GluR2 endocytosis was dynamin-dependent and that expression of the dominant-negative dynamin mutant (K44E) is able to block GluR2 internalization (53, 82). Thus, after confirming the ability of the K44E dynamin mutant to block GluR2 internalization (FIG. 22E), we examined whether the dynamin mutant could also affect GAPDH internalization in cells co-expressing GluR1/GluR2 in HEK-293T cells. As shown in FIG. 22F, the K44E dynamin mutant significantly inhibited glutamate induced GAPDH internalization, indicating that GAPDH internalizes through a dynamin dependent pathway.

Example 10

GAPDH and GluR2 Translocate to the Nucleus Through the GAPDH-GluR2 Interaction

Figure 23:
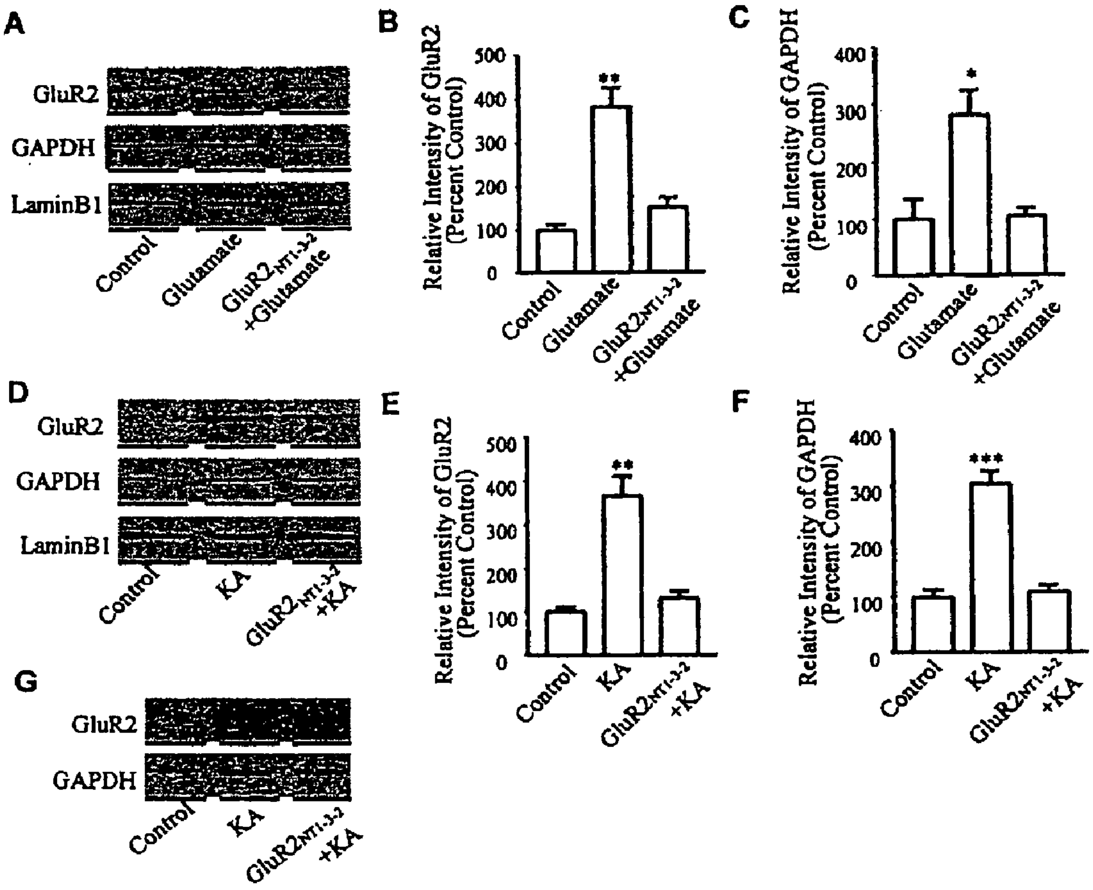
FIG. 23 shows results suggesting that translocation of cell surface GAPDH and GluR2 into nucleus is dependent on the GAPDH-GluR2 interaction. (A-C) Nuclei from HEK-293T cells cotransfected with GluR1/GluR2 were purified, solubilized and run on SDS-PAGE with subsequent Western blot analysis. Both GAPDH and GluR2 nuclear expression was significantly increased upon glutamate treatment (100 μM, 30 min) and the nuclear translocation could be blocked by pre-treatment with the GluR2 NT1-3-2 peptide (10 μM, 1 hr). The intensity of protein bands were measured by Image J software and normalized to the corresponding control samples. (D-F) In hippocampal neurons, both GAPDH and GluR2 nuclear expression was significantly increased upon KA treatment (100 μM KA, 10 μM MK-801, 2 μM nimodipine, 30 min) and the nuclear translocation could be blocked by GluR2 NT1-3-2 peptide (10 μM, 1 hr). The intensity of protein bands were measured by Image J software and normalized to the corresponding control samples. (G) Biotinylated cell surface GAPDH and GluR2 translocates to the nucleus. Primary cultures of rat hippocampal neurons were labeled with biotin and then treated with GluR2 NT1-3-2 peptides before agonist stimulation. Nuclei were isolated and nuclear biotinylated proteins were separated from non-biotinylated proteins. Nuclear biotinylated proteins were then run on SDS-PAGE gels and analyzed under subsequent Western blot analysis to examine the nuclear localization of cell surface GAPDH and GluR2.

Previous studies demonstrated that GAPDH initiates apoptotic cell death by nuclear translocation following Siah1 binding (63, 64). Therefore, we next examined if the internalized GAPDH could be translocated to the nucleus upon agonist stimulation of AMPAR. Surprisingly, not only GAPDH but GluR2 also exhibited a significant increase in nuclear localization upon agonist stimulation (FIG. 23A-C). Furthermore, the nuclear translocation of GAPDH and GluR2 could be blocked by the pre-incubation of GluR2 NT1-3-2 peptide in HEK-293T cells expressing GluR1/GluR2 (FIG. 23A-C) or in hippocampal neurons (FIG. 23D-F). To confirm whether the observed nuclear GAPDH and GluR2 originated from the cell surface, hippocampal neurons were first labeled with sulfo-NHS—SS-Biotin and then treated with GluR2 NT1-3-2 peptides before agonist stimulation. Subsequently, all cell surface biotin was cleaved leaving only the endocytosed proteins labeled with biotin. As shown in FIG. 23G, Western blots from SDS-PAGE of nuclear extracts that were streptavidin purified revealed that the levels of biotinylated GAPDH and GluR2 were significantly increased in the nuclear extract of hippocampal neurons upon agonist stimulation, a phenomenon that could be blocked by pre-incubation with the GluR2 NT1-3-2 peptide. Thus, AMPAR activation could lead to the co-internalization of GAPDH and GluR2 mediated by the GAPDH-GluR2 coupling and resulted in the translocation of GluR2 and GAPDH to the nucleus.

Example 11

Activation of AMPAR Facilitates Nuclear GAPDH-p53 Coupling

Figure 24:
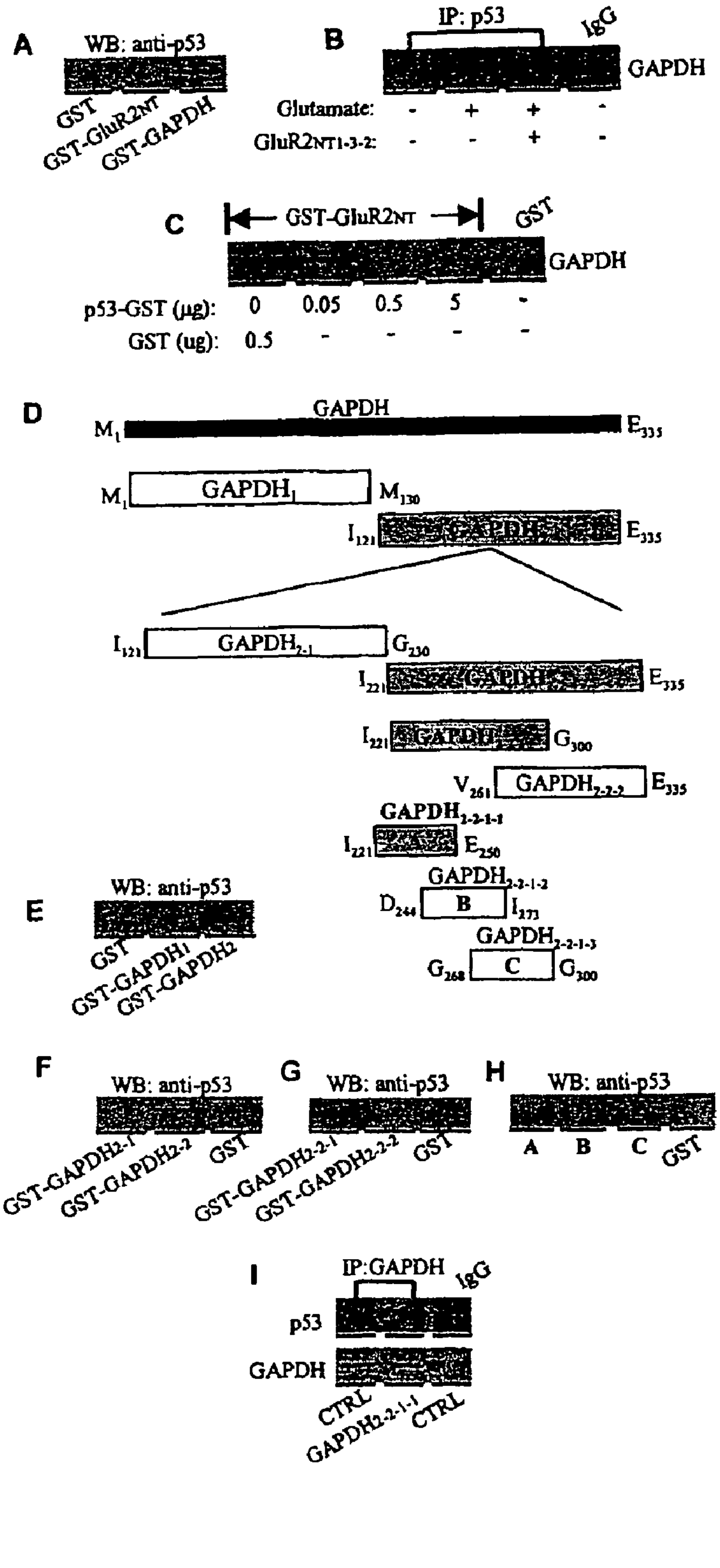
FIG. 24 shows results suggesting biochemical association of nuclear GAPDH and p53. (A) p53 was specifically pulled down by GST-GAPDH from rat hippocampal extracts, but not by GST-GluR2$_{NT}$ or GST alone. (B) Co-immunoprecipitation of GAPDH with p53 from extracted nuclear proteins of HEK-293T cells expressing AMPAR, treated with 100 μM glutamate and inhibited by GluR2 NT1-3-2 peptide pretreatment. (C) The interaction between GAPDH-GluR2 is inhibited by the presence of recombinant p53. The ability of GST-GluR2$_{NT}$ (20 μg) to pull down GAPDH from nuclear extracts of HEK-293T cells co-expressing GluR1/GluR2 subunits treated with glutamate was examined in the presence of increasing concentration of recombinant p53 (GST tagged). Addition of 0.5 μg of GST peptide did not affect the ability of GST-GluR2$_{NT}$ to pull down GAPDH. (D) Schematic representation of GST-fusion proteins encoding truncated GAPDH segments. (E) p53 was specifically pulled down by GST-GAPDH$_2$ from rat hippocampal extracts, but not by GST-GAPDH$_1$ or GST alone. (F) p53 was specifically pulled down by GST-GAPDH$_{-2-2}$ from rat hippocampal extracts, but not by GST-GAPDH$_{-2-1}$ or GST alone. (G) p53 was specifically pulled down by GST-GAPDH$_{2-2-1}$ from rat hippocampal extracts, but not by GST-GAPDH$_{2-2-2}$ or GST alone. (H), p53 was specifically pulled down by GST-GAPDH(2-2-1-1) from rat hippocampal extracts, but not by other GST fusion proteins or GST alone. (I) The expression of GAPDH(2-2-1-1) mini-gene disrupted the co-immunoprecipitation of p53 with GAPDH in transfected HEK-293T cells.

GAPDH nuclear localization was previously implicated in apoptosis (25. Chuang et al., 2005) and p53, a tumor suppressor and transcription factor, which can also initiate apoptosis, has been implicated in glutamate-mediated excitotoxicity (72, 91, 95). More interestingly, a previous study showed an interaction between GAPDH and p53 (45). Thus, we tested whether $GluR2_{NT}$ and GAPDH can interact with p53 using affinity "pull down" purification experiments. Interestingly, only GST-GAPDH, but not GST-$GluR2_{NT}$ or GST alone, affinity precipitated p53 from nuclear extracts of rat hippocampal neurons (FIG. 24A). In addition, as shown in FIG. 24B, GAPDH co-immunoprecipitated with p53 taken from isolated nuclei of primary cultures of hippocampal neurons, indicating a physical interaction exists between GAPDH and p53, an interaction that appears to be facilitated by AMPAR activation. Furthermore, we found that p53 acted as a competitive inhibitor to GAPDH-GluR2 coupling since pretreatment with the interfering GluR2 NT1-3-2 peptide, which we have shown to disrupt the GAPDH-GluR2 interaction, also inhibited the GAPDH-p53 interaction (FIG. 24B), and pre-incubation with purified p53-GST, but not GST alone, inhibited GluR2-GAPDH coupling in a concentration dependent manner, as indexed by affinity "pull down" experiments (FIG. 24C). To identify the p53 interacting domain on GAPDH, GST-fusion proteins encoding truncated fragments of GAPDH were constructed and used in affinity purification assays (FIG. 24D). These results revealed that the sequence encoded by the GAPDH: $I_{221}$-$E_{250}$ facilitates the interaction with p53 since only the GST-GAPDH(2-2-1-1) was able to pull-down p53 from solubilized nuclear proteins extracted from rat hippocampus (FIG. 24E-H). Furthermore, we confirmed the essential role of I221-E250 in maintaining GAPDH-p53 coupling. As shown in FIG. 24I, co-expression of the GAPDH(2-2-1-1) mini-gene was able to block co-immunoprecipitation of p53 with GAPDH.

Example 12

Figure 25:
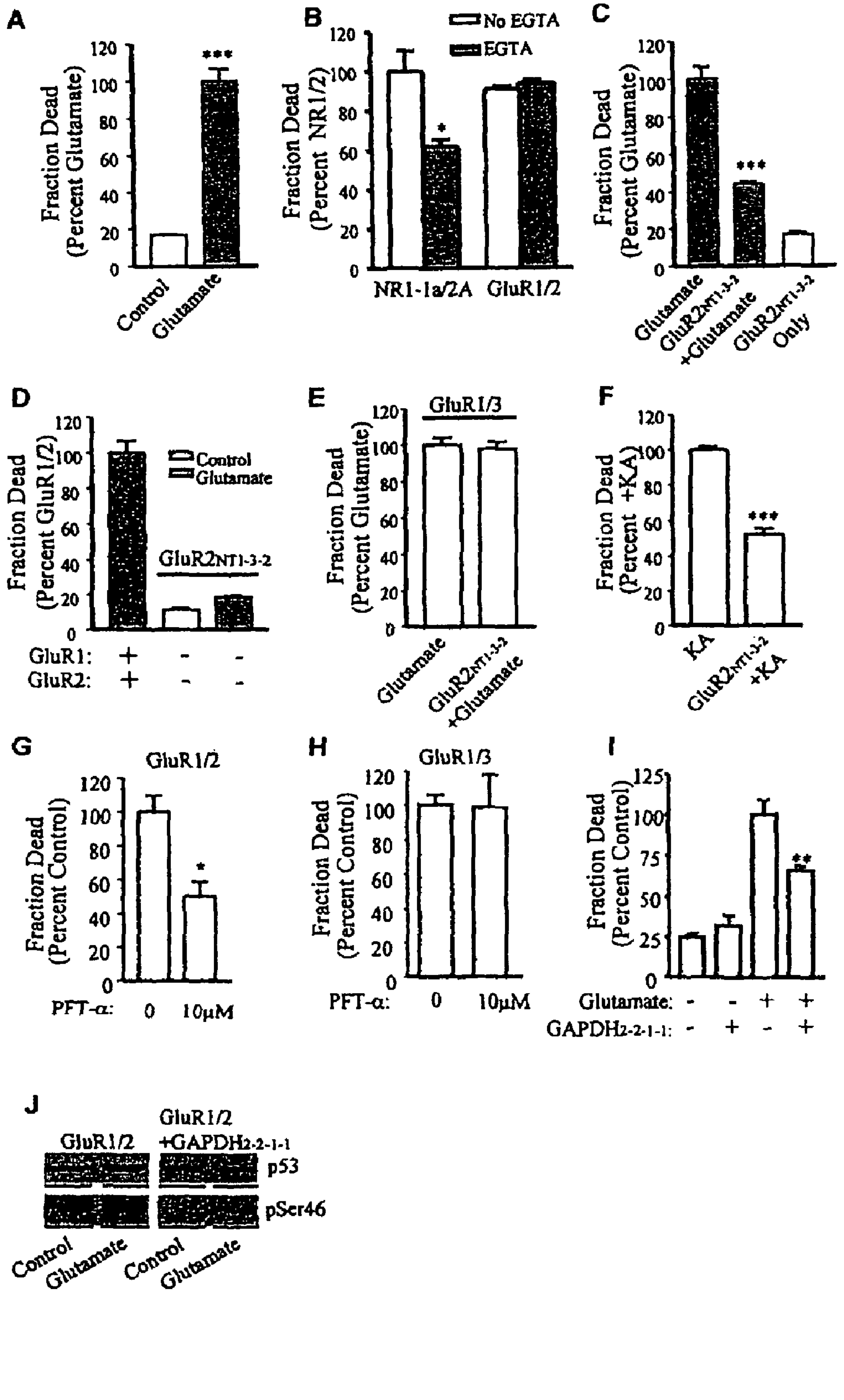
FIG. 25 shows results suggesting regulation of the AMPAR-mediated cell death in HEK-293T cells. (A) Activation of AMPAR (300 μM glutamate, 25 μM CTZ, 24 hr) induced significant cell death in HEK-293T cells expressing GluR1/2. Toxicity was indexed by measuring propidium iodide (50 μg/mL) incorporation. ***Significantly different from control group (n=9, P<0.001), t-test. (B) Depletion of calcium with 5 mM EGTA inhibited the NR1-1a/2A NMDA receptor-mediated cell death by 38±3.6%, while the GluR1/GluR2 AMPAR-mediated cell death remained intact. *Significantly different from NR1-1a/2A without EGTA group (n=9, P<0.05), ANOVA, followed by post-hoc Student-Newman-Keuls test. (C) Pretreatment with GluR2 NT1-3-2 peptide (10 μM, 1 hr) in HEK-293T cells significantly attenuated AMPAR-mediated cell death by 56±1.6%. The GluR2 NT 1-3-2 peptide itself showed no effect on HEK-293T cells in the absence of glutamate treatment. *Significantly different from glutamate group (n=9, P<0.001), ANOVA, followed by post-hoc Student-Newman-Keuls test. (D) The GluR2 NT1-3-2 peptide itself showed no effect on HEK-293T cells in the absence of GluR1/GluR2 co-expression. (E) The GluR2 NT1-3-2 peptide failed to inhibit GluR1/3 AMPAR-mediated cell death. (F) The GluR2 NT1-3-2 peptide significantly inhibited AMPAR-mediated cell death (100 μM KA, 10 μM MK-801, 2 μM nimodipine, 1 hr) by 47.6±3.3% in cultured rat hippocampal neurons. *Significantly different from KA group (n=9, P<0.001), t-test. (G) Glutamate-induced cell death was significantly inhibited by 49.8±18.3% by pre-treatment of p53 antagonist cyclic (10 μM, 1 hr) PFT-α in HEK-293T cells expressing GluR1/2. *Significantly different from 0 μM group (n=9, P<0.05), t-test. (H) Cyclic PFT-α failed to inhibit glutamate-induced cell death in HEK-293T cells expressing GluR1/3. (I) Glutamate-induced cell death was significantly inhibited in cells co-expressing GluR1/2 with GAPDH(2-2-1-1) compared to cells expressing GluR1/2.** (J) Both the expression of p53 and the phosphorylation of p53 at serine 46 were enhanced upon agonist stimulation in HEK-293T cells expressing GluR1/2, but not in cells co-expression GluR1/2 with GAPDH(2-2-1-1) mini-gene.

Both GluR2-GAPDH and GAPDH-p53 Play Roles in GluR2-Containing AMPAR-Mediated Cell Death AMPAR endocytosis was recently shown to be required for excitotoxic neuronal injury (Wang et al, 2004). Moreover, both GAPDH and p53 have been independently shown to be involved in cell toxicity (4, 25, 3). Therefore, we suspected that the sequential internalization and protein-protein interactions among GluR2, GAPDH and p53 may play an essential role in mediating AMPAR-induced excitotoxicity. Consistent with previously studies (52, 67), treatment of HEK-293T cells expressing GluR1/2 with glutamate (300 μM, 24 hour; plus 25 μM cyclothiazide to prevent AMPAR desensitization) produced significant cell death (FIG. 25A). Given that excessive influx of $Ca^{2+}$ through glutamate receptor channels is thought to be responsible for glutamate induced cell death, we then examined the role of extracellular $Ca^{2+}$ in the observed GluR2-containing AMPAR-mediated cell death. HEK-293T cells expressing either GluR1/GluR2 or NR1/2A were exposed to glutamate in the presence or absence of EGTA (5 mM). As shown in FIG. 25B, in the presence of EGTA, NMDA receptor-mediated cell death was significantly reduced, while the GluR1/GluR2 AMPAR-mediated cell death remains intact, indicating that cell death induced by GluR2-containing AMPAR may not be dependent on extracellular $Ca^{2+}$ influx via the ionotropic receptor. To investigate the involvement of GluR2-GAPDH interaction in AMPAR-mediated cell death, we pre-treated with the GluR2 NT1-3-2 peptide (10 μM, 1 hour) in HEK-293T cells expressing GluR1/GluR2. As shown in FIG. 25C, pre-incubation with the GluR2 NT1-3-2 peptide attenuated AMPAR-mediated cell death by 56±1.6%, suggesting that disruption of GAPDH-GluR2 coupling may indeed rescue cells from AMPAR mediated cell death. The GluR2 NT1-3-2 peptide itself showed no effect on either GluR1/2 transfected cells without glutamate treatment or in nontransfected cells regardless of glutamate treatment (FIGS. 25C and 25D). The specificity of the GluR2 NT1-3-2 peptide was also confirmed in cells co-expressing GluR1/3 subunits, where pre-incubation with the GluR2 NT1-3-2 peptide failed to inhibit GluR1/3 AMPAR-mediated cell death (FIG. 25E). These data suggested that the GAPDH-GluR2 interaction may play a role in GluR2-containing AMPAR-mediated cell death.

To examine the GAPDH: AMPAR interactions in a relevant cellular milieu, primary cultures of rat hippocampal neurons were utilized in parallel experiments. We have previously shown in FIG. 21C that pre-incubating hippocampal neurons with the GluR2 NT1-3-2 peptide could disrupt the GAPDH-GluR2 interaction that was promoted by AMPAR activation. We subsequently examined if disruption of this interaction in hippocampal neurons could rescue cells from AMPAR-mediated cell death. AMPAR-mediated cell death was induced by pretreating neurons with kainic acid (KA; 100 μM, 1 hour) in the presence of NMDA receptor and $Ca^{2+}$ channel antagonists (10 μM MK-801 and 2 μM nimodipine, respectively). As shown in FIG. 25F, pretreatment with the GluR2 NT1-3-2 peptide significantly inhibited AMPAR-mediated cell death. These results suggested that the AMPAR could functionally interact with GAPDH and that disruption of this interaction leads to a significant decrease in AMPA-mediated cell death in neurons.

We then investigated the role of GAPDH-p53 coupling in GluR2-containing AMPAR-mediated neurotoxicity. As shown in FIG. 25G, pre-treating HEK-293T cells expressing GluR1/GluR2 with the p53 antagonist PFTα (10 μM, 1 hour) significantly inhibited glutamate-induced cell death, while PFTα failed to inhibit glutamate-induced cell death in cells expressing GluR1/3 (FIG. 25H), suggesting that GluR2-containing AMPAR induces cell death through a p53-dependent pathway. To examine whether GAPDH-p53 coupling plays a functional role in GluR2-containing AMPAR induced cell death we co-transfected a mini-gene encoding the GAPDH (2-2-1-1) in HEK-293T cells co-expressing GluR1/GluR2, which results in the disruption of the GAPDH-p53 interaction as previously shown in co-immunoprecipitation experiments (FIG. 24I). As shown in FIG. 25I, agonist induced GluR2-containing AMPAR-mediated cell death was significantly inhibited in cells co-expressing the GAPDH(2-2-1-1) mini-gene, indicating the critical role of GAPDH-p53 coupling in GluR2-containing AMPAR-mediated cell death. Previous studies demonstrated a strong correlation between p53 expression and excitotoxic neuronal death (72, 91, 95), while other studies reported phosphorylation can regulate p53 activity (51). Thus, we tested whether enhancing the GAPDH-p53 coupling by AMPAR activation affects p53 expression and phosphorylation. As shown in FIG. 25J, both the expression of p53 and the phosphorylation of p53 were enhanced upon agonist stimulation in cells expressing GluR1/GluR2, but not in cells co-expressing GluR1/GluR2 and the GAPDH(2-2-1-1) mini-gene. Together, these data suggested that GluR2-mediated GAPDH nuclear translocation is responsible for GluR2-containing AMPAR-mediated cell death, which facilitates the interaction between GAPDH and p53 and activates p53-dependent apoptosis pathway.

Example 13

Testing of GluR2 NT Mutants

Figure 26:
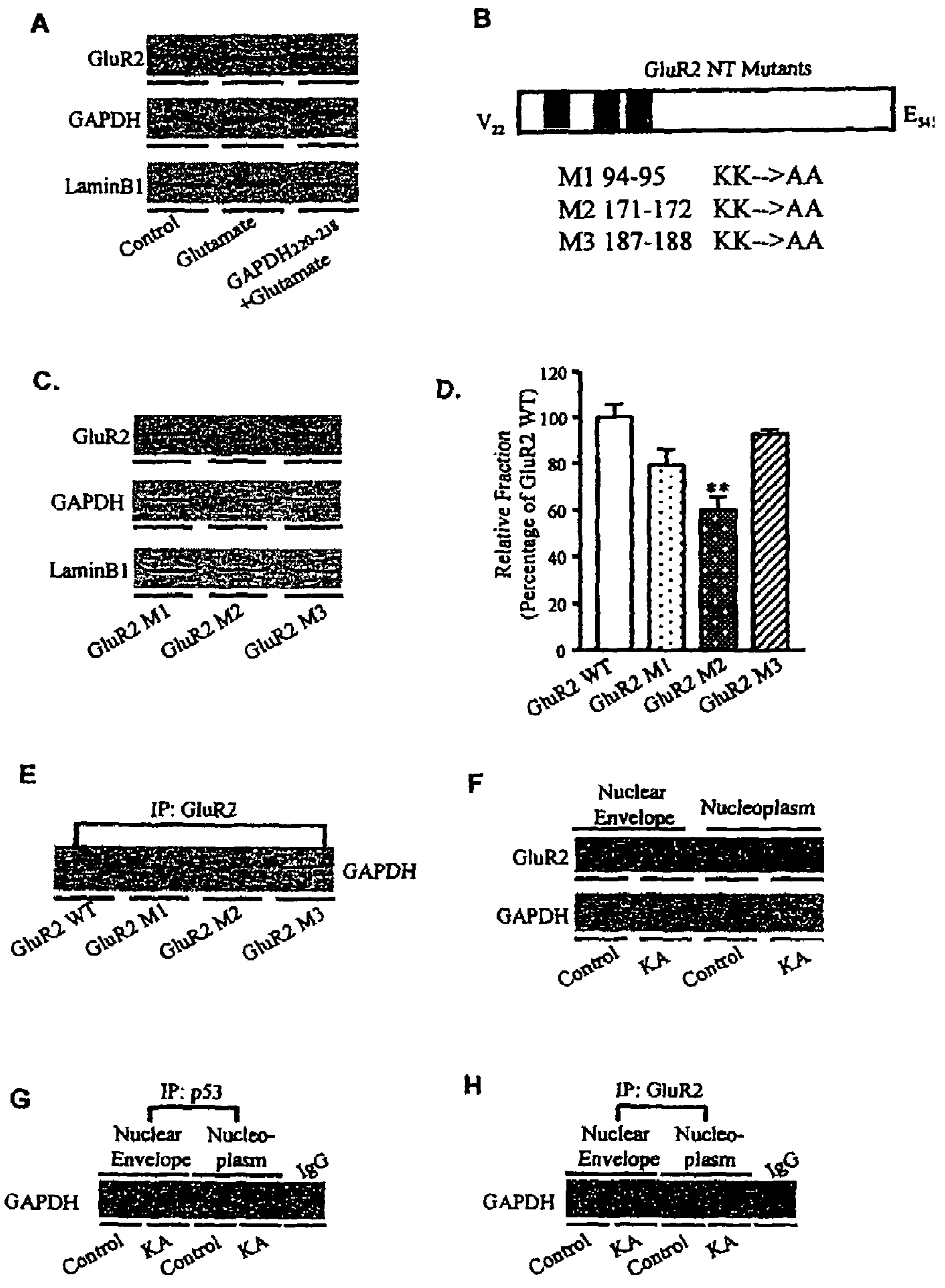
FIG. 26 shows results of experiments performed using mutants of sequences as defined herein. (A) Nuclei from HEK-293T cells cotransfected with GluR1/GluR2 were purified, solubilized and run on SDS-PAGE with subsequent Western blot analysis. Both GAPDH and GluR2 nuclear expression was significantly increased upon glutamate treatment (100 μM, 30 min) and the nuclear translocation could NOT be blocked by co-transfection of the GluR2$_{220-238}$ mini-gene. GluR2$_{220-238}$ is the binding site of GluR2 and Siah1.

Experiments were performed using mutants of sequences as shown in FIG. 26. Nuclei from HEK-293T cells cotransfected with GluR1/GluR2 were purified, solubilized and run on SDS-PAGE with subsequent Western blot analysis. Both GAPDH and GluR2 nuclear expression was significantly increased upon glutamate treatment (100 μM, 30 min) and the nuclear translocation could not be blocked by co-transfection of the $GluR2_{220-238}$ mini-gene. $GluR2_{220-238}$ is the binding site of GluR2 and Siah1. The intensity of protein bands were measured by Image J software and normalized to the corresponding control samples. FIG. 26B shows a schematic representation of $GluR2_{NT}$ mutants. GluR2-M1 94-95 KK—>AA; GluR2-M2 171-172 KK—>AA; GluR2-M3 187-188 KK—>AA. (FIG. 26C shows both GAPDH and GluR2 nuclear expression was significantly decreased in GluR2-M2 transfected HEK293T cells upon glutamate treatment (100 μM, 30 min). FIG. 26D shows GluR2-M2 inhibited glutamate-induced cell death in AMPAR transfected HEK293T cells FIG. 26E shows GAPDH was immunoprecipitated by $GluR2_{NT}$ wild type and $GluR2_{NT}$ mutants. FIG. 26F shows GluR2 translocated mainly on nuclear envelope, while GAPDH translocated mainly into nucleoplasm after AMPA receptor activation. (see G-H), CO—IP of GAPDH by GluR2 subunit (upper panel) and p53 (lower panel) in nuclear envelope and nucleoplasm of rat hippocampal neurons.

Example 13

In-Vivo Neuroprotective Activity of Peptide GluR2 NT1-3-2 in an Ischemia Model In this study, a cannula (small diameter stainless steel tubes) was implanted in the animal one week before surgery. This cannula was used to deliver the peptide GluR2 NT1-3-2 (1 μM, 0.5 μl) into hippocampus where GAPDH-GluR2 interaction is considered to occur. On the surgery day, the four vessel occlusion ischemia model was performed in order to induce ischemia. Animals were treated with the peptide GluR2 NT1-3-2 either before (30 min) or after (2 hour) the induction of ischemia to examine the neuroprotective effect of the peptide. After a 5-day recirculation period, animals were decapitated, the brains were removed and dissected to harvest the hippocampus. Cresyl violet was used to stain alive neurons in hippocampus region of each animal. Cresyl violet-stained nuclei were observed by microscope and total number of stained nuclei in CA1 region was summarized and normalized to the sham-operated group.

The results shown in FIG. 27 indicate that in-vivo treatment with polypeptides of the present invention either before ischemia or after ischemia increase neuronal survival. Specifically, peptide treatment after ischemia rescued 13.2% neurons from cell death; while peptide treatment before ischemia rescued 18.2% neurons from cell death.

The results provided herein suggest that the polypeptides of the present invention can be employed in vivo, for example, without limitation, to modulate AMPA receptor exitotoxicity in response to a variety of insults or trauma. Further, the results of the present invention suggest that the polypeptides of the present invention may be employed as preventative agents, therapeutic agents, or both.

The present invention has been described with regard to one or more embodiments. However, it will be apparent to persons skilled in the art that a number of variations and modifications can be made without departing from the scope of the invention as defined in the claims.

All citations are herein incorporated by reference.

REFERENCES

1. Hollmann, M. & Heinemann, S. Cloned glutamate receptors. *Annu. Rev. Neurosci.* 17, 31-108 (1994).
2. Bliss, T. V. P. & Collingridge, G. L. A synaptic model of memory: Long-term potentiation in the hippocampus. *Nature* 361, 31-39 (1993).
3. Simon, R. P., Swan, J. H., and Meldrum, B. S. (1984). Blockade of N-methyl-D-aspartate receptors may protect against ischemic damage in the brain. *Science* 226, 850-852.
4. Choi, D. W. (1995). Calcium: still center-stage in hypoxic-ischemic neuronal death. *Trends Neurosci.* 18, 58-60.
5. Lee J M, Zipfel G J, Choi D W The changing landscape of ischaemic brain injury mechanisms. *Nature* 1999 Jun. 24; 399 (6738 Suppl): A7-14.
6. Pulsinelli, W. A., Levy, D. E., and Duffy, T. E. (1982). Regional cerebral blood flow and glucose metabolism following transient forebrain ischemia. Ann Neurol 11, 499-502.
7. Schmidt-Kastner, R. and Freund, T. F., (1991). Selective vulnerability of the hippocampus in brain ischemia. *Neuroscience* 40, pp. 599-636.
8. Pellegrini-Giampietro, D. E., Zukin, R. S., Bennett, M. V., Choi, S. and Pulsinelli, W. A., 1992. Switch in glutamate receptor subunit gene expression in CA1 subfield of hippocampus following global ischemia in rats. *Proc. Natl. Acad. Sci. USA* 89, pp. 10499-10503
9. Gill, R., and Lodge, D. (1997). Pharmacology of AMPA antagonists and their role in neuroprotection. Int Rev Neurobiol 40, 197-232.
10. Oguro, K., Oguro, N., Kojima, T., Grooms, S. Y., Calderone, A., Zheng, X., Bennett, M. V. L. and Zukin, R. S., 1999. Knockdown of AMPA receptor GluR2 expression causes delayed neurodegeneration and increases damage by sublethal ischemia in hippocampal CA1 and CA3 neurons. *J. Neurosci.* 19, pp. 9218-9227
11. Weiss, J. H. and Sensi, S. L., 2000. $Ca^{2+}$—$Zn^{2+}$ permeable AMPA or kainate receptors: possible key factors in selective neurodegeneration. *Trends Neurosci.* 23, pp. 365-371.
12. Yin, H. Z., Sensi, S. L., Ogoshi, F., and Weiss, J. H. (2002). Blockade of Ca2+-permeable AMPA/kainate channels decreases oxygen-glucose deprivation-induced Zn2+ accumulation and neuronal loss in hippocampal pyramidal neurons. J Neurosci 22, 1273-1279
13. Wang, J., Liu, S. H., Fu, Y. P., Wang, J. H. and Lu, Y. M., 2003. Cdk5 activation induces CA1 pyramidal cell death by direct phosphorylating NMDA receptors. *Nat. Neurosci.* 6, pp. 1039-1047.
14. Greengard, P., Jen, J., Nairn, A. C. & Stevens, C. F. Enhancement of the glutamate response by cAMP-dependent protein kinase in hippocampal neurons. *Science* 253, 1135-8. (1991).
15. Wang, L. Y., Dudek, E. M., Browning, M. D. & MacDonald, J. F. Modulation of AMPA/kainate receptors in cultured murine hippocampal neurones by protein kinase C. *J Physiol* 475, 431-7. (1994).
16. Yakel, J. L., Vissavajjhala, P., Derkach, V. A., Brickey, D. A. & Soderling, T. R. Identification of a Ca2+/calmodulin-dependent protein kinase II regulatory phosphorylation site in non-N-methyl-D-aspartate glutamate receptors. *Proc Natl Acad Sci USA* 92, 1376-80. (1995).
17. Soderling, T. R. Structure and regulation of calcium/calmodulin-dependent protein kinases II and IV. *Biochim Biophys Acta* 1297, 131-8. (1996).
18. Barria, A., Derkach, V. & Soderling, T. Identification of the Ca2+/calmodulin-dependent protein kinase II regulatory phosphorylation site in the alpha-amino-3-hydroxyl-5-methyl-4-isoxazole-propionate-type glutamate receptor. *J Biol Chem* 272, 32727-30. (1997).
19. Xia, J., Zhang, X., Staudinger, J. & Huganir, R. L. Clustering of AMPA receptors by the synaptic PDZ domain-containing protein PICK1. *Neuron* 22, 179-87. (1999).
20. Dong, H. et al. GRIP: a synaptic PDZ domain-containing protein that interacts with AMPA receptors. *Nature* 386, 279-84. (1997).
21. Osten, P. et al. The AMPA receptor GluR2 C terminus can mediate a reversible, ATP-dependent interaction with NSF and alpha- and beta-SNAPs. *Neuron* 21, 99-110. (1998).
22. Daw, M. I. et al. PDZ proteins interacting with C-terminal GluR2/3 are involved in a PKC-dependent regulation of AMPA receptors at hippocampal synapses. *Neuron* 28, 873-86. (2000).
23. Allison, D. W., Gelfand, V. I., Spector, I. & Craig, A. M. Role of actin in anchoring postsynaptic receptors in cultured hippocampal neurons: differential attachment of NMDA versus AMPA receptors. *J Neurosci* 18, 2423-36. (1998).
24. O'Brien, R. J., et al., *Synaptic clustering of AMPA receptors by the extracellular immediate-early gene product Narp.* Neuron, 1999. 23(2): p. 309-23.
25. Chuang, D. M., Hough, C., and Senatorov, V. V. (2005). Glyceraldehyde-3-phosphate dehydrogenase, apoptosis, and neurodegenerative diseases. Amu Rev Pharmacol Toxicol 45, 269-290.
26. Sirover, M. A. (2005). New nuclear functions of the glycolytic protein, glyceraldehyde-3-phosphate dehydrogenase, in mammalian cells. J Cell Biochem 95, 45-52.
27. Sawa, A., et al., *Glyceraldehyde-3-phosphate dehydrogenase: nuclear translocation participates in neuronal and normeuronal cell death.* Proc Natl Acad Sci USA, 1997. 94(21): p. 11669-74.
28. Ishitani, R., et al., *Nuclear localization of overexpressed glyceraldehyde-3-phosphate dehydrogenase in cultured cerebellar neurons undergoing apoptosis.* Mol Pharmacol, 1998. 53(4): p. 701-7.
29. Ishitani, R. and D. M. Chuang, *Glyceraldehyde-3-phosphate dehydrogenase antisense oligodeoxynucleotides protect against cytosine arabinonucleoside-induced apoptosis in cultured cerebellar neurons.* Proc Natl Acad Sci USA, 1996. 93(18): p. 9937-41.
30. Hara, M. R., et al., *S-nitrosylated GAPDH initiates apoptotic cell death by nuclear translocation following Siah1 binding.* Nat Cell Biol, 2005. 7(7): p. 665-74.

31. Tsai, R. L. and H. Green, *Studies on a mammalian cell protein (P8) with affinity for DNA in vitro*. J Mol Biol, 1973. 73(3): p. 307-16.
32. Singh, R. and M. R. Green, *Sequence-specific binding of transfer RNA by glyceraldehyde-3-phosphate dehydrogenase*. Science, 1993. 259(5093): p. 365-8.
33. Baxi, M. D. and J. K. Vishwanatha, *Uracil DNA-glycosylase/glyceraldehyde-3-phosphate dehydrogenase is an Ap4A binding protein*. Biochemistry, 1995. 34(30): p. 9700-7.
34. Nagy, E. and W. F. Rigby, *Glyceraldehyde-3-phosphate dehydrogenase selectively binds AU-rich RNA in the NAD (+)-binding region (Rossmann fold)*. J Biol Chem, 1995. 270(6): p. 2755-63.
35. Schultz, D. E., C. C. Hardin, and S. M. Lemon, *Specific interaction of glyceraldehyde 3-phosphate dehydrogenase with the 5'-nontranslated RNA of hepatitis A virus*. J Biol Chem, 1996. 271(24): p. 14134-42.
36. Tisdale, E. J., *Glyceraldehyde-3-phosphate dehydrogenase is required for vesicular transport in the early secretory pathway*. J Biol Chem, 2001. 276(4): p. 2480-6.
37. Tisdale, E. J., *Glyceraldehyde-3-phosphate dehydrogenase is phosphorylated by protein kinase Ciota/lambda and plays a role in microtubule dynamics in the early secretory pathway*. J Biol Chem, 2002. 277(5): p. 3334-41.
38. Tisdale, E. J., C. Kelly, and C. R. Artalejo, *From ER to Golgi: Glyceraldehyde-3-phosphate dehydrogenase interacts with Rab2 and plays an essential role in endoplasmic reticulum to Golgi transport exclusive of its glycolytic activity*. J Biol Chem, 2004. 279(52): p. 54046-52.
39. Kumagai, H. and H. Sakai, *A porcine brain protein (35 K protein) which bundles microtubules and its identification as glyceraldehyde 3-phosphate dehydrogenase*. J Biochem (Tokyo), 1983. 93(5): p. 1259-69.
40. Glaser, P. E., X. Han, and R. W. Gross, *Tubulin is the endogenous inhibitor of the glyceraldehyde 3-phosphate dehydrogenase isoform that catalyzes membrane fusion: Implications for the coordinated regulation of glycolysis and membranefusion*. Proc Natl Acad Sci USA, 2002. 99(22): p. 14104-9.
41. Sawa, A., et al., *Glyceraldehyde-3-phosphate dehydrogenase: nuclear translocation participates in neuronal and nonneuronal cell death*. Proc Natl Acad Sci USA, 1997. 94(21): p. 11669-74.
42. Ishitani, R., et al., *Nuclear localization of overexpressed glyceraldehyde-3-Phosphate dehydrogenase in cultured cerebellar neurons undergoing apoptosis*. Mol Pharmacol, 1998. 53(4): p. 701-7.
43. Ishitani, R. and D. M. Chuang, *Glyceraldehyde-3-phosphate dehydrogenase antisense oligodeoxynucleotides protect against cytosine arabinonucleoside-induced apoptosis in cultured cerebellar neurons*. Proc Natl Acad Sci USA, 1996. 93(18): p. 9937-41.
44. Hara, M. R., et al., *S-nitrosylated GAPDH initiates apoptotic cell death by nuclear translocation following Siah1 binding*. Nat Cell Biol, 2005. 7(7): p. 665-74.
45. Chen, R. W., Saunders, P. A., Wei, H., Li, Z., Seth, P., and Chuang, D. M. (1999). Involvement of glyceraldehyde-3-phosphate dehydrogenase (GAPDH) and p53 in neuronal apoptosis: evidence that GAPDH is upregulated by p53. J Neurosci 19, 9654-9662.
46. Dastoor, Z., and Dreyer, J. L. (2001). Potential role of nuclear translocation of glyceraldehyde-3-phosphate dehydrogenase in apoptosis and oxidative stress. J Cell Sci 114, 1643-1653.
47. Barbosa M. S. Bao, S. N., Andreotti, P. F., de Faria, F. P., Felipe, M. S., dos Santos Feitosa, L., Mendes-Giarmini, M. J., and Soares, C. M. (2006). Glyceraldehyde-3-phosphate dehydrogenase of Paracoccidioides brasiliensis is a cell surface protein involved in fungal adhesion to extracellular matrix proteins and interaction with cells. Infect Immun 74, 382-389. Bhattacharya
48. Bhattacharya, M., Peri, K., Ribeiro-da-Silva, A., Almazan, G., Shichi, H., Hou, X., Varma, D. R., and Chemtob, S. (1999). Localization of functional prostaglandin E2 receptors EP3 and EP4 in the nuclear envelope. The Journal of biological chemistry 274, 15719-15724.
49. Bkaily, G., Choufani, S., Hassan, G., E1-Bizri, N., Jacques, D., and D'Orleans-Juste, P. (2000). Presence of functional endothelin-1 receptors in nuclear membranes of human aortic vascular smooth muscle cells. Journal of cardiovascular pharmacology 36, S414-417.
50. Bliss, T. V., and Collingridge, G. L. (1993). A synaptic model of memory: long-term potentiation in the hippocampus. Nature 361, 31-39.
51. Brooks, C. L., and Gu, W. (2003). Ubiquitination, phosphorylation and acetylation: the molecular basis for p53 regulation. Current opinion in cell biology 15, 164-171.
52. Carriedo, S. G., Yin, H. Z., Sensi, S. L., and Weiss, J. H. (1998). Rapid Ca2+ entry through Ca2+-permeable AMPA/Kainate channels triggers marked intracellular Ca2+ rises and consequent oxygen radical production. J Neurosci 18, 7727-7738.
53. Carroll, R. C., Beattie, E. C., Xia, H., Luscher, C., Altschuler, Y., Nicoll, R. A., Malenka, R. C., and von Zastrow, M. (1999). Dynamin-dependent endocytosis of ionotropic glutamate receptors. Proceedings of the National Academy of Sciences of the United States of America 96, 14112-14117.
54. Chen, L., Chetkovich, D. M., Petralia, R. S., Sweeney, N. T., Kawasaki, Y., Wenthold, R. J., Bredt, D. S., and Nicoll, R. A. (2000). Stargazin regulates synaptic targeting of AMPA receptors by two distinct mechanisms. Nature 408, 936-943.
55. Choi, Y. D., and Dreyfuss, G. (1984). Isolation of the heterogeneous nuclear RNA-ribonucleoprotein complex (hnRNP): a unique supramolecular assembly. Proceedings of the National Academy of Sciences of the United States of America 81, 7471-7475.
56. Dong, H., O'Brien, R. J., Fung, E. T., Lanahan, A. A., Worley, P. F., and Huganir, R. L. (1997). GRIP: a synaptic PDZ domain-containing protein that interacts with AMPA receptors. Nature 386, 279-284.
57. Dong, H., Zhang, P., Song, I., Petralia, R. S., Liao, D., and Huganir, R. L. (1999). Characterization of the glutamate receptor-interacting proteins GRIP1 and GRIP2. J Neurosci 19, 6930-6941.
58. Doucet, J. P., and Tuana, B. S. (1991). Identification of low molecular weight GTP-binding proteins and their sites of interaction in subcellular fractions from skeletal muscle. The Journal of biological chemistry 266, 17613-17620.
59. Fuchtbauer, A., Jockusch, B. M., Leberer, E., and Pette, D. (1986). Actin-severing activity copurifies with phosphofructokinase. Proceedings of the National Academy of Sciences of the United States of America 83, 9502-9506.
60. Geiger, J. R., Melcher, T., Koh, D. S., Sakmann, B., Seeburg, P. H., Jonas, P., and Monyer, H. (1995). Relative abundance of subunit mRNAs determines gating and Ca2+ permeability of AMPA receptors in principal neurons and interneurons in rat CNS. Neuron 15, 193-204.
61. Gill, R., and Lodge, D. (1997). Pharmacology of AMPA antagonists and their role in neuroprotection. International review of neurobiology 40, 197-232.

62. Glaser, P. E., and Gross, R. W. (1995). Rapid plasmenylethanolamine-selective fusion of membrane bilayers catalyzed by an isoform of glyceraldehyde-3-phosphate dehydrogenase: discrimination between glycolytic and fusogenic roles of individual isoforms. Biochemistry 34, 12193-12203.

63. Hara, M. R., Agrawal, N., Kim, S. F., Cascio, M. B., Fujimuro, M., Ozeki, Y., Takahashi, M., Cheah, J. H., Tankou, S. K., Hester, L. D., et al. (2005). S-nitrosylated GAPDH initiates apoptotic cell death by nuclear translocation following Siah1 binding. Nature cell biology 7, 665-674.

64. Hara, M. R., Thomas, B., Cascio, M. B., Bae, B. I., Hester, L. D., Dawson, V. L., Dawson, T. M., Sawa, A., and Snyder, S. H. (2006). Neuroprotection by pharmacologic blockade of the GAPDH death cascade. Proceedings of the National Academy of Sciences of the United States of America 103, 3887-3889.

65. Huitorel, P., and Pantaloni, D. (1985). Bundling of microtubules by glyceraldehyde-3-phosphate dehydrogenase and its modulation by ATP. Eur J Biochem 150, 265-269.

66. Humbert, J. P., Matter, N., Artault, J. C., Koppler, P., and Malviya, A. N. (1996). Inositol 1,4,5-trisphosphate receptor is located to the inner nuclear membrane vindicating regulation of nuclear calcium signaling by inositol 1,4,5-trisphosphate. Discrete distribution of inositol phosphate receptors to inner and outer nuclear membranes. The Journal of biological chemistry 271, 478-485.

67. Iihara, K., Joo, D. T., Henderson, J., Sattler, R., Taverna, F. A., Lourensen, S., Orser, B. A., Roder, J. C., and Tymianski, M. (2001). The influence of glutamate receptor 2 expression on excitotoxicity in Glur2 null mutant mice. J Neurosci 21, 2224-2239.

68. Ikemoto, A., Bole, D. G., and Ueda, T. (2003). Glycolysis and glutamate accumulation into synaptic vesicles. Role of glyceraldehyde phosphate dehydrogenase and 3-phosphoglycerate kinase. The Journal of biological chemistry 278, 5929-5940.

69. Jonas, P., Racca, C., Sakmann, B., Seeburg, P. H., and Monyer, H. (1994). Differences in Ca2+ permeability of AMPA-type glutamate receptor channels in neocortical neurons caused by differential GluR-B subunit expression. Neuron 12, 1281-1289.

70. Jong, Y. J., Kumar, V., Kingston, A. E., Romano, C., and O'Malley, K. L. (2005). Functional metabotropic glutamate receptors on nuclei from brain and primary cultured striatal neurons. Role of transporters in delivering ligand. The Journal of biological chemistry 280, 30469-30480.

71. Jong, Y. J., Schwetye, K. E., and O'Malley, K. L. (2007). Nuclear localization of functional metabotropic glutamate receptor mGlul in HEK293 cells and cortical neurons: role in nuclear calcium mobilization and development. Journal of neurochemistry 101, 458-469.

72. Lakkaraju, A., Dubinsky, J. M., Low, W. C., and Rahman, Y. E. (2001). Neurons are protected from excitotoxic death by p53 antisense oligonucleotides delivered in anionic liposomes. The Journal of biological chemistry 276, 32000-32007.

73. Lee, F. J., Xue, S., Pei, L., Vukusic, B., Chery, N., Wang, Y., Wang, Y. T., Niznik, H. B., Yu, X. M., and Liu, F. (2002a). Dual regulation of NMDA receptor functions by direct protein-protein interactions with the dopamine D1 receptor. Cell 111, 219-230.

74. Lee, S. H., Liu, L., Wang, Y. T., and Sheng, M. (2002b). Clathrin adaptor AP2 and NSF interact with overlapping sites of GluR2 and play distinct roles in AMPA receptor trafficking and hippocampal LTD. Neuron 36, 661-674.

75. Li, S. Y., Ni, J. H., Xu, D. S., and Jia, H. T. (2003). Down-regulation of GluR2 is associated with Ca2+-dependent protease activities in kainate-induced apoptotic cell death in cultured [correction of culturd] rat hippocampal neurons. Neuroscience letters 352, 105-108.

76. Lin, J. W., Ju, W., Foster, K., Lee, S. H., Ahmadian, G., Wyszynski, M., Wang, Y. T., and Sheng, M. (2000). Distinct molecular mechanisms and divergent endocytotic pathways of AMPA receptor internalization. Nature neuroscience 3, 1282-1290.

77. Lin, S. Y., Maidno, K., Xia, W., Matin, A., Wen, Y., Kwong, K. Y., Bourguignon, L., and Hung, M. C. (2001). Nuclear localization of EGF receptor and its potential new role as a transcription factor. Nature cell biology 3, 802-808.

78. Liu, B., Liao, M., Mielke, J. G., Ning, K., Chen, Y., Li, L., E I-Hayek, Y. H., Gomez, E., Zukin, R. S., Fehlings, M. G., et al. (2006). Ischemic insults direct glutamate receptor subunit 2-lacking AMPA receptors to synaptic sites. J Neurosci 26, 5309-5319.

79. Liu, F., Wan, Q., Pristupa, Z. B., Yu, X. M., Wang, Y. T., and Niznik, H. B. (2000). Direct protein-protein coupling enables cross-talk between dopamine D5 and gamma-aminobutyric acid A receptors. Nature 403, 274-280.

80. Liu, S., Lau, L., Wei, J., Zhu, D., Zou, S., Sun, H. S., Fu, Y., Liu, F., and Lu, Y. (2004). Expression of Ca(2+)-permeable AMPA receptor channels primes cell death in transient forebrain ischemia. Neuron 43, 43-55.

81. Lu, D., Yang, H., Shaw, G., and Raizada, M. K. (1998). Angiotensin II-induced nuclear targeting of the angiotensin type 1 (AT1) receptor in brain neurons. Endocrinology 139, 365-375.

82. Man, H. Y., Lin, J. W., Ju, W. H., Ahmadian, G., Liu, L., Becker, L. E., Sheng, M., and Wang, Y. T. (2000). Regulation of AMPA receptor-mediated synaptic transmission by clathrin-dependent receptor internalization. Neuron 25, 649-662.

83. Melikian, H. E., and Buckley, K. M. (1999). Membrane trafficking regulates the activity of the human dopamine transporter. J Neurosci 19, 7699-7710.

84. Miller, F. D., Pozniak, C. D., and Walsh, G. S. (2000). Neuronal life and death: an essential role for the p53 family. Cell death and differentiation 7, 880-888.

85. Nelson, D., Goldstein, J. M., Boatright, K., Harty, D. W., Cook, S. L., Hickman, P. J., Potempa, J., Travis, J., and Mayo, J. A. (2001). pH-regulated secretion of a glyceraldehyde-3-phosphate dehydrogenase from *Streptococcus gordonii* FSS2: purification, characterization, and cloning of the gene encoding this enzyme. J Dent Res 80, 371-377.

86. Nishimune, A., Isaac, J. T., Molnar, E., Noel, J., Nash, S. R., Tagaya, M., Collingridge, G. L., Nakanishi, S., and Henley, J. M. (1998). NSF binding to GluR2 regulates synaptic transmission. Neuron 21, 87-97.

87. Oguro, K., Oguro, N., Kojima, T., Grooms, S. Y., Calderone, A., Zheng, X., Bennett, M. V., and Zukin, R. S. (1999). Knockdown of AMPA receptor GluR2 expression causes delayed neurodegeneration and increases damage by sublethal ischemia in hippocampal CA1 and CA3 neurons. J Neurosci 19, 9218-9227.

88. Osten, P., Srivastava, S., Inman, G. J., Vilim, F. S., Khatri, L., Lee, L. M., States, B. A., Einheber, S., Milner, T. A., Hanson, P. I., et al. (1998). The AMPA receptor GluR2 C terminus can mediate a reversible, ATP-dependent interaction with NSF and alpha- and beta-SNAPs. Neuron 21, 99-110.

89. Robbins, A. R., Ward, R. D., and Oliver, C. (1995). A mutation in glyceraldehyde 3-phosphate dehydrogenase alters endocytosis in CHO cells. J Cell Biol 130, 1093-1104.
90. Saglietti, L., Dequidt, C., Kamieniarz, K., Rousset, M. C., Valnegri, P., Thoumine, O., Beretta, F., Fagni, L., Choquet, D., Sala, C., et al., (2007). Extracellular interactions between GluR2 and N-cadherin in spine regulation. Neuron 54, 461-477.
91. Sakhi, S., Bruce, A., Sun, N., Tocco, G., Baudry, M., and Schreiber, S. S. (1994). p53 induction is associated with neuronal damage in the central nervous system. Proceedings of the National Academy of Sciences of the United States of America 91, 7525-7529.
92. Schmidt-Kastner, R., and Freund, T. F. (1991). Selective vulnerability of the hippocampus in brain ischemia. Neuroscience 40, 599-636.
93. Seifert, K. N., McArthur, W. P., Bleiweis, A. S., and Brady, L. J. (2003). Characterization of group B streptococcal glyceraldehyde-3-phosphate dehydrogenase: surface localization, enzymatic activity, and protein-protein interactions. Can J Microbiol 49, 350-356.
94. Srivastava, S., Osten, P., Vilim, F. S., Khatri, L., Inman, G., States, B., Daly, C., DeSouza, S., Abagyan, R., Valtschanoff, J. G., et al. (1998). Novel anchorage of GluR2/3 to the postsynaptic density by the AMPA receptor-binding protein ABP. Neuron 21, 581-591.
95. Uberti, D., Belloni, M., Grilli, M., Spano, P., and Memo, M. (1998). Induction of tumour-suppressor phosphoprotein p53 in the apoptosis of cultured rat cerebellar neurones triggered by excitatory amino acids. Eur J Neurosci 10, 246-254.
96. Valtschanoff, J. G., Burette, A., Davare, M. A., Leonard, A. S., Hell, J. W., and Weinberg, R. J. (2000). SAP97 concentrates at the postsynaptic density in cerebral cortex. Eur J Neurosci 12, 3605-3614.
97. Ventura, C., Maioli, M., Pintos, G., Posadino, A. M., and Tadolini, B. (1998). Nuclear opioid receptors activate opioid peptide gene transcription in isolated myocardial nuclei. The Journal of biological chemistry 273, 13383-13386.
98. Weiss, J. H., and Sensi, S. L. (2000). Ca2+-Zn2+ permeable AMPA or kainate receptors: possible key factors in selective neurodegeneration. Trends in neurosciences 23, 365-371.
99. Wyszynski, M., Valtschanoff, J. G., Naisbitt, S., Dunah, A. W., Kim, E., Standaert, D. G., Weinberg, R., and Sheng, M. (1999). Association of AMPA receptors with a subset of glutamate receptor-interacting protein in vivo. J Neurosci 19, 6528-6537.
100. Xia, J., Zhang, X., Staudinger, J., and Huganir, R. L. (1999). Clustering of AMPA receptors by the synaptic PDZ domain-containing protein PICK1. Neuron 22, 179-187.
101. Yamaji, R., Chatani, E., Harada, N., Sugimoto, K., Inui, H., and Nakano, Y. (2005). Glyceraldehyde-3-phosphate dehydrogenase in the extracellular space inhibits cell spreading. Biochimica et biophysica acta 1726, 261-271.
102. Yin, H. Z., Sensi, S. L., Ogoshi, F., and Weiss, J. H. (2002). Blockade of Ca2+-permeable AMPA/kainate channels decreases oxygen-glucose deprivation-induced Zn2+ accumulation and neuronal loss in hippocampal pyramidal neurons. J Neurosci 22, 1273-1279.
103. Zeevalk, G. D., Schoepp, D., and Nicklas, W. J. (1995). Excitotoxicity at both NMDA and non-NMDA glutamate receptors is antagonized by aurintricarboxylic acid: evidence for differing mechanisms of action. Journal of neurochemistry 64, 1749-1758.

What is claimed is:

1. A polypeptide of between 31 and 200 amino acids comprising a GluR2 NT1-3-2 (Y142-K172) amino acid sequence defined by (SEQ ID NO:1).

2. The polypeptide of claim 1, wherein said polypeptide is covalently attached to a heterologous polypeptide, to form a fusion protein, wherein said heterologous polypeptide does not encompass a GluR2 subunit sequence.

3. The polypeptide of claim 2, wherein said fusion protein comprises a protein transduction domain.

4. The polypeptide of claim 1, said polypeptide attached covalently or non-covalently to a non-protein substrate, non-protein molecule, non-protein macromolecule, a support, or any combination thereof.

5. The polypeptide of claim 4, wherein the polypeptide, non-protein substrate, non-protein molecule, non-protein macromolecule, support or any combination thereof is labeled.

6. An in-vitro method of inhibiting AMPA receptor-mediated excitotoxicity comprising, administering the polypeptide of claim 1 to a cell or tissue comprising an AMPA receptor.

7. A method of inhibiting GAPDH association with a GluR2 subunit comprising administering the polypeptide of claim 1 to a solution, cell, cell culture, or tissue comprising GAPDH and the GluR2 subunit.

8. A kit comprising, a) the polypeptide defined by claim 1 and, b) one or more diluents, delivery vehicles, pharmaceutically acceptable excipients, or a combination thereof.

9. A composition comprising the excitotoxicity-inhibiting polypeptide of claim 1 and one or more diluents, delivery vehicles, pharmaceutically acceptable excipients, or a combination thereof.

10. The polypeptide of claim 1, wherein said polypeptide consists of SEQ ID NO:1.

11. A method of increasing neuronal survival in a subject following an ischemic event, comprising administering the polypeptide as defined by claim 1 to a subject before or after the ischemic event.

12. The method of claim 11, wherein said polypeptide consists of SEQ ID NO:1.

* * * * *

SEQUENCE LISTING

```
<160> NUMBER OF SEQ ID NOS: 9

<210> SEQ ID NO 1
<211> LENGTH: 31
<212> TYPE: PRT
<213> ORGANISM: Artificial Sequence
<220> FEATURE:
<223> OTHER INFORMATION: Y142-K172 of GluR2 subunit receptor from homo
      sapiens

<400> SEQUENCE: 1

Tyr Tyr Gln Trp Asp Lys Phe Ala Tyr Leu Tyr Asp Ser Asp Arg Gly
1               5                   10                  15

Leu Ser Thr Leu Gln Ala Val Leu Asp Ser Ala Ala Glu Lys Lys
            20                  25                  30


<210> SEQ ID NO 2
<211> LENGTH: 30
<212> TYPE: PRT
<213> ORGANISM: Artificial Sequence
<220> FEATURE:
<223> OTHER INFORMATION: I221-E250 of GAPDH polypeptide from homo
      sapiens

<400> SEQUENCE: 2

Ile Pro Glu Leu Asn Gly Lys Leu Thr Gly Met Ala Phe Arg Val Pro
1               5                   10                  15

Thr Ala Asn Val Ser Val Val Asp Leu Thr Cys Arg Leu Glu
            20                  25                  30
```

<210> SEQ ID NO 3
<211> LENGTH: 1635
<212> TYPE: DNA
<213> ORGANISM: Rattus norvegicus

<400> SEQUENCE: 3

```
atgcaaaaga ttatgcatat ttctgtcctc ctttctcctg ttttatgggg actgattttt     60

ggtgtctctt ctaacagcat acagataggg gggctatttc caaggggcgc tgatcaagaa    120

tacagtgcat ttcgggtagg gatggttcag ttttccactt cggagttcag actgacaccc    180

catatcgaca atttggaggt agccaacagt ttcgcagtca ccaatgcttt ctgctcccag    240

ttttcaagag gagtctacgc aatttttgga ttttatgaca agaagtctgt aaataccatc    300

acatcattct gtgggacact ccatgtgtcc ttcatcacac ctagcttccc aacagatggc    360

acacatccat ttgtcatcca gatgcgacct gacctcaaag gagcactcct tagcttgatt    420

gagtactacc aatgggacaa gttcgcatac ctctatgaca gtgacagagg cttatcaaca    480

ctgcaagctg ttctggattc tgctgcagag aagaagtggc aggtgactgc tatcaatgtg    540

gggaacatca acaatgacaa gaaagatgag acctacagat cgctctttca agatctggag    600

ttaaaaaaag aacggcgtgt aatcctggac tgtgaaaggg ataaagtaaa tgacattgtg    660

gaccaggtta ttaccattgg aaaacatgtt aaagggtacc attatatcat tgcaaatctg    720

ggattcactg atggggacct gctgaaaatt cagtttggag gagcaaatgt ctctggattt    780

cagattgtag actacgatga ttccctggtg tctaaattta tagaaagatg gtcaacactg    840

gaagagaaag aataccctgg agcacacaca gcgacaatta agtatacttc ggccctgacg    900

tatgatgctg tccaagtgat gactgaagca ttccgtaacc ttcggaagca gaggattgaa    960

atatcccgga gaggaaatgc aggggattgt ttggccaacc cagctgtgcc ctggggacaa   1020

ggggtcgaaa tagaaagggc cctcaagcag gttcaagttg aaggcctctc tggaaatata   1080

aagtttgacc agaatggaaa acgaataaac tacacaatta acatcatgga gctcaaaaca   1140

aatggacccc ggaagattgg gtactggagt gaagtggata aaatggttgt caccctaact   1200

gagctcccat caggaaatga cacgtctggg cttgaaaaca agactgtggt ggtcaccaca   1260

atattggaat ctccatatgt tatgatgaag aaaaatcatg aaatgcttga agggaatgag   1320

cgttacgagg gctactgtgt tgacttagct gcagaaattg ccaaacactg tgggttcaag   1380

tacaagctga ctattgttgg ggatggcaag tatggggcca gggatgccga caccaaaatt   1440

tggaatggta tggttggaga gcttgtctac gggaaagctg acattgcaat tgctccatta   1500

actatcactc tcgtgagaga agaggtgatt gacttctcca agcccttcat gagtcttgga   1560

atctctatca tgatcaagaa gcctcagaag tccaaaccag gagtgttttc ctttcttgat   1620

cctttagcct atgag                                                    1635
```

<210> SEQ ID NO 4
<211> LENGTH: 524
<212> TYPE: PRT
<213> ORGANISM: Rattus norvegicus

<400> SEQUENCE: 4

```
Val Ser Ser Asn Ser Ile Gln Ile Gly Gly Leu Phe Pro Arg Gly Ala
1               5                   10                  15

Asp Gln Glu Tyr Ser Ala Phe Arg Val Gly Met Val Gln Phe Ser Thr
            20                  25                  30

Ser Glu Phe Arg Leu Thr Pro His Ile Asp Asn Leu Glu Val Ala Asn
```

-continued

```
        35                  40                  45

Ser Phe Ala Val Thr Asn Ala Phe Cys Ser Gln Phe Ser Arg Gly Val
    50                  55                  60

Tyr Ala Ile Phe Gly Phe Tyr Asp Lys Lys Ser Val Asn Thr Ile Thr
65                  70                  75                  80

Ser Phe Cys Gly Thr Leu His Val Ser Phe Ile Thr Pro Ser Phe Pro
                85                  90                  95

Thr Asp Gly Thr His Pro Phe Val Ile Gln Met Arg Pro Asp Leu Lys
            100                 105                 110

Gly Ala Leu Leu Ser Leu Ile Glu Tyr Tyr Gln Trp Asp Lys Phe Ala
        115                 120                 125

Tyr Leu Tyr Asp Ser Asp Arg Gly Leu Ser Thr Leu Gln Ala Val Leu
    130                 135                 140

Asp Ser Ala Ala Glu Lys Lys Trp Gln Val Thr Ala Ile Asn Val Gly
145                 150                 155                 160

Asn Ile Asn Asn Asp Lys Lys Asp Glu Thr Tyr Arg Ser Leu Phe Gln
                165                 170                 175

Asp Leu Glu Leu Lys Lys Glu Arg Arg Val Ile Leu Asp Cys Glu Arg
            180                 185                 190

Asp Lys Val Asn Asp Ile Val Asp Gln Val Ile Thr Ile Gly Lys His
        195                 200                 205

Val Lys Gly Tyr His Tyr Ile Ile Ala Asn Leu Gly Phe Thr Asp Gly
    210                 215                 220

Asp Leu Leu Lys Ile Gln Phe Gly Gly Ala Asn Val Ser Gly Phe Gln
225                 230                 235                 240

Ile Val Asp Tyr Asp Asp Ser Leu Val Ser Lys Phe Ile Glu Arg Trp
                245                 250                 255

Ser Thr Leu Glu Glu Lys Glu Tyr Pro Gly Ala His Thr Ala Thr Ile
            260                 265                 270

Lys Tyr Thr Ser Ala Leu Thr Tyr Asp Ala Val Gln Val Met Thr Glu
        275                 280                 285

Ala Phe Arg Asn Leu Arg Lys Gln Arg Ile Glu Ile Ser Arg Arg Gly
    290                 295                 300

Asn Ala Gly Asp Cys Leu Ala Asn Pro Ala Val Pro Trp Gly Gln Gly
305                 310                 315                 320

Val Glu Ile Glu Arg Ala Leu Lys Gln Val Gln Val Glu Gly Leu Ser
                325                 330                 335

Gly Asn Ile Lys Phe Asp Gln Asn Gly Lys Arg Ile Asn Tyr Thr Ile
            340                 345                 350

Asn Ile Met Glu Leu Lys Thr Asn Gly Pro Arg Lys Ile Gly Tyr Trp
        355                 360                 365

Ser Glu Val Asp Lys Met Val Val Thr Leu Thr Glu Leu Pro Ser Gly
    370                 375                 380

Asn Asp Thr Ser Gly Leu Glu Asn Lys Thr Val Val Val Thr Thr Ile
385                 390                 395                 400

Leu Glu Ser Pro Tyr Val Met Met Lys Lys Asn His Glu Met Leu Glu
                405                 410                 415

Gly Asn Glu Arg Tyr Glu Gly Tyr Cys Val Asp Leu Ala Ala Glu Ile
            420                 425                 430

Ala Lys His Cys Gly Phe Lys Tyr Lys Leu Thr Ile Val Gly Asp Gly
        435                 440                 445

Lys Tyr Gly Ala Arg Asp Ala Asp Thr Lys Ile Trp Asn Gly Met Val
    450                 455                 460
```

```
Gly Glu Leu Val Tyr Gly Lys Ala Asp Ile Ala Ile Ala Pro Leu Thr
465                 470                 475                 480

Ile Thr Leu Val Arg Glu Glu Val Ile Asp Phe Ser Lys Pro Phe Met
                485                 490                 495

Ser Leu Gly Ile Ser Ile Met Ile Lys Lys Pro Gln Lys Ser Lys Pro
            500                 505                 510

Gly Val Phe Ser Phe Leu Asp Pro Leu Ala Tyr Glu
        515                 520


<210> SEQ ID NO 5
<211> LENGTH: 335
<212> TYPE: PRT
<213> ORGANISM: homo sapiens

<400> SEQUENCE: 5

Met Gly Lys Val Lys Val Gly Val Asn Gly Phe Gly Arg Ile Gly Arg
1               5                   10                  15

Leu Val Thr Arg Ala Ala Phe Asn Ser Gly Lys Val Asp Ile Val Ala
            20                  25                  30

Ile Asn Asp Pro Phe Ile Asp Leu Asn Tyr Met Val Tyr Met Phe Gln
        35                  40                  45

Tyr Asp Ser Thr His Gly Lys Phe His Gly Thr Val Lys Ala Glu Asn
    50                  55                  60

Gly Lys Leu Val Ile Asn Gly Asn Pro Ile Thr Ile Phe Gln Glu Arg
65                  70                  75                  80

Asp Pro Ser Lys Ile Lys Trp Gly Asp Ala Gly Ala Glu Tyr Val Val
                85                  90                  95

Glu Ser Thr Gly Val Phe Thr Thr Met Glu Lys Ala Gly Ala His Leu
            100                 105                 110

Gln Gly Gly Ala Lys Arg Val Ile Ile Ser Ala Pro Ser Ala Asp Ala
        115                 120                 125

Pro Met Phe Val Met Gly Val Asn His Glu Lys Tyr Asp Asn Ser Leu
    130                 135                 140

Lys Ile Ile Ser Asn Ala Ser Cys Thr Thr Asn Cys Leu Ala Pro Leu
145                 150                 155                 160

Ala Lys Val Ile His Asp Asn Phe Gly Ile Val Glu Gly Leu Met Thr
                165                 170                 175

Thr Val His Ala Ile Thr Ala Thr Gln Lys Thr Val Asp Gly Pro Ser
            180                 185                 190

Gly Lys Leu Trp Arg Asp Gly Arg Gly Ala Leu Gln Asn Ile Ile Pro
        195                 200                 205

Ala Ser Thr Gly Ala Ala Lys Ala Val Gly Lys Val Ile Pro Glu Leu
    210                 215                 220

Asn Gly Lys Leu Thr Gly Met Ala Phe Arg Val Pro Thr Ala Asn Val
225                 230                 235                 240

Ser Val Val Asp Leu Thr Cys Arg Leu Glu Lys Pro Ala Lys Tyr Asp
                245                 250                 255

Asp Ile Lys Lys Val Val Lys Gln Ala Ser Glu Gly Pro Leu Lys Gly
            260                 265                 270

Ile Leu Gly Tyr Thr Glu His Gln Val Val Ser Ser Asp Phe Asn Ser
        275                 280                 285

Asp Thr His Ser Ser Thr Phe Asp Ala Gly Ala Gly Ile Ala Leu Asn
    290                 295                 300

Asp His Phe Val Lys Leu Ile Ser Trp Tyr Asp Asn Glu Phe Gly Tyr
305                 310                 315                 320
```

Ser Asn Arg Val Val Asp Leu Met Ala His Met Ala Ser Lys Glu
325 330 335

<210> SEQ ID NO 6
<211> LENGTH: 21
<212> TYPE: PRT
<213> ORGANISM: Rattus norvegicus

<400> SEQUENCE: 6

Val Ile Ile Ser Ala Pro Ser Ala Asp Ala Pro Met Phe Val Met Gly
1 5 10 15

Val Asn His Glu Lys
20

<210> SEQ ID NO 7
<211> LENGTH: 24
<212> TYPE: PRT
<213> ORGANISM: Rattus norvegicus

<400> SEQUENCE: 7

Val Ile His Asp Asn Phe Gly Ile Val Glu Gly Leu Met Thr Thr Val
1 5 10 15

His Ala Ile Thr Ala Thr Gln Lys
20

<210> SEQ ID NO 8
<211> LENGTH: 14
<212> TYPE: PRT
<213> ORGANISM: Rattus norvegicus

<400> SEQUENCE: 8

Val Pro Thr Pro Asn Val Ser Val Val Asp Leu Thr Cys Arg
1 5 10

<210> SEQ ID NO 9
<211> LENGTH: 333
<212> TYPE: PRT
<213> ORGANISM: Rattus norvegicus

<400> SEQUENCE: 9

Met Val Lys Val Gly Val Asn Gly Phe Gly Arg Ile Gly Arg Leu Val
1 5 10 15

Thr Arg Ala Ala Phe Ser Cys Asp Lys Val Asp Ile Val Ala Ile Asn
20 25 30

Asp Pro Phe Ile Asp Leu Asn Tyr Met Val Tyr Met Phe Gln Tyr Asp
35 40 45

Ser Thr His Gly Lys Phe Asn Gly Thr Val Lys Ala Glu Asn Gly Lys
50 55 60

Leu Val Ile Asn Gly Lys Pro Ile Thr Ile Phe Gln Glu Arg Asp Pro
65 70 75 80

Val Lys Ile Lys Trp Gly Asp Ala Gly Ala Glu Tyr Val Val Glu Ser
85 90 95

Thr Gly Val Phe Thr Thr Met Glu Lys Ala Gly Ala His Leu Lys Gly
100 105 110

Gly Ala Lys Arg Val Ile Ile Ser Ala Pro Ser Ala Asp Ala Pro Met
115 120 125

Phe Val Met Gly Val Asn His Glu Lys Tyr Asp Asn Ser Leu Lys Ile
130 135 140

Val Ser Asn Ala Ser Cys Thr Thr Asn Cys Leu Ala Pro Leu Ala Lys
145 150 155 160

-continued

```
Val Ile His Asp Asn Phe Gly Ile Val Glu Gly Leu Met Thr Thr Val
                165                 170                 175

His Ala Ile Thr Ala Thr Gln Lys Thr Val Asp Gly Pro Ser Gly Lys
            180                 185                 190

Leu Trp Arg Asp Gly Arg Gly Ala Ala Gln Asn Ile Ile Pro Ala Ser
        195                 200                 205

Thr Gly Ala Ala Lys Ala Val Gly Lys Val Ile Pro Glu Leu Asn Gly
    210                 215                 220

Lys Leu Thr Gly Met Ala Phe Arg Val Pro Thr Pro Asn Val Ser Val
225                 230                 235                 240

Val Asp Leu Thr Cys Arg Leu Glu Lys Pro Ala Lys Tyr Asp Asp Ile
                245                 250                 255

Lys Lys Val Val Lys Gln Ala Ala Glu Gly Pro Leu Lys Gly Ile Leu
            260                 265                 270

Gly Tyr Thr Glu Asp Gln Val Val Ser Cys Asp Phe Asn Ser Asn Ser
        275                 280                 285

His Ser Ser Thr Phe Asp Ala Gly Ala Gly Ile Ala Leu Asn Asp Asn
    290                 295                 300

Ile Val Lys Leu Ile Ser Trp Tyr Asp Asn Glu Tyr Gly Tyr Ser Asn
305                 310                 315                 320

Arg Val Val Asp Leu Met Ala Tyr Met Ala Ser Lys Glu
                325                 330
```